United States Patent
Zheng et al.

(10) Patent No.: US 12,084,423 B2
(45) Date of Patent: Sep. 10, 2024

(54) PIPERLONGUMINE ANALOGUES AND USES THEREOF

(71) Applicant: BioVentures, LLC, Little Rock, AR (US)

(72) Inventors: Guangrong Zheng, Little Rock, AR (US); Daohong Zhou, Little Rock, AR (US); Xuan Zhang, Little Rock, AR (US)

(73) Assignee: BioVentures, LLC, Little Rock, AR (US)

( * ) Notice: Subject to any disclaimer, the term of this patent is extended or adjusted under 35 U.S.C. 154(b) by 967 days.

(21) Appl. No.: 17/056,705

(22) PCT Filed: May 18, 2018

(86) PCT No.: PCT/US2018/033479
§ 371 (c)(1),
(2) Date: Nov. 18, 2020

(87) PCT Pub. No.: WO2019/221755
PCT Pub. Date: Nov. 21, 2019

(65) Prior Publication Data
US 2021/0206725 A1  Jul. 8, 2021

(51) Int. Cl.
*A61K 31/44* (2006.01)
*A61K 45/06* (2006.01)
*C07D 211/88* (2006.01)
*C07D 223/10* (2006.01)
*C07D 265/02* (2006.01)

(52) U.S. Cl.
CPC ............ *C07D 223/10* (2013.01); *A61K 45/06* (2013.01); *C07D 211/88* (2013.01); *C07D 265/02* (2013.01)

(58) Field of Classification Search
CPC ...................................................... A61K 31/44
USPC .................................................... 514/212.03
See application file for complete search history.

(56) References Cited

U.S. PATENT DOCUMENTS

| | | |
|---|---|---|
| 4,241,046 A | 12/1980 | Papahadjopoulos et al. |
| 4,394,448 A | 7/1983 | Szoka, Jr. et al. |
| 4,529,561 A | 7/1985 | Hunt et al. |
| 4,755,388 A | 7/1988 | Heath et al. |
| 4,828,837 A | 5/1989 | Uster et al. |
| 4,925,661 A | 5/1990 | Huang |
| 4,954,345 A | 9/1990 | Muller |
| 4,957,735 A | 9/1990 | Huang |
| 5,043,164 A | 8/1991 | Huang et al. |
| 5,064,655 A | 11/1991 | Uster et al. |
| 5,077,211 A | 12/1991 | Yarosh |
| 5,223,409 A | 6/1993 | Ladner et al. |
| 5,264,618 A | 11/1993 | Felgner et al. |
| 5,403,484 A | 4/1995 | Ladner et al. |
| 5,491,069 A | 2/1996 | Dirmi et al. |
| 5,571,698 A | 11/1996 | Ladner et al. |
| 5,888,764 A | 3/1999 | Mountz et al. |
| 6,492,389 B1 | 12/2002 | Huang et al. |
| 6,566,495 B1 | 5/2003 | Fodor et al. |
| 6,572,876 B2 | 6/2003 | Waggle et al. |
| 7,576,209 B2 | 8/2009 | Kelly et al. |
| 7,939,313 B2 | 5/2011 | Heyduk et al. |
| 8,232,273 B2 | 7/2012 | Baell et al. |
| 10,071,087 B2 | 9/2018 | Zheng et al. |
| 10,758,524 B2 | 9/2020 | Zheng et al. |
| 11,331,328 B2 | 5/2022 | Zhou et al. |
| 2005/0084876 A1 | 4/2005 | Tschopp et al. |
| 2005/0208151 A1 | 9/2005 | Hurez et al. |
| 2006/0140959 A1 | 6/2006 | Fisher et al. |
| 2007/0072860 A1 | 3/2007 | Bruncko et al. |
| 2008/0171051 A1 | 7/2008 | Johnston et al. |
| 2009/0312373 A1 | 12/2009 | Lee et al. |
| 2010/0086941 A1 | 4/2010 | Adami et al. |
| 2010/0093613 A1 | 4/2010 | Kunkel |
| 2010/0310504 A1 | 12/2010 | Lowe et al. |
| 2011/0028387 A1 | 2/2011 | Garcia et al. |
| 2011/0053938 A1 | 3/2011 | Foley et al. |
| 2011/0086860 A1 | 4/2011 | Kimura et al. |
| 2012/0059004 A1 | 3/2012 | Elliott et al. |
| 2012/0156134 A1 | 6/2012 | Squires |
| 2012/0157455 A1 | 6/2012 | Foley et al. |
| 2013/0195884 A1 | 8/2013 | Boutros et al. |
| 2013/0237539 A1 | 9/2013 | Foley et al. |
| 2014/0005190 A1 | 1/2014 | Baell et al. |
| 2014/0024639 A1 | 1/2014 | Adams et al. |
| 2014/0199234 A1 | 7/2014 | Wang et al. |
| 2014/0356322 A1 | 12/2014 | Crews et al. |
| 2015/0291562 A1 | 10/2015 | Crew et al. |
| 2016/0095850 A1 | 4/2016 | Cooper et al. |

(Continued)

FOREIGN PATENT DOCUMENTS

| | | |
|---|---|---|
| CN | 101774875 A | 7/2010 |
| CN | 101939008 A | 1/2011 |

(Continued)

OTHER PUBLICATIONS

Adams, D. et al., "Synthesis, cellular evaluation, and mechanism of action of piperlongumine analogs, " PNAS, Sep. 18, 2012, pp. 15115-15120, vol. 109, No. 38.
Aguilar, A., et al., "A Potent and Highly Efficacious Bcl-2/Bcl-xL Inhibitor," J. Med. Chem., 2013, pp. 3048-3067, vol. 56.
Arnold, A. et al., "Preclinical studies of Apogossypolone: a new nonpeptidic pan small-molecule inhibitor of Bcl-2, Bcl-XL and Mcl-I proteins in Follicular Small Cleaved Cell Lymphoma model," Mol. Cancer, 2008, pp. 1-10, vol. 7, No. 20.
Baar, M et al., "Targeted Apoptosis of Senescent Cells Restores Tissue Homeostasis in Response to Chemotoxicity and Aging," HHS Public Access Author Manuscript, Mar. 23, 2018, pp. 1-37, published in final edited form as: Cell, Mar. 23, 2017, pp. 132-147, vol. 169, No. 1.

(Continued)

*Primary Examiner* — Raymond J Henley, III
(74) *Attorney, Agent, or Firm* — POLSINELLI PC

(57) ABSTRACT

The present disclosure provides compositions and methods for selectively killing senescent cells, wherein the composition comprises piperlongumine derivative thereof. The selective killing of senescent cells may delay aging and/or treat age-related disorders.

17 Claims, 11 Drawing Sheets

(56) References Cited

U.S. PATENT DOCUMENTS

| | | | |
|---|---|---|---|
| 2016/0176916 | A1 | 6/2016 | Bradner et al. |
| 2016/0339019 | A1 | 11/2016 | Laberge et al. |
| 2017/0056421 | A1 | 3/2017 | Zhou et al. |
| 2017/0246155 | A1 | 8/2017 | Zheng et al. |
| 2017/0348307 | A1 | 12/2017 | Aberge et al. |
| 2018/0002431 | A1 | 1/2018 | Zhou et al. |
| 2018/0021323 | A1 | 1/2018 | Zhou et al. |
| 2018/0369223 | A1 | 12/2018 | Zheng et al. |
| 2019/0054097 | A1 | 2/2019 | Zhou et al. |
| 2019/0135801 | A1 | 5/2019 | Zheng et al. |

FOREIGN PATENT DOCUMENTS

| | | | |
|---|---|---|---|
| CN | 102125552 | A | 7/2011 |
| CN | 102146054 | A | 8/2011 |
| CN | 103601670 | A | 2/2014 |
| CN | 105085620 | A | 11/2015 |
| EP | 0532767 | A1 | 3/1993 |
| EP | 2985285 | A1 | 2/2016 |
| JP | 11349568 | A | 12/1999 |
| NO | 2009114126 | A1 | 9/2009 |
| WO | 2002026940 | A1 | 4/2002 |
| WO | 2002097053 | A2 | 12/2002 |
| WO | 2004106328 | A1 | 12/2004 |
| WO | 2006023778 | A2 | 3/2006 |
| WO | 2008119741 | A2 | 10/2008 |
| WO | 2009129317 | A1 | 10/2009 |
| WO | 2009155386 | A1 | 12/2009 |
| WO | 2010080503 | A1 | 7/2010 |
| WO | 2010120943 | A1 | 10/2010 |
| WO | 2010138588 | A2 | 12/2010 |
| WO | 2011009861 | A1 | 1/2011 |
| WO | 2011130395 | A1 | 10/2011 |
| WO | 2012030408 | A1 | 3/2012 |
| WO | 2013083098 | A2 | 6/2013 |
| WO | 2013106643 | A2 | 7/2013 |
| WO | 2013178821 | A1 | 12/2013 |
| WO | 2014089124 | A1 | 6/2014 |
| WO | 2014108452 | A1 | 7/2014 |
| WO | 2014174511 | A1 | 10/2014 |
| WO | 2015116740 | A1 | 8/2015 |
| WO | 2015171591 | A1 | 11/2015 |
| WO | 2016014625 | A1 | 1/2016 |
| WO | 2016118855 | A1 | 7/2016 |
| WO | 2016118859 | A1 | 7/2016 |
| WO | 2017012774 | A1 | 1/2017 |
| WO | 2017101851 | A1 | 6/2017 |
| WO | 2017184995 | A1 | 10/2017 |
| WO | 2019221755 | A1 | 11/2019 |

OTHER PUBLICATIONS

Bai, L., et al., "BM-1197: A Novel and Specific Bcl-2/Bcl-xL Inhibitor Inducing Complete and Long-Lasting Tumor Regression In Vivo," PLOS One, Jun. 2014, pp. 1-13, vol. 9, No. 6, e99404.
Bajwa, N., et al., "Inhibitors of the anti-apoptotic Bcl-2 proteins: a patent review," NIH Public Access Author Manuscript, Jan. 17, 2013, pp. 1-25, published in final edited form as: Expert Opin. Ther. Pat., Jan. 2012, pp. 37-55, vol. 22, No. 1.
Baker, D et al., "Clearance of p16Ink4a-positive senescent cells delays ageing-associated disorders," Nature, Nov. 10, 2011, pp. 232-236, vol. 479, No. 7372, Macmillian Publishers Limited.
Baker, D. et al., "Naturally occurring p16Ink4a-positive cells shorten healthy lifespan," HHS Public Access Author Manuscript, Aug. 3, 2016, pp. 1-30, published in final edited form as: Nature, Feb. 11, 2016, pp. 184-189, vol. 530, No. 7589.
Banerjee, T. et al., "The crystal and molecular structure of N-(3,4,5-trimethoxycinnamoyl)-A3-piperidine-2-one, an amide alkaloid (piperlongumine), C17H19NO5," Can. J. Chem., 1986, pp. 876-880, vol. 64.
Baritaki, S. et al., "Chemotherapeutic drugs sensitize cancer cells to Trail-mediated apoptosis: up-regulation of DR5 and inhibition of Yin Yang 1," Mol. Cancer Ther., Apr. 2007, pp. 1387-1399, vol. 6, No. 4.
Barton, K. et al., "Selective HDAC Inhibition for the Disruption of Latent HIV-1 Infection," PLOS One, Aug. 2014, pp. 1-11, vol. 9, No. 8, e102684.
Beerman, I. et al., "Stem cells and the aging hematopoietic system," Curr. Opin. Immunol., 2010, pp. 500-506, vol. 22.
Bensoussan, C. et al., "Iron-catalyzed cross-coupling between C-bromo mannopyranoside derivatives and a vinyl Grignard reagent: toward the synthesis of the C31-C52 fragment of amphidinol 3," Tetrahedron, 2013, pp. 7759-7770, vol. 69, No. 36, Elsevier Ltd.
Berg, C. et al., "Human mature red blood cells express caspase-3 and caspase-8, but are devoid of mitochondrial regulators of apoptosis," Cell Death and Differentiation, 2001, pp. 1197-1206, vol. 8.
Bezerra, D. et al., "Overview of the therapeutic potential of piplartine (piperlongumine)," Eur. J. Pharma. Sci., 2013, pp. 453-463, vol. 48, No. 3, Elsevier B.V., Amsterdam.
Bhutani, J. et al., "Akt inhibitors: mechanism of action and implications for anticancer therapeutics," Infectious Agents and Cancer, 2013, pp. 1-4, vol. 8, No. 49.
Blagosklonny, M., "Selective anti-cancer agents as anti-aging drugs," Cancer Biol. Ther., Dec. 2013, pp. 1092-1097, vol. 14, No. 12, Landes Bioscience.
Bokesch, H. et al., "A New Hypoxia Inducible Factor-2 Inhibitory Pyrrolinone Alkaloid from Roots and Stems of Piper sarmentosum," Chem. Pharm. Bull., 2011, pp. 1178-1179, vol. 59, No. 9, Pharmaceutical Society of Japan.
Braun, H. et al., "Cellular Senescence Limits Regenerative Capacity and Allograft Survival," J. Am. Soc. Nephrol., Sep. 2012, pp. 1467-1473, vol. 23, No. 9.
Brenkman, A. et al., "Mdm2 Induces Mono-Ubiquitination of FOXO4," PLOS One, Jul. 2008, pp. 1-7, vol. 3, No. 7, e2819.
Bruncko, M., et al., "Studies Leading to Potent, Dual Inhibitors of Bcl-2 and Bcl-xL," J. Med. Chem., 2007, pp. 641-662, vol. 50, No. 4.
Bruncko, M., et al., "Structure-Guided Design of a Series of MCL-1 Inhibitors with High Affinity and Selectivity," J. Med. Chem., 2015, pp. 2180-2194, vol. 58, No. 5.
Bucknall, M. et al., "Practical Quantitative Biomedical Applications of MALDI-TOF Mass Spectrometry," J. Am. Soc. Mass. Spectrom., 2002, pp. 1015-1027, vol. 13, Elsevier Science Inc.
Burd, C. et al., "Monitoring tumorigenesis and senescence in vivo with a p16(INK4a)-luciferase model," Cell, 2013, pp. 340-351, vol. 152.
Campisi, J. et al., "Senescent Cells, Tumor Suppression, and Organismal Aging: Good Citizens, Bad Neighbors," Cell, Feb. 25, 2005, pp. 513-522, vol. 120, Elsevier Inc.
Campisi, J., "Cellular senescence: putting the paradoxes in perspective," Curr. Opin. Genet. Dev., 2011, pp. 107-112, vol. 21, Elsevier.
Campisi, J., "Aging, cellular senescence, and cancer," Annu. Rev. Physiol., 2013, pp. 685-705, vol. 75.
Carell, T. et al., "A Solution-Phase Screening Procedure for the Isolation of Active Compounds from a Library of Molecules," Angew. Chem. Int. Ed. Engl., 1994, pp. 2059-2061, vol. 33, No. 20.
Caserta, T. et al., "Q-VD-OPh, a broad spectrum caspase inhibitor with potent antiapoptotic properties," Apoptosis, 2003, pp. 345-352, vol. 8.
Chang, J. et al., "Clearance of senescent cells by ABT263 rejuvenates aged hematopoietic stem cells in mice," Nat. Med., Jan. 2016, pp. 78-83, vol. 22, No. 1.
Chatterjee, A. et al., "Alkaloids of Piper Longum Linn-I: Structure and Synthesis of Piperlongumine and Piperlonguminine," Tetrahedron, 1967, pp. 1769-1781, vol. 23, No. 4, Pergamon Press, Northern Ireland.
Chen, Q. et al., "Apo2L/TRAIL and Bcl-2-related proteins regulate type I interferon-induced apoptosis in multiple myeloma," Blood, Oct. 1, 2001, pp. 2183-2192, vol. 98, No. 7.
Chen, L. et al., "p53 alpha-Helix mimetics antagonize p53/MDM2 interaction and activate p53," Mol. Cancer Ther., Jun. 2005, pp. 1019-1025, vol. 4, No. 6.
Chen, S. et al., "Celecoxib Promotes c-FLIP Degradation through Akt-Independent Inhibition of GSK3," Cancer Res., 2011, pp. 6270-6281, vol. 71, No. 19.

(56) References Cited

OTHER PUBLICATIONS

Chen, J. et al., "The Bcl-2/Bcl-XL/Bcl-w Inhibitor, Navitoclax, Enchances the Activity of Chemotherapeutic Agents In Vitro and In Vivo," Mol. Cancer Ther., 2011, pp. 2340-2349, vol. 10, No. 12.
Chen, J. et al., "Structure-Based Discovery of BM-957 as a Potent Small-Molecule Inhibitor of Bcl-2 and Bcl-xL Capable of Achieving Complete Tumor Regression," NIH Public Access Author Manuscript, Oct. 11, 2013, pp. 1-33, published in final edited form as: J. Med. Chem., Oct. 11, 2012, pp. 8502-8514, vol. 55, No. 19.
Childs, B. et al., "Senescence and apoptosis: dueling or complementary cell fates?," EMBO Rep., 2014, pp. 1139-1153, vol. 15.
Childs, B. et al., "Senescent cells: an emerging target for diseases of ageing," HHS Public Access Author Manuscript, May 9, 2018, pp. 1-41, published in final edited form as: Nat. Rev. Drug Discov., Oct. 2017, pp. 718-735, vol. 16, No. 10.
Cho, C. et al., "An Unnatural Biopolymer," Sci., Sep. 3, 1993, pp. 1303-1305, vol. 261.
Citrin, D. et al., "Role of type II pneumocyte senescence in radiation-induced lung fibrosis," J. Natl. Can. Inst., 2013, pp. 1474-1484, vol. 105.
Cohen, J. et al., "Astrocyte Senescence and Metabolic Changes in Response to HIV Antiretroviral Therapy Drugs," Front. Aging Neurosci., Aug. 2017, vol. 9, No. 281.
Communication under Rule 71(e) EPC (Notice of Allowance) dated Jul. 15, 2019 from related European Patent Application No. 15789264.7; 7 pgs.
Coppe, J. et al., "The senescence-associated secretory phenotype: the dark side of tumor suppression," Annu. Rev. Pathol., 2010, pp. 99-118, vol. 5.
Cory, S. et al., "The Bcl2 family: regulators of the cellular life-or-death switch," Nat. Rev. Can., 2002, pp. 647-656, vol. 2.
Cull, M. et al., "Screening for receptor ligands using large libraries of peptides linked to the C terminus of the lac repressor," PNAS, Mar. 1992, pp. 1865-1869, vol. 89.
Cwirla, S. et al., "Peptides on phage: A vast library of peptides for identifying ligands, " PNAS, Aug. 1990, pp. 6378-6382, vol. 87.
Czabotar, P. et al., "Control of apoptosis by the BCL-2 protein family: implications for physiology and therapy," Nat. Rev. Mol. Cell Biol., 2014, pp. 49-63, vol. 15.
Debacq-Chainiaux, F. et al., "Protocols to detect senescence-associated beta-galactosidase (SA-betagal) activity, a biomarker of senescent cells in culture and in vivo," Nat. Protoc., 2009, pp. 1798-1806, vol. 4.
Demaria, M. et al., "An Essential Role for Senescent Cells in Optimal Wound Healing through Secretion of PDGF-AA," Dev. Cell, 2014, pp. 722-733, vol. 31.
Delbridge, A. et al., "Thirty years of BCL-2: translating cell death discoveries into novel cancer therapies," Nat. Rev. Cancer, Feb. 2016, pp. 99-109- vol. 16.
Park, B-S., et al., "Antiplatelet Activities of Newly Synthesized Derivatives of Piperlongumine," Phytother. Res., Sep. 2008, pp. 1195-1199, vol. 22, No. 9.
Lu, Y. et al., "Discovery of a Nanomolar Inhibitor of the Human Murine Double Minute 2 (MDM2)-p53 Interaction through an Integrated, Virtual Database Screening Strategy," J. Med. Chem., 2006, pp. 3759-3762, vol. 49, No. 13.
Lu, J., et al., "Hijacking the E3 Ubiquitin Ligase Cereblon to Efficiently Target BRD4," Chem. Biol., Jun. 18, 2015, pp. 755-763, vol. 22.
Marcotte, R. et al., "Replicative senescence revisited," J. Gerontol. A Biol. Sci. Med. Sci., 2002, pp. B257-B269, vol. 57.
Mason, K. et al., "Programmed Anuclear Cell Death Delimits Platelet Life Span," Cell, Mar. 2007, pp. 1173-1186, vol. 128.
Matthews, C. et al., "Vascular Smooth Muscle Cells Undergo Telomere-Based Senescence in Human Atherosclerosis. Effects of Telomerase and Oxidative Stress," Cir. Res., Jul. 21, 2006, pp. 156-164, vol. 99.

Mawji, I. et al., "A Chemical Screen Identifies Anisomycin as an Anoikis Sensitizer That Functions by Decreasing FLIP Protein Synthesis," Cancer Res., Sep. 1, 2007, pp. 8307-8315, vol. 67, No. 17.
Meng, A. et al,. "Sphingomyelin synthase as a potential target for D609-induced apoptosis in U937 human monocytic leukemia cells," Exp. Cell Res., 2004, pp. 385-392, vol. 292.
Mercurio, L. et al., "Intracellular Insulin-like growth factor binding protein 2 (IGFBP2) contributes to the senescence of keratinocytes in psoriasis by stabilizing cytoplasmic p21," Aging, 2020, pp. 6823-6851, vol. 12, No. 8.
Mirgorodskaya, E. et al., "Characterization of Protein Glycosylation by MALDI-TOFMS," Meth. Mol. Biol., 2000, pp. 273-292, vol. 146, Humana Press Inc.
Mohammad, R. et al., "Preclinical Studies of TW-37, a New Nonpeptidic Small-Molecule Inhibitor of Bcl-2, in Diffuse Large Cell Lymphoma Xenograft Model Reveal Drug Action on Both Bcl-2 and Mcl-1," Clin. Cancer Res., 2007, pp. 2226-2235, vol. 13, No. 7.
Munoz-Espin, D et al., "Cellular senescence: from physiology to pathology," Nat. Rev. Mol. Cell Biol., 2014, pp. 182-496, vol. 15.
Nopora, A. et al., "Bcl-2 Controls Dendritic Cell Longevity In Vivo," J. Immunol., Sep. 2002, pp. 3006-3014, vol. 169, No. 6.
Notice of Allowance dated May 8, 2018 from related U.S. Appl. No. 15/328,368; 5 pgs.
Notice of Allowance dated Apr. 30, 2020 from related U.S. Appl. No. 16/057,021; 5 pgs.
Notice of Allowance dated May 7, 2021 from related Chinese Patent Application No. 201580035221.5; 4 pgs.
Notice of Allowance dated Jan. 13, 2022 from related U.S. Appl. No. 15/308,552; 9 pgs.
Office Action dated Oct. 23, 2017 from related U.S. Appl. No. 15/328,368; 8 pgs.
Office Action dated Feb. 27, 2018 from related U.S. Appl. No. 15/328,368; 6 pgs.
Office Action dated Oct. 4, 2018 from related U.S. Appl. No. 15/545,480; 4 pgs.
Office Action dated Oct. 4, 2018 from related U.S. Appl. No. 15/308,552; 16 pgs.
Office Action dated Apr. 17, 2019 from related U.S. Appl. No. 15/545,480; 15 pgs.
Office Action dated May 29, 2019 from related U.S. Appl. No. 15/308,552 17 pgs.
Office Action dated Jun. 11, 2019 from related European Patent Application No. 15789264.7; 4 pgs.
Office Action dated Jun. 26, 2019 from related U.S. Appl. No. 16/057,021; 10 pgs.
Office Action dated Sep. 3, 2019 from related Chinese Patent Application No. 201580035221.5; 91 pgs.
Office Action dated Oct. 16, 2019 from related U.S. Appl. No. 15/545,480; 15 pgs.
Office Action dated Nov. 13, 2019 from related U.S. Appl. No. 16/057,021; 6 pgs.
Office Action dated Feb. 25, 2020 from related U.S. Appl. No. 16/057,021; 5 pgs.
Office Action dated Mar. 2, 2020 from related U.S. Appl. No. 15/545,480; 10 pgs.
Office Action dated Mar. 20, 2020 from related U.S. Appl. No. 15/308,552; 22 pgs.
Office Action dated Aug. 11, 2020 from related U.S. Appl. No. 15/545,480; 11 pgs.
Office Action dated Sep. 1, 2020 from related Chinese Patent Application No. 201580035221.5; 10 pgs., with English translation.
Office Action dated Oct. 29, 2020 from related U.S. Appl. No. 15/308,552; 7 pgs.
Office Action dated Dec. 28, 2020 from related U.S. Appl. No. 15/545,480; 16 pgs.
Office Action dated Jan. 5, 2021 from related Chinese Patent Application No. 201580035221.5; 10 pgs.
Office Action dated May 12, 2021 from related U.S. Appl. No. 15/308,552; 15 pgs.
Office Action dated Jun. 1, 2021 from related U.S. Appl. No. 15/545,480; 15 pgs.

(56) References Cited

OTHER PUBLICATIONS

Omori, S et al., "Generation of a p16 Reporter Mouse and Its Use to Characterize and Target p16high Cells In Vivo," Cell Metab., Nov. 3, 2020, pp. 814-828, vol. 32.
Park, C-M. et al., "Discovery of an Orally Bioavailable Small Molecule Inhibitor of Prosurvival B-Cell Lymphoma 2 Proteins," J. Med. Chem., 2008, pp. 6902-6915, vol. 51, No. 21.
Pelz, N. et al., "Discovery of 2-Indole-acylsulfonamide Myeloid Cell Leukemia 1 (Mcl-1) Inhibitors Using Fragment-Based Methods," J. Med. Chem., 2016, pp. 2054-2066, vol. 59.
Raj, L. et al., "Selective killing of cancer cells by a small molecule targeting the stress response to ROS," Nature, Jul. 14, 2011, pp. 231-234, vol. 475, Macmillan Publishers Limited.
Raja, S. et al., "The natural product honokiol preferentially inhibits cellular FLICE-inhibitory protein and augments death receptor-induced apoptosis," Mol. Cancer Ther., 2008, pp. 2212-2223, vol. 7, No. 7.
Rao, V. et al., "Synthesis and biological evaluation of new piplartine analogues as potent aldose reductase inhibitors (ARIs)," Eur. J. Med. Chem., 2012, pp. 344-361, vol. 57, Elsevier Masson SAS.
Reid, J. et al., "Mouse pharmacokinetics and metabolism of the curcumin analog, 4-piperidinone,3,5-bis[)2-fluorophenyl)methylene]-acetate(3E,5E) (EF-24; Nsc 716993)," Cancer Chemother. Pharmacol., 2014, pp. 1137-1146, vol. 73.
Ricci, M. et al., "Chemotherapeutic Approaches for Targeting Cell Death Pathways," The Oncologist, 2006, pp. 342-357, vol. 11.
Richardson, R., "Ionizing radiation and aging: rejuvenating an old idea," Aging, 2009, pp. 887-902, vol. 1.
Robak, T., "BCL-2 inhibitors for Chronic Lymphocytic Leukemia," J. Leuk., 2015, pp. 1-3, vol. 3, No. 3, 1000e114.
Rockett, J. et al., "DNA arrays: technology, options and toxicological applications," Xenobiotica, 2000, pp. 155-177, vol. 30, No. 2.
Rodier, F. et al., "Four faces of cellular senescence," J. Cell Biol., Feb. 14, 2011, pp. 547-556, vol. 192, The Rockefeller University Press.
Rudin, C. et al., "Phase II Study of Single-Agent Navitoclax (ABT-263) and Biomarker Correlates in Patients with Relapsed Small Cell Lung Cancer," Clin. Cancer Res., Jun. 2012, pp. 3163-3169, vol. 18, No. 11.
Zhu, Y. et al., Identification of a novel senolytic agent, navitoclax, targeting the Bcl-2 family of anti-apoptotic factors, Aging Cell, Jun. 2016, pp. 428-435, vol. 15, No. 3.
Zuckermann, R. et al., "Discovery of Nanomolar Ligands for 7-Transmembrane G-Protein-Coupled Receptors from a Diverse N-(Substituted)glycine Peptoid Library," J. Med. Chem., 1994, pp. 2678-2685, vol. 37.
Safa, A. et al., "Targeting the Anti-Apoptotic Protein c-FLIP for Cancer Therapy," Cancers, 2011, pp. 1639-1671, vol. 3.
Sanders, Y. et al., "Histone Modifications in Senescence-Associated Resistance to Apoptosis by Oxidative Stress," Redox Biol., 2013, pp. 8-16, vol. 1, Elsevier B.V.
Scanbur Research Models & Services, 2019, 110 pgs., retrieve from: https://www.scanbur.com/Files/Images/Research/RMS-SCB-2019-WEB.pdf.
Schafer, M. et al., "Targeting Senescent Cells in Fibrosis: Pathology, Paradox, and Practical Considerations," Curr. Rheumatol. Rep., Jan. 26, 2018, pp. 1-11, vol. 20, No. 3, Springer.
Schimmer, A. et al., "Identification of Small Molecules that Sensitize Resistant Tumor Cells to Tumor Necrosis Factor-Family Death Receptors," Cancer Res., 2006, pp. 2367-2375, vol. 66, No. 4.
Scott, J. et al., "Searching for Peptide Ligands with an Epitope Library," Sci., Jul. 27, 1990, pp. 386-390, vol. 249, No. 4967.
Seo, Y. et al., "Synthesis and biological evaluation of piperlongumine derivatives as potent anti-inflammatory agents," Bioorg. Med. Chem. Lett., Dec. 15, 2014, pp. 5727-5730, vol. 24, No. 24, Elsevier Ltd.
Serrano, M. et al., "Oncogenic ras provokes premature cell senescence associated with accumulation of p53 and p16INK4a," Cell, 1997, pp. 593-602, vol. 88.
Serrano, M. et al., "Putting the stress on senescence," Curr. Opin. Cell Biol., 2001, pp. 748-753, vol. 13.
Shao, L. et al., "Total body irradiation causes long-term mouse BM injury via induction of HSC premature senescence in an Ink4a- and Arf-independent manner," Blood, 2014, pp. 3105-3115, vol. 123.
Shao, L. et al., "Hematopoietic stem cell injury induced by ionizing radiation," Antioxid. Redox Signal., 2014, pp. 1447-1462, vol. 20.
Shirley, S. et al., "Targeting c-FLIP in cancer," Cancer Lett., 2013, pp. 141-150, vol. 332, No. 2, Elsevier Ireland Ltd.
Siegelin, M. et al., "Genistein enhances proteasomal degradation of the short isoform of FLIP in malignant glioma cells and thereby augments TRAIL-mediated apoptosis," Neurosci. Lett., Apr. 3, 2009, pp. 92-97, vol. 453, No. 2, Elsevier Ireland Ltd.
Sleebs, B. et al., "Quinazoline Sulfonamides as Dual Binders of the Proteins B-Cell Lymphoma 2 and B-Cell Lymphoma Extra Long with Potent Proapoptotic Cell-Based Activity," J. Med. Chem., 2011, pp. 1914-1926, vol. 54, No. 6.
Sleebs, B. et al., "Discovery of Potent and Selective Benzothiazole Hydrazone Inhibitors of Bcl-XL," J. Med. Chem., 2013, pp. 5514-5540, vol. 56, No. 13.
Son, D. et al., Piperlongumine inhibits atherosclerotic plaque formation and vascular smooth muscle cell proliferation by suppressing PDGF receptor signaling, Biochem. Biophys. Res. Commun., 2012, pp. 349-354, vol. 427.
Sorrentino, J. et al., "p16INK4a reporter mice reveal age-promoting effects of environmental toxicants," J. Clin. Invest., 2014, pp. 169-173, vol. 124.
Souers, A. et al., "ABT-199, a potent and selective BCL-2 inhibitor, achieves antitumor activity while sparing platelets," Nat. Med., 2013, pp. 202-208, vol. 19.
Stoll, R. et al., "Chalcone Derivatives Antagonize Interactions between the Human Oncoprotein MDM2 and p53," Biochem., 2001, pp. 336-344, vol. 40.
Swift, S. et al., "Acute Toxicity of Subcutaneously Administered Vitamin E Isomers Delta- and Gamma-Tocotrienol in Mice," Int. J. Toxicol., 2014, pp. 450-458, vol. 44, No. 6.
Tampe, D. et al., "Potential approaches to reverse or repair renal fibrosis," Nat. Rev. Nephrol., Apr. 2014, pp. 226-237, vol. 10.
Tanaka, Y. et al., "Discovery of Potent Mcl-1/Bcl-xL Dual Inhibitors by Using a Hybridization Strategy Based on Structural Analysis of Target Proteins," J. Med. Chem., 2013, pp. 9635-9645, vol. 56, No. 23.
Tang, G. et al., "Pyrogallol Based Molecules as Potent Inhibitors of the Anti-Apoptotic Bcl-2 Proteins," NIH Public Access Author Manuscript, 2008, pp. 1-12, published in final edited form as: J. Med. Chem., 2007, pp. 1723-1726, vol. 50, No. 8.
Tao, Z-F. et al., "Discovery of a Potent and Selective BCL-XL Inhibitor with in Vivo Activity," ACS Med. Chem. Lett., 2014, pp. 1088-1093, vol. 5.
Tchkonia, T. et al., "Cellular senescence and the senescent secretory phenotype: therapeutic opportunities," J. Clin. Invest., 2013, pp. 966-972, vol. 123.
Tse, C. et al., "ABT-263: a potent and orally bioavailable Bcl-2 family inhibitor," Can. Res., 2008, pp. 3421-3428, vol. 68.
Valentijn, F. et al., "Cellular senescence in the aging and diseased kidney," J. Cell Commun. Signal., 2018, pp. 69-82, vol. 12, Springer.
Van Deursen, J., "The role of senescent cells in ageing," Nature, 2014, pp. 439-446, vol. 509.
Van Willigenburg, H. et al., "Cellular senescence as a therapeutic target to improve renal transplantation outcome," Pharmacol. Res., Apr. 2018, pp. 322-330, vol. 130.
Vogler, M. et al., "Bcl-2 inhibitors: small molecules with a big impact on cancer therapy," Cell Death Differ., 2009, pp. 360-367, vol. 16.
Vogler, M., Targeting BCL2-Proteins for the Treatment of Solid Tumours, Adv. Med., 2014, pp. 1-14, Article ID 943648, Hindawi Publishing Corporation.
Wang, E., "Senescent Human Fibroblasts Resist Programmed Cell Death, and Failure to Suppress bcl2 Is Involved," Cancer Res., Jun. 1, 1995, pp. 2284-2292, vol. 55.
Wang, Y. et al., "Inhibition of phosphatidylinostol 3-kinase uncouples H2O2-induced senescent phenotype and cell cycle arrest in normal human diploid fibroblasts," Exp. Cell Res., 2004, pp. 188-196, vol. 298, Elsvier Inc.

(56) References Cited

OTHER PUBLICATIONS

Wang, Y. et al., "Total body irradiation selectively induces murine hematopoietic stem cell senescence," Blood, Jan. 1, 2006, pp. 358-366, vol. 107, No. 1.
Wang, Y. et al., "Total body irradiation causes residual bone marrow injury by induction of persistent oxidative stress in murine hematopoietic stem cells," Free Rad. Biol. Med., 2010, pp. 348-356, vol. 48, Elsevier Inc.
Wang, Y. et al., "Microrna Regulation of Ionizing Radiation-Induced Premature Senescence," Int. J. Radiation Oncology Biol. Phys., 2011, pp. 839-848, vol. 81, No. 3, Elsevier Inc.
Wang, B. et al., "The Bcl-2/xL inhibitor ABT-263 increases the stability of Mcl-1 mRNA and protein in hepatocellular carcinoma cells," Molecular Cancer, 2014, pp. 1-11, vol. 13, No. 98.
Waring, P. et al., "Cell death induced by the Fas/Fas ligand pathway and its role in pathology," Immunology and Cell Biology, 1999, pp. 312-317, vol. 77.
Warner, H. et al., "What Does Cell Death Have to Do With Aging?," J. Am. Geriatric Soc., 1997, pp. 1140-1146, vol. 45, No. 9.
Wood, T. et al., "Selective Inhibition of Histone Deacetylases Sensitizes Malignant Cells to Death Receptor Ligands," Mol. Cancer Ther., Jan. 2010, pp. 246-256, vol. 9, No. 1.
Wu, Y. et al., "Design, synthesis and biological activity of piperlongumine derivatives as selective anticancer agents," Eur. J. Med. Chem., 2014, pp. 545-551, vol. 82, Elsevier Masson SAS.
Yadav, V. et al., "Remediation of Hemorrhagic Shock-Induced Intestinal Barrier Dysfunction by Treatment with Diphenyldihaloketones EF24 and CLEFMA," J. Pharmacol. Exp. Ther., Nov. 2014, pp. 413-422, vol. 351.
Yang, C. et al., "The Curcumin Analog EF24 Targets NF-kB and miRNA-21, and Has Potent Anticancer Activity In Vitro and In Vivo," PLOS One, Aug. 2013, pp. 1-12, vol. 8, No. 8, e71130.
Yao, L. et al., "Piperlongumine alleviates lupus nephritis in MRL-Fas(lpr) mice by regulating the frequency of Th17 and regulatory T cells," Immunol. Lett., Sep. 2014, pp. 76-80, vol. 161, No. 1, Abstract Only.
Yin, H. et al., "Terphenyl-Based Helical Mimetics That Disurpt the p53/HDM2 Interaction," Angew. Chem. Int. Ed., Apr. 2005, pp. 2704-2707, vol. 44, No. 18, Wiley-VCH Verlag Gmbh & Co. KGaA, Weinheim.
Yu, C. et al., "HIV and drug abuse mediate astrocyte senescence in a beta-catenin-dependent manner leading to neuronal toxicity," Aging Cell, 2017, pp. 956-965, vol. 16.
Zengerle, M. et al., "Selective Small Molecule Induced Degradation of the BET Bromodomain Protein BRD4," ACS Chem. Biol., 2015, pp. 1770-1777, vol. 10, American Chemical Society.
Zhou, H. et al., "Design of Bcl-2 and Bcl-xL Inhibitors with Subnanomolar Binding Affinities Based Upon a New Scaffold," NIH Public Access Author Manuscript, May 24, 2013, pp. 1-42, published in final edited form as: J. Med. Chem., May 24, 2012, pp. 4664-4682, vol. 55, No. 10.
Zhou, H. et al., "Structure-based Design of Potent Bcl-2/Bcl-xL Inhibitors with Strong in vivo Antitumor Activity," NIH Public Access Author Manuscript, Jul. 12, 2013, pp. 1-31, published in final edited form as: J. Med. Chem., Jul. 12, 2012, pp. 6149-6161, vol. 55, No. 13.
Zhu, Y. et al., "The Achilles' heel of senescent cells: from transcriptome to senolytic drugs," Aging Cell, Aug. 2015, pp. 644-658, vol. 14, No. 4.
Desai, S. et al., "Early Immune Senescence in HIV Disease," Curr. HIV/AIDS Rep., 2010, pp. 4-10, vol. 7.
Devlin, J. et al., "Random Peptide Libraries: A Source of Specific Protein Binding Molecules," Sci., Jul. 27, 1990, pp. 404-406, vol. 249, No. 4967, American Association for Advancement of Science.
Dewitt, S. et al., "'Diversomers': An approach to nonpeptide, nonoligomeric chemical diversity," PNAS, Aug. 1993, pp. 6909-6913, vol. 90.
Di Pietro, R. et al., "Ionnizing radition sensitizes erythroleukemic cells but not normal erythroblasts to tumor necrosis factor-related apoptosis-inducing ligand (TRAIL)-mediated cytotoxicity by selective up-regulation of TRAIL-R1," Blood, May 1, 2001, pp. 2596-2603, vol. 97, No. 9.
Dodson, C. et al., "Cenocladamide, a dihydropyridone alkaloid from Piper cenocladum," Phytochemistry, 2000, pp. 51-54, vol. 53, Elsevier Science Ltd.
Duh, C. et al., "Cytotoxic Pyridone Alkaloids From the Leaves of Piper Aborescens," J. Nat. Prod., Nov.-Dec. 1990, pp. 1575-1577, vol. 53, No. 6.
Dykstra, B. et al., "Clonal analysis reveals multiple functional defects of aged murine hematopoietic stem cells," J. Exp. Med., 2011, pp. 2691-2703, vol. 208.
Erb, E. et al., "Recursive deconvolution of combinatorial chemical libraries," PNAS, Nov. 1994, pp. 11422-11426, vol. 91.
Extended European Search Report dated Oct. 5, 2017 from related European Patent Application No. 15789264.7; 7 pgs.
Extended European Search Report dated Jan. 2, 2018 from related European Patent Application No. 15824181.0; 9 pgs.
Extended European Search Report dated Jul. 6, 2020 from related European Patent Application No. 19216987.8; 10 pgs.
Felici, F., "Selection of Antibody Ligands from a Large Library of Oligopeptides Expressed on a Multivalent Exposition Vector," J. Mol. Biol., 1991, pp. 301-310, vol. 222.
Fleenor, C. et al., "Ionizing radiation and hematopoietic malignancies: altering the adaptive landscape," Cell Cycle, 2010, pp. 3005-3011, vol. 9.
Fodor, S. et al., "Multiplexed biochemical assays with biological chips," Nature, 1993, pp. 555-556, vol. 364, No. 6437.
Fontenele, J. et al., "Antiplatelet effects of piplartine, an alkamide isolated from Piper tuberculatum: possible involvement of cyclooxygenase blockade and antioxidant activity," J. Pharm. Pharmacol., 2009, pp. 511-515, vol. 61, No. 4.
Galatin, P. et al., "A Nonpeptidic Sulfonamide Inhibits the p53-mdm2 Interaction and Activates p53-Dependent Transcription in mdm2-Overexpressing Cells," J. Med. Chem., 2004, pp. 4163-4165, vol. 47, No. 17.
Gallop, M. et al., "Applications of Combinatorial Technologies to Drug Discovery. 1. Background and Peptide Combinatorial Libraries," J. Med. Chem., Apr. 1994, pp. 1233-1251, vol. 37, No. 9.
Geiger, H. et al., "Regulation of hematopoietic stem cell aging in vivo by a distinct genetic element," PNAS, 2005, pp. 5102-5107, vol. 102.
Geiger, H. et al., "The ageing haematopoietic stem cell compartment," Nat. Rev. Immunol., 2013, pp. 376-389, vol. 13.
Gobom, J. et al., "Detection and Quantification of Neurotensin in Human Brain Tissue by Matrix-Asserted Laser Desorption/Ionization Time-of-Flight Mass Spectrometry," Anal. Chem., 2000, pp. 3320-3326, vol. 72.
Gottlieb, Y. et al., "Physiologically aged red blood cells undergo erythrophagocytosis in vivo but not in vitro," Haematologica, 2012, pp. 994-1002, vol. 97, No. 7.
Gustafson, J. et al., "Small-Molecule-Mediated Degradation of the Androgen Receptor through Hydrophobic Tagging," Angew. Chem. Int. Ed., Aug. 10, 2015, pp. 9659-9662, vol. 54, No. 33.
Harfouche, G. et al., "Response of normal stem cells to ionizing radiation: a balance between homeostasis and genomic stability," Mutat. Res., 2010, pp. 167-174, vol. 704.
He, J-H. et al., "Apogossypolone, a small-molecule inhibitor of Bcl-2, induces radiosensitization of nasopharyngeal carcinoma cells by stimulating autophagy," Int. J. Oncology, 2014, pp. 1099-1108, vol. 45.
Houghten, R. et al., "The Use of Synthetic Peptide Combinatorial Libraries for the Identification of Bioactive Peptides, " Biotechniques, 1991, pp. 412-421, vol. 13, No. 3.
International Search Report and Written Opinion dated Sep. 18, 2015 from related International Patent Application No. PCT/US2015/029208; 13 pgs.
International Search Report and Written Opinion dated Oct. 23, 2015 from related International Patent Application No. PCT/US2015/041470; 9 pgs.
International Search Report and Written Opinion dated Apr. 1, 2016 from related International Patent Application No. PCT/US2016/014518; 9 pgs.

(56) References Cited

OTHER PUBLICATIONS

International Search Report and Written Opinion dated Apr. 1, 2016 from related International Patent Application No. PCT/US2016/014510; 12 pgs.

International Search Report and Written Opinion dated Jul. 11, 2017 from related International Patent Application No. PCT/US2017/028875; 9 pgs.

International Search Report and Written Opinion dated Jun. 29, 2015 from related International Patent Application No. PCT/US2015/013387; 34 pgs.

International Search Report and Written Opinion dated Aug. 7, 2018 from related International Patent Application No. PCT/US2018/033479; 9 pgs.

International Search Report and Written Opinion dated Apr. 26, 2019 from related International Patent Application No. PCT/US2019/014545; 10 pgs.

Janzen, V. et al., "Stem-cell ageing modified by the cyclin-dependent kinase inhibitor p16INK4a," Nature, 2006, pp. 121-426, vol. 443.

Joshi, B. et al., "On the Structure of Piplartine and a Synthesis of Dihydropiplartine," Tetrahedron Lett., 1968, pp. 2395-2400, vol. 9, No. 20, Pergamon Press, Great Britain.

Jozefczuk, J. et al., "Preparation of Mouse Embryonic Fibroblast Cells Suitable for Culturing Human Embryonic and Induced Pluripotent Stem Cells," J. Vis. Exp., Jun. 2012, pp. 1-5, vol. 64, Issue e3854.

Kirkland, J. et al., "Clinical strategies and animal models for developing senolytic agents," Exp. Gastroenterol., 2015, pp. 19-25, vol. 68, Elsevier Inc.

Kubo, M. et al., "Evaluation of Constituents of Piper retrofractum Fruits on Neurotrophic Activity," J. Nat. Prod., 2013, pp. 769-773, vol. 76, No. 4, The American Chemical Society and American Society of Pharmacognosy.

Kumar, J. et al., "Synthesis, anticancer, and antibacterial activities of piplartine derivatives on cell cycle regulation and growth inhibition," Journal of Asian Natural Products Research, Jun. 1, 2013, pp. 658-669, vol. 15, No. 6, Taylor & Francis Group.

Laberge, R. et al., "Mitochondrial DNA damage induces apoptosis in senescent cells," Cell Death Dis., 2013, p. e727, vol. 4.

Lam, K. et al., "A new type of synthetic peptide library for identifying ligand-binding activity," Nature, Nov. 7, 1991, pp. 82-84, vol. 354.

Lam, K. "Mini-review. Application of combinatorial library methods in cancer research and drug discovery," Anti-Cancer Drug Des., 1997, pp. 145-167, vol. 12, No. 3.

Le, O. et al., "Ionizing radiation-induced long-term expression of senescence markers in mice is independent of p53 and immune status," Aging Cell, 2010, pp. 398-409, vol. 9.

Le Couteur, D. et al., "Aging biology and novel targets for drug discovery," J. Gerontol. A Biol. Sci. Med. Sci., 2012, pp. 168-174, vol. 67.

Lee, S-J. et al., "Berberine sensitizes TRAIL-induced apoptosis through proteasome-mediated downregulation of c-FLIP and Mcl-1 proteins," Int. J. Oncol., 2011, pp. 485-492, vol. 38.

Lessene, G., et al., "BCL-2 family antagonists for cancer therapy," Nat. Rev. Drug Discov., Dec. 2008, pp. 989-1000, vol. 7.

Lessene, G. et al., "Structure-guided design of a selective BCL-X(L) inhibitor," Nat. Chem. Biol., 2013, pp. 390-397, vol. 9.

Lin, C. et al., "Endostatin and transglutaminase 2 are involved in fibrosis of the aging kidney," HHS Public Access Author Manuscript, Jun. 1, 2017, pp. 1-20, published in final edited form as: Kidney Int., Jun. 2016, pp. 1281-1292, vol. 89, No. 6.

Liu, J. et al., "Droxinostat, a Histone Deacetylase Inhibitor, Induces Apoptosis in Hepatocellular Carcinoma Cell Lines via Activation of the Mitochondrial Pathway and Downregulation of FLIP," Translational Oncology, Feb. 2016, pp. 70-78, vol. 9, No. 1, Elsevier Inc. on behalf of Neoplasia Press, Inc.

Loo, D. et al., "Measurement of Cell Death," Methods Cell Biol., 1998, pp. 251-264, vol. 57, Chapter 14, Academic Press.

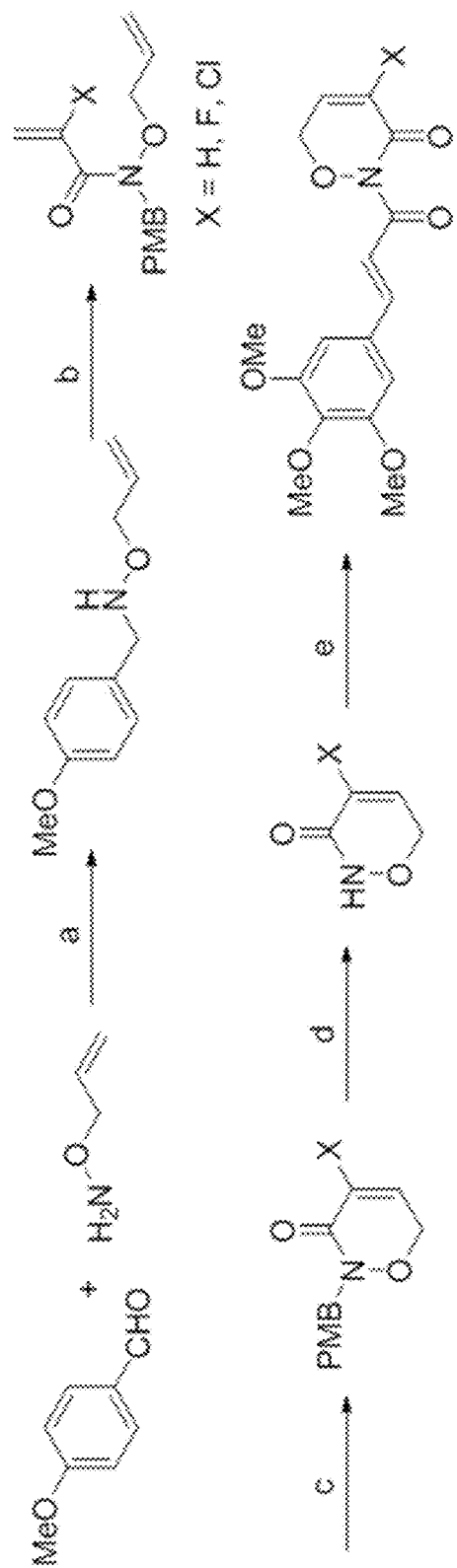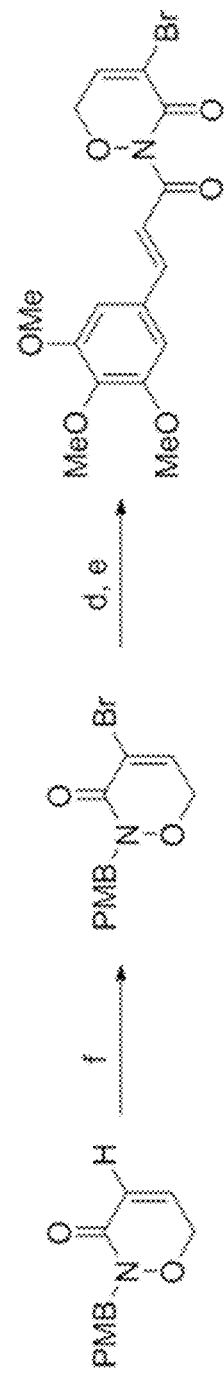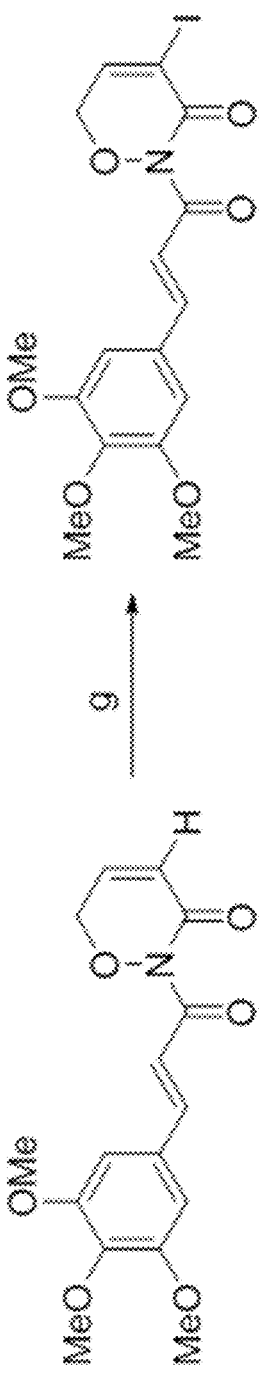
FIG. 3A
FIG. 3B
FIG. 3C

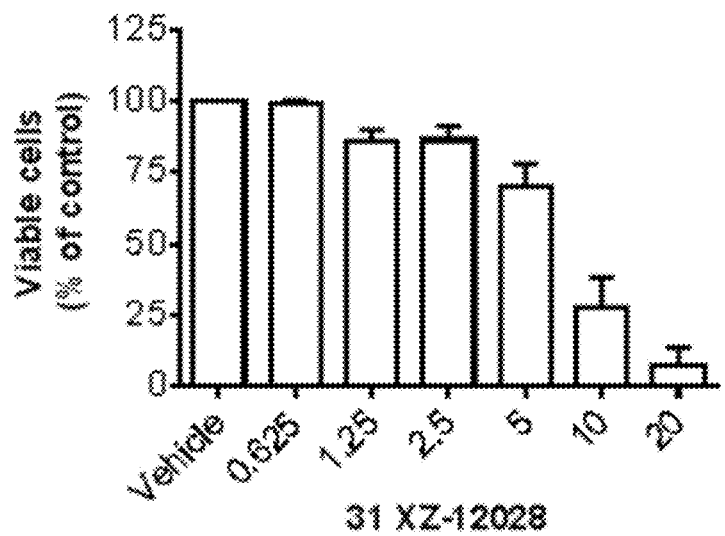
FIG. 4A
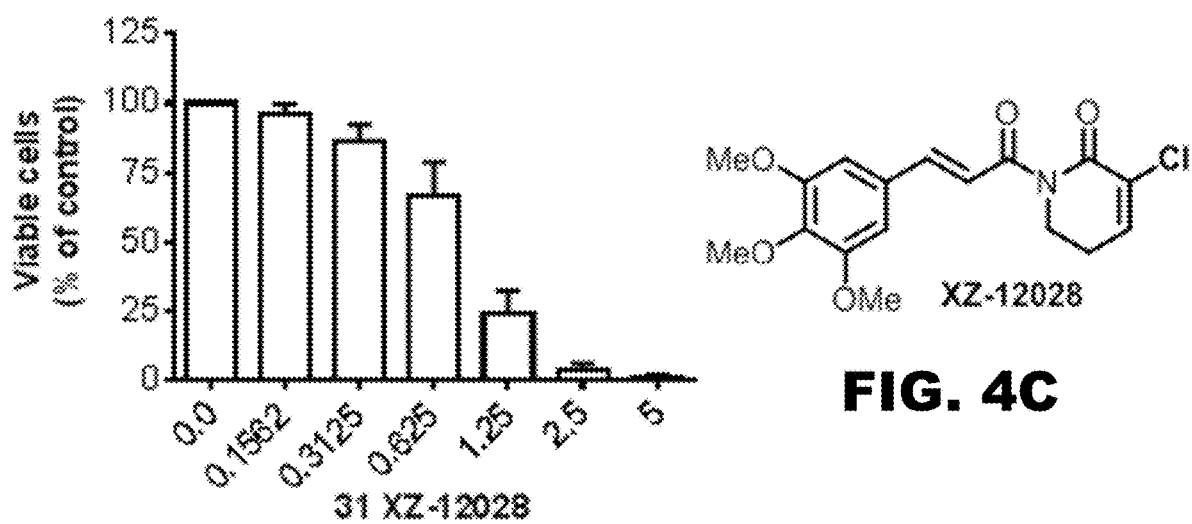
FIG. 4B
FIG. 4C

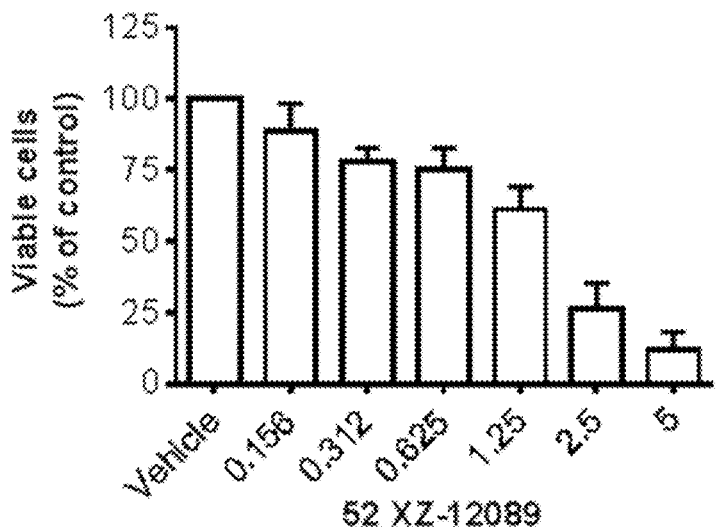
FIG. 5A
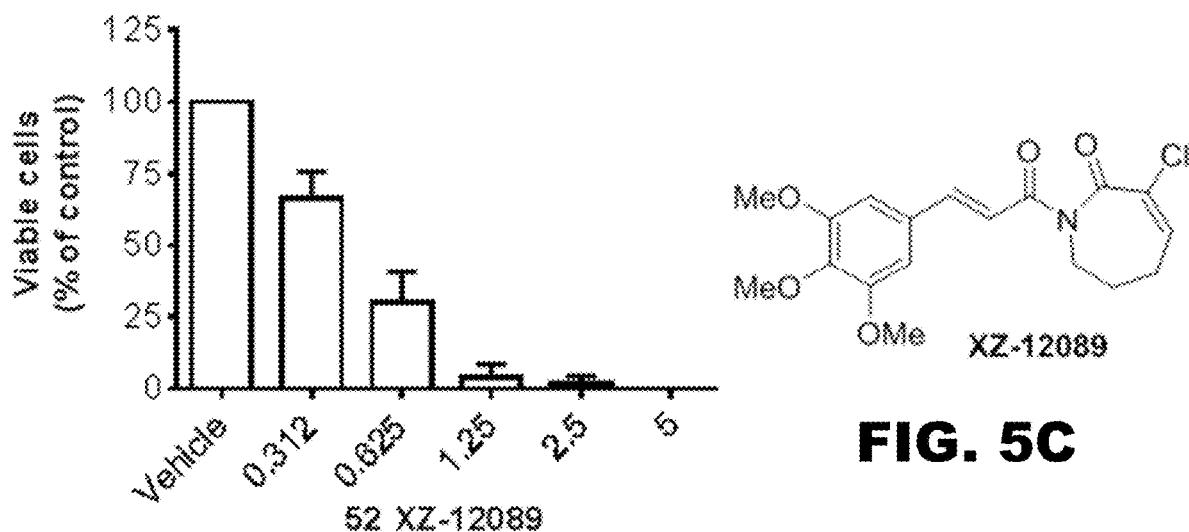
FIG. 5B
FIG. 5C

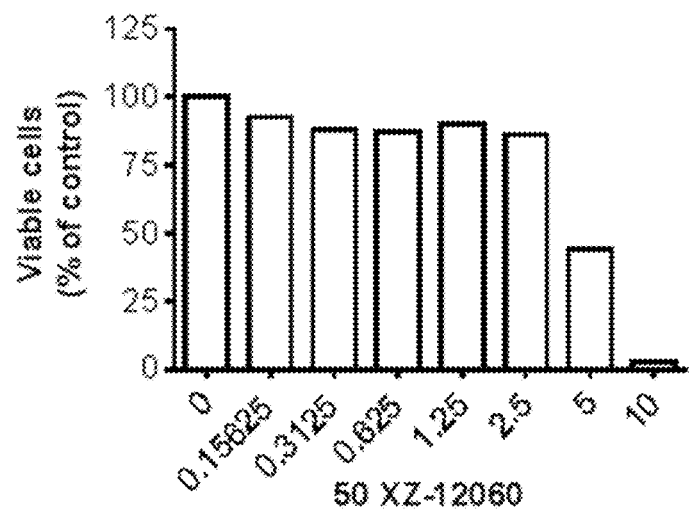
FIG. 5D
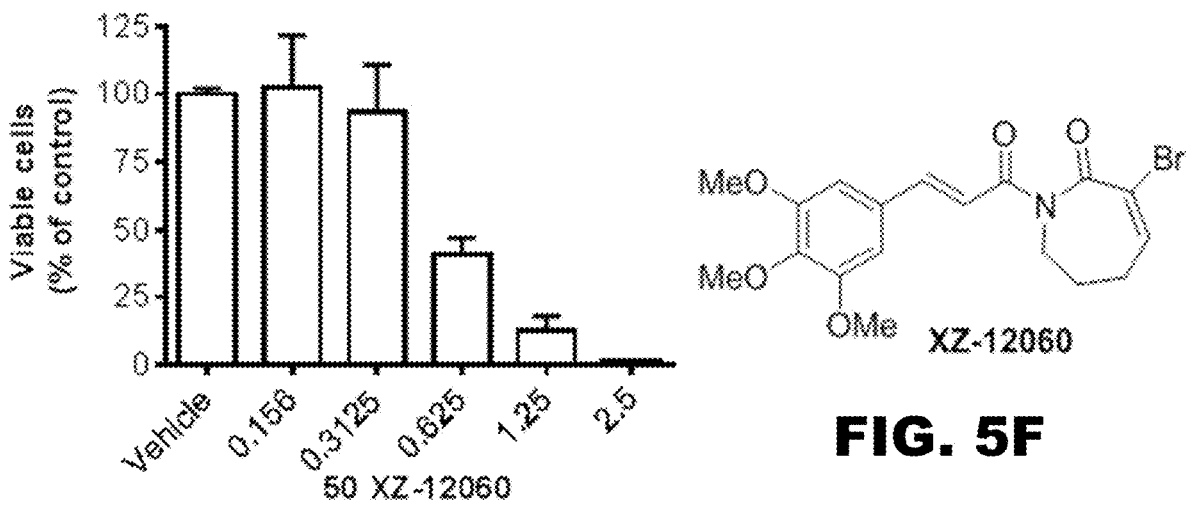
FIG. 5E
FIG. 5F

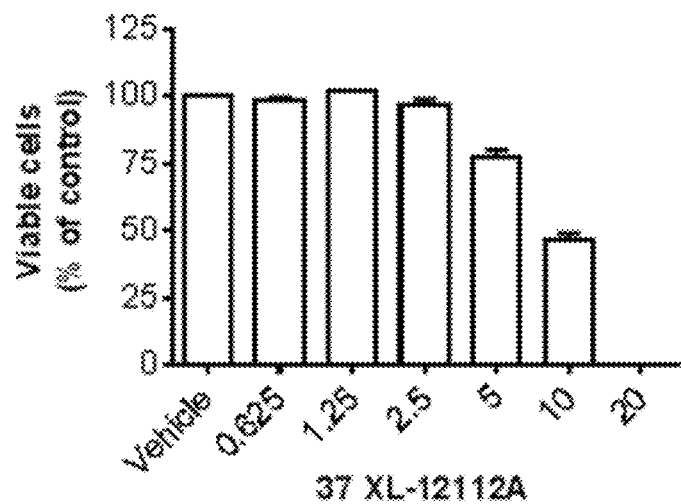
FIG. 6D
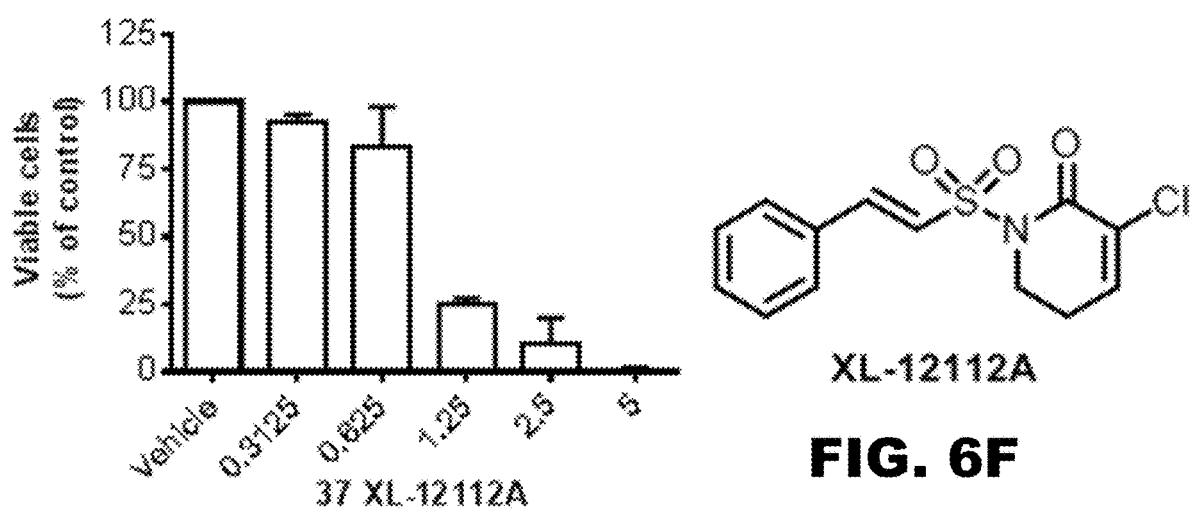
FIG. 6E
FIG. 6F

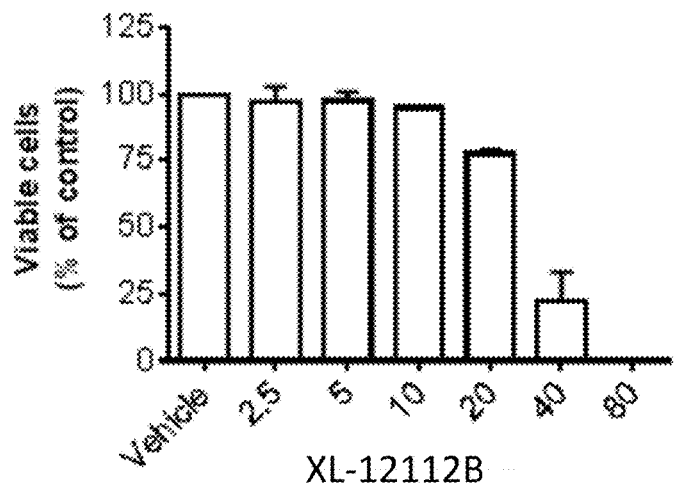
FIG. 6G
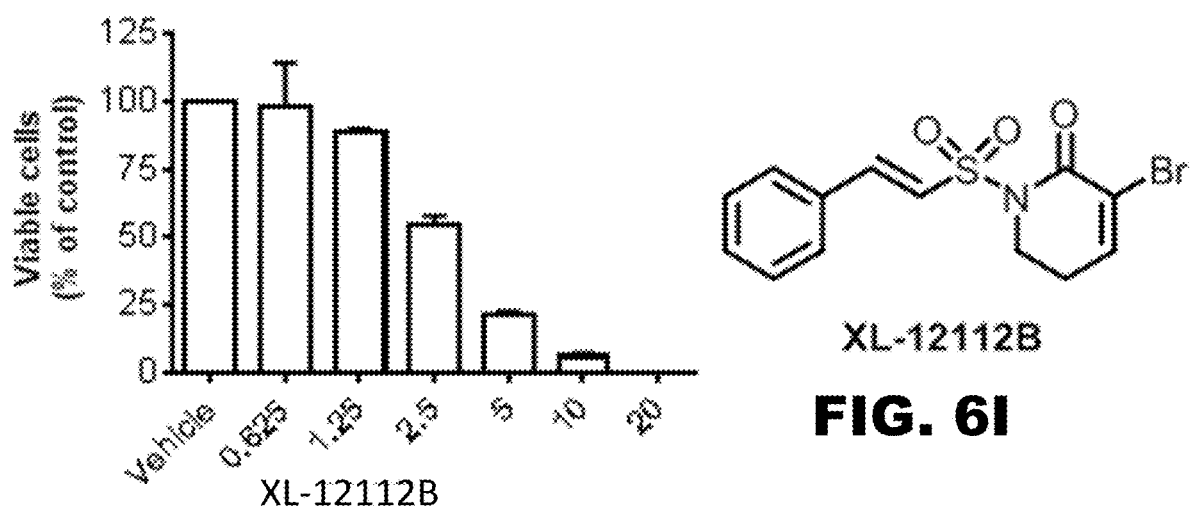
FIG. 6H
FIG. 6I

PIPERLONGUMINE ANALOGUES AND USES THEREOF

GOVERNMENTAL RIGHTS

This invention was made with government support under R56 AG056372-01 awarded by the National Institutes of Health. The government has certain rights in the invention.

CROSS REFERENCE TO RELATED APPLICATIONS

This application claims the benefit of International Patent Application number PCT/US2018/33479, filed May 18, 2019, which is incorporated herein by reference in its entirety.

FIELD OF THE INVENTION

The present invention relates to piperlongumine and piperlongumine derivatives and their method of use in the treatment of cancer. The present invention also relates to pharmaceutical compositions containing these compounds as well as various uses thereof.

BACKGROUND OF THE INVENTION

Age is a leading risk factor for many human diseases, including most cancers, atherosclerosis, neurodegenerative diseases, diabetes, and many others. An increasing body of evidence demonstrates that aging is associated with an accumulation of senescent cells. When a cell becomes senescent, it loses its reproductive function, which may cause tissue degeneration. In addition, senescent cells produce increased levels of free radical and various inflammatory mediators that can induce tissue damage and cell transformation. Therefore, selective depletion of senescent cells may be a novel anti-aging strategy that may prevent various human diseases associated with aging and rejuvenate the body to live a healthier lifespan. This assumption is supported by a recent study showing that selective depletion of senescent cells in the BubR1 progeroid mouse model by a genetic approach resulted in the delay of various age-related pathologies and disorders. However, there is no drug that can selectively deplete senescent cells. Therefore, a method to selectively deplete senescent cells is needed.

SUMMARY OF THE INVENTION

One aspect of the present disclosure is directed to compounds of Formula (I):

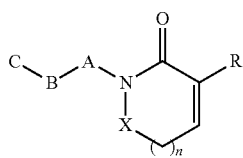

(I)

wherein R is selected from the group consisting of hydrogen, deuterium, halogen, $CF_3$, $NO_2$, and CN; X is selected from the group consisting of $CH_2$, O, NH, S, C(O), and $S(O)_2$; n is an integer from 0-2; A is C(O) or $S(O)_2$; B is selected from the group consisting of

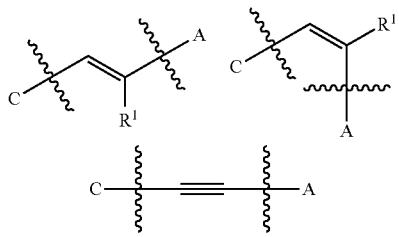

wherein R is selected from the group consisting of hydrogen, deuterium halogen, $CF_3$, CN, OH, $OCH_3$, OR', SR', NR'R', NR'COR', NR'CONR'R', NR'$CO_2$R', COR', $CO_2$R', NOR', $NO_2$, CONR'R', OC(O)NR'R', $SO_2$R', $SO_2$NR'R', NR'$SO_2$R', NR'$SO_2$NR'R', C(O)C(O)R', C(O)$CH_2$C(O)R', a substituted or unsubstituted $C_1$-$C_6$ alkyl, a substituted or unsubstituted $C_1$-$C_6$ alkenyl, a substituted or unsubstituted $C_1$-$C_6$ alkynyl, a substituted or unsubstituted aryl, and a substituted or unsubstituted heteroaryl; R' is independently selected from the group consisting of hydrogen, substituted $C_1$-$C_4$ aliphatic moiety, aliphatic moiety containing nitrogen, oxygen, or sulfur, or alternately, two R' moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur; C is hydrogen or

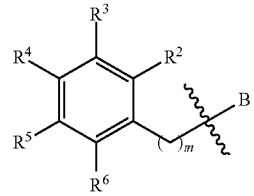

wherein $R^2$, $R^3$, $R^4$, $R^5$, and $R^6$ are each independently selected from the group consisting of hydrogen, deuterium, halogen, $CF_3$, CN, OH, $OCH_3$, OR", SR", NR"R", NR"COR", NR"CONR"R", NR"$COO_2$R", COR", $CO_2$R", NOR", $NO_2$, CONR"R", OC(O)NR"R", $SO_2$R", $SO_2$NR"R", NR"$SO_2$R", NR"$SO_2$NR"R", C(O)C(O)R", and C(O)$CH_2$C(O)R", a substituted or unsubstituted $C_1$ to $C_6$ alkyl, a substituted or unsubstituted $C_1$ to $C_6$ alkenyl, a substituted or unsubstituted $C_1$ to $C_6$ alkynyl, a substituted or unsubstituted aryl, and a substituted or unsubstituted heteroaryl; R" is independently selected from the group consisting of hydrogen, substituted $C_1$-$C_4$ aliphatic moiety, aliphatic moiety containing nitrogen, oxygen, or sulfur, or alternately, two R" moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur; optionally, $R^2$ and $R^3$, $R^3$ and $R^4$, $R^4$ and $R^5$, and $R^5$ and $R^6$ are taken together to form a 4-8 membered saturated or unsaturated ring having 0-3 heteroatoms independently selected from the group consisting of nitrogen, oxygen, or sulfur; m is an integer from 0-6; and optionally, the phenyl ring in C or R' and C taken together may be replaced by the following one or more monocyclic aryl, one or more heteroaryl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from the group consisting of nitrogen, oxygen or sulfur, or an 6-10 membered bicyclic heteroaryl ring having 1-5 heteroatoms independently selected from the group consisting of nitrogen, oxygen, or sulfur.

Another aspect of the present disclosure is directed to a method of selectively killing one or more senescent cells in a subject in need thereof. The method comprises administering to the subject a composition comprising a therapeutically effective amount of a compound of Formula (I) as described herein.

An additional aspect of the present disclosure is directed to a method for delaying at least one feature of aging in a subject, the method comprising administering a composition comprising a therapeutically effective amount of a compound of Formula (I) as described herein.

A further aspect of the present disclosure is directed to a method of treating an age-related disease or condition, the method comprising administering a composition comprising a therapeutically effective amount of a compound of Formula (I) as described herein.

BRIEF DESCRIPTION OF THE FIGURES

FIG. 3A, FIG. 3B, and FIG. 3C depicts schemes for the synthesis of 1,2-oxazin-3(6H)-one containing piperlongumine analogues. Reagents and conditions: a) i. $MgSO_4$, TEA, DCM; ii. borane pyridine complex; b) acyl chloride, TEA, DCM, 0° C.; c) Grubbs catalyst $2^{nd}$ generation, toluene, 85° C.; d) TFA, anisole, 85° C.; e) i. n-BuLi, THF; ii. (E)-3-(3,4,5-trimethoxyphenyl)acrylic pivalic anhydride; f) $Br_2$, pyridine, $CCl_4$; g) $I_2$, pyridine, $CCl_4$.

FIG. 4A, FIG. 4B, FIG. 4C, FIG. 4D, FIG. 4E, FIG. 4F, FIG. 4G, FIG. 4H, and FIG. 4I depict graphs showing piperlongumine analogues selectively kills senescent WI38 cells over normal WI38 cells. Normal WI38 cells (FIG. 4A, FIG. 4D, and FIG. 4G), ionizing radiation (IR, 10 Gy) induced senescent WI38 cells (FIG. 4B, FIG. 4E, and FIG. 4H). Cell viability was measured at 72 hours after piperlongumine treatment and expressed as percent of control. (FIG. 4C) Structure of XZ-12028. (FIG. 4F) Structure of XZ-12029. (FIG. 4I) Structure GZ-11727.

FIG. 5A, FIG. 5B, FIG. 5C, FIG. 5D, FIG. 5E, and FIG. 5F depict graphs showing piperlongumine analogues selectively kills senescent WI38 cells over normal WI38 cells. Normal WI38 cells (FIG. 5A and FIG. 5D), ionizing radiation (IR, 10 Gy) induced senescent WI38 cells (FIG. 5B and FIG. 5E). Cell viability was measured at 72 hours after piperlongumine treatment and expressed as percent of control. (FIG. 5C) Structure of XZ-12089. (FIG. 5F) Structure of XZ-12060.

(FIG. 6C) Structure of XZ-12037. (FIG. 6F) Structure of XL-12112A. (FIG. 6I) Structure XL-12112B.

DETAILED DESCRIPTION OF THE INVENTION

Figure 1A:
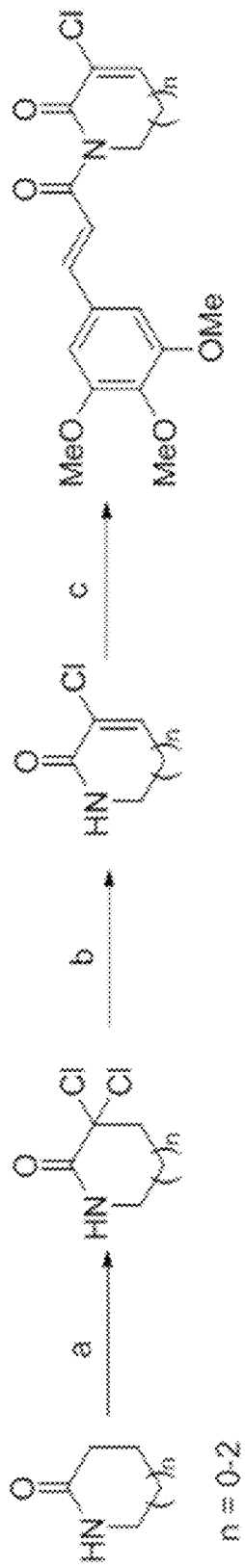
FIG. 1A, FIG. 1B, and FIG. 1C depicts schemes for the synthesis of $C_2$-chloro-substituted piperlongumine analogues (FIG. 1A), synthesis of $C_2$-bromo-substituted piperlongumine analogues (FIG. 1B), and synthesis of $C_2$-iodo-substituted piperlongumine analogues (FIG. 1C). Reagents and conditions: a) $PCl_5$, $CHCl_3$; b) $Li_2CO_3$, DMF; c) i. n-BuLi, THF; ii. (E)-3-(3,4,5-trimethoxyphenyl)acrylic pivalic anhydride; d) $PCl_5$, $ZnI_2$, $Br_2$, $CHCl_3$; e) $I_2$, Pyridine.
Figure 1B:
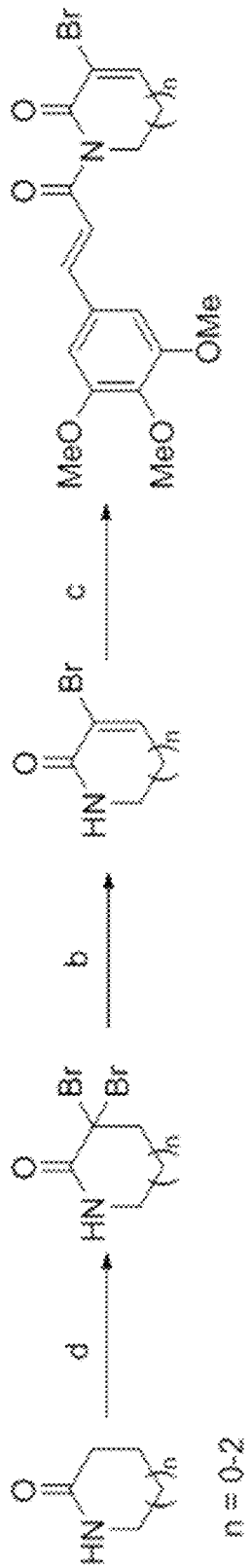
Figure 1C:
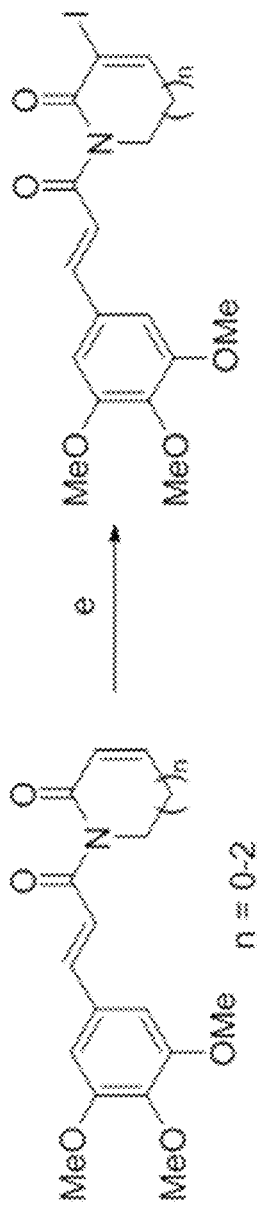
Figure 2A:
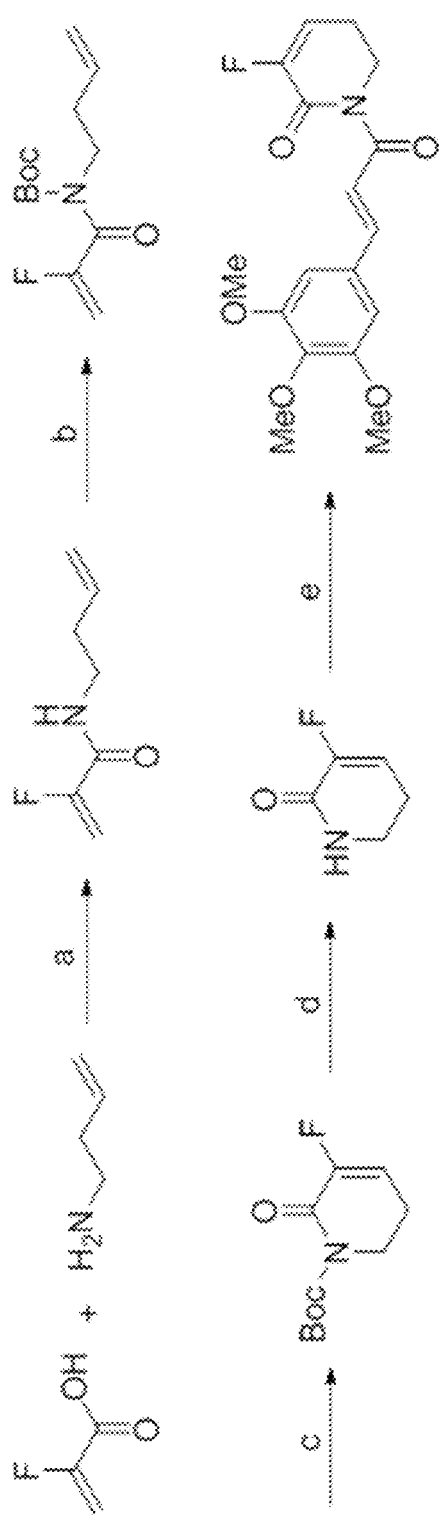
FIG. 2A and FIG. 2B depicts schemes for the synthesis of $C_2$-fluoro-substituted piperlongumine analogues (FIG. 2A) and synthesis of $C_2$-trifluoromethyl-substituted piperlongumine analogues (FIG. 2B). Reagents and conditions: a) HATU, DIPEA, DCM; b) $Boc_2O$, DMAP, DCM; c) Grubbs catalyst $2^{nd}$ generation, DCM, reflux; d) $Cu(OTf)_2$, DCM; e) i. n-BuLi, THF; ii. (E)-3-(3,4,5-trimethoxyphenyl)acrylic pivalic anhydride; f) i. $MgSO_4$, TEA, DCM; ii. $NaBH_4$; g) 2-(trifluoromethyl)acrylic acid, HATU, DIPEA, −78° C. then rt; h) Grubbs catalyst $2^{nd}$ generation, DCM, mw 60° C.; i) CAN, MeCN, water.
Figure 2B:
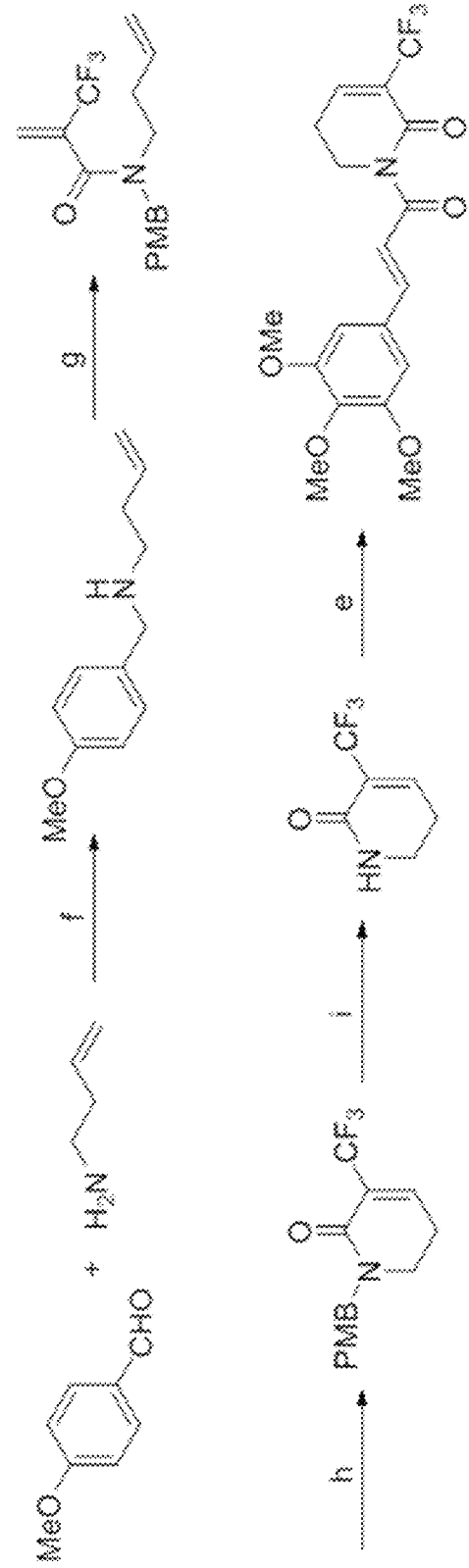
Figure 4D:
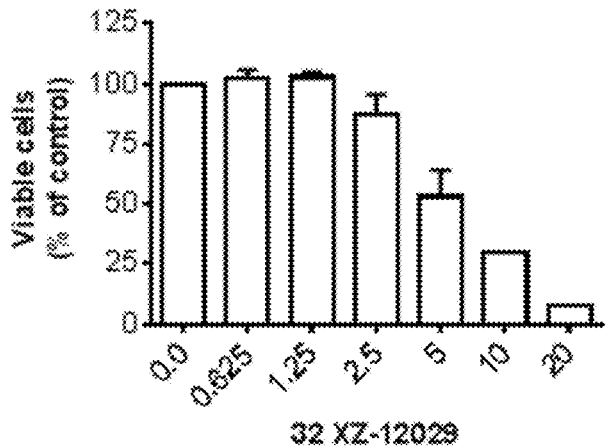
Figure 4E:
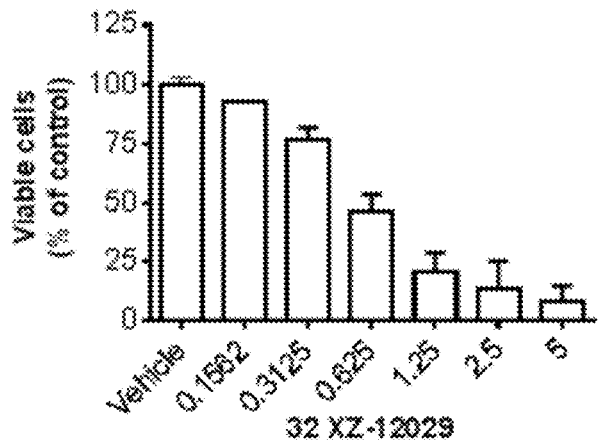
Figure 4F:
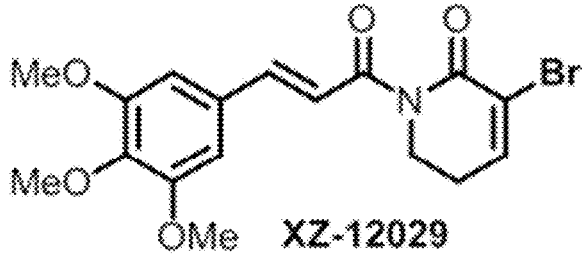
Figure 4G:
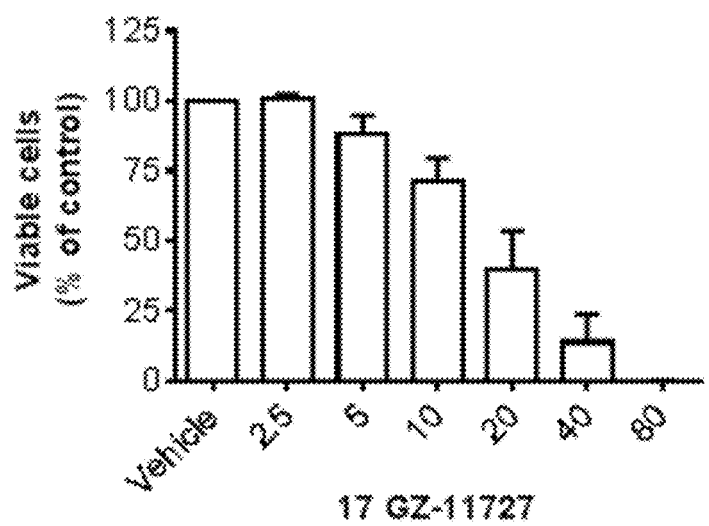
Figure 4H:
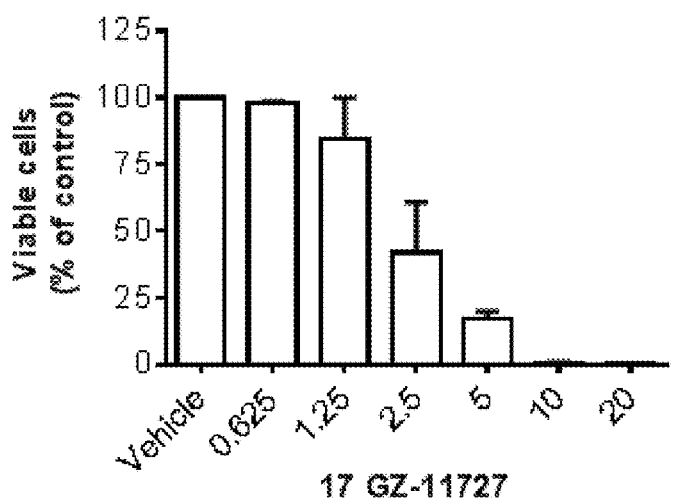
Figure 4I:
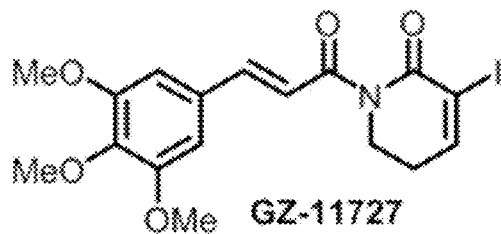
Figure 6A:
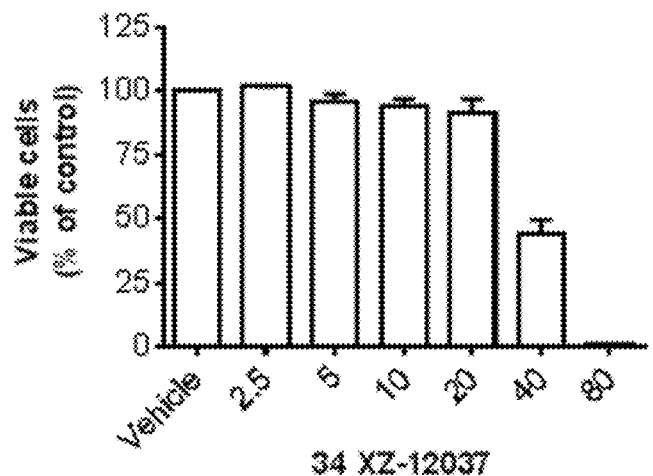
FIG. 6, FIG. 6B, FIG. 6C, FIG. 6D, FIG. 6E, FIG. 6F, FIG. 6G, FIG. 6H, and FIG. 6I depicts graphs showing piperlongumine analogues selectively kills senescent WI38 cells over normal WI38 cells. Normal WI38 cells (FIG. 6A, FIG. 6D, and FIG. 6G), ionizing radiation (IR, 10 Gy) induced senescent WI38 cells (FIG. 6B, FIG. 6E, and FIG. 6H). Cell viability was measured at 72 hours after piperlongumine treatment and expressed as percent of control.
Figure 6B:
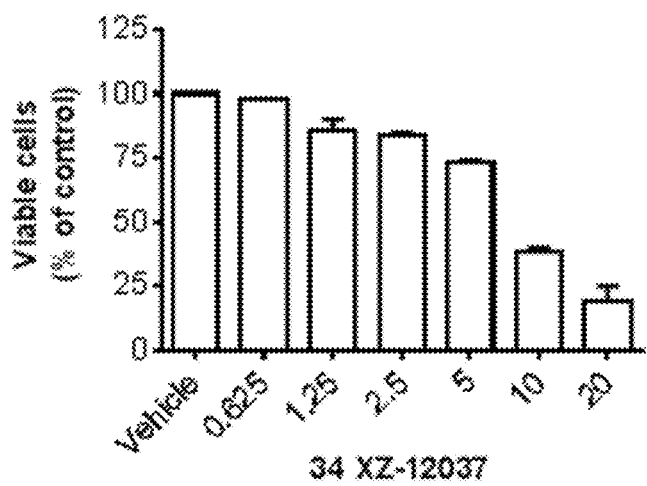
Figure 6C:
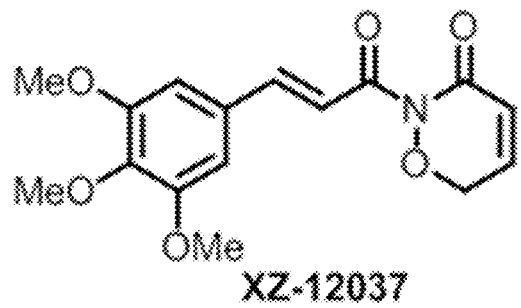

Provided herein are compositions comprising a piperlongumine (PL) derivative and methods of use. Applicants have discovered that PL derivatives selectively kill senescent cells.

Additional aspects of the disclosure are described below.

(I) Compositions

One aspect of the present disclosure encompasses PL or a PL derivative. PL or PL derivatives may be modified to improve potency, bioavailability, solubility, stability, handling properties, or a combination thereof, as compared to an unmodified version. Thus, in another aspect, a composition of the invention comprises modified PL or PL derivative. In still another aspect, a composition of the invention comprises a prodrug of a PL or PL derivative.

A composition of the invention may optionally comprise one or more additional drug or therapeutically active agent in addition to the PL or PL derivative. A composition of the invention may further comprise a pharmaceutically acceptable excipient, carrier, or diluent. Further, a composition of the invention may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents, or antioxidants.

Other aspects of the invention are described in further detail below.

(a) Piperlongumine (PL) and PL Derivatives

In general, the compounds detailed herein include compounds comprising a PL, or 5,6-dihydro-1-[(2E)-1-oxo-3-(3,4,5-trimethoxyphenyl)-2-propenyl]-2(1H)-pyridinone), structure as diagrammed below. PL may be isolated from a variety of *Piper* species (Piperaceae), including *Piper aborescens, Piper tuberculatum* and the roots of *Piper longum* L. In addition to extraction of PL from the roots of the *Piper* plant, PL can also be produced by organic synthesis (Chatterjee et al., 1967 *Tetrahedron* 23: 1769-1781). The crystal structure of PL and the adopted conformation of the molecule are described by Banerjee et al. (*Can J. Chem* 1986, 64: 867-879).

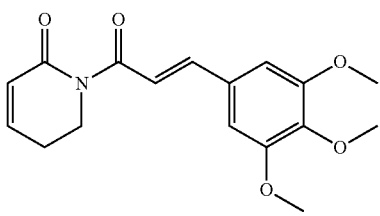 [SMILES: COc1cc(/C=C/C(=O)N2CCC=CC2=O)cc(OC)c1OC]

Provided herein are derivatives of PL. PL derivatives are modified versions of PL that are able to selectively deplete senescent cells. As used herein a "PL derivative" may be a PL derivative known in the art, a PL derivative of Formula (I). PL derivatives are known in the art. See for example, US 20090312373, WO 2009114126, CN 102125552, CN 102146054, CN 101774875, US 20110053938, WO 2012030408, US 20120059004, US 20120157455, US 20130237539, US 20140024639, CN 103601670, *Nature* 475 (2011):231-234, *Eur J Med Chem* 57 (2012):344-361, *Tetrahedron* 69 (2013):7759-7767, *PNAS* 109 (2012): 15115-15120, *Eur J Med Chem* 82 (2014):545-551, *Bioorg Med Chem Lett* 24 (2014):5727-5730, and Journal of Asian Natural Products Research 15 (2013):658-669, each of which are incorporated herein in its entirety by reference. PL derivatives with the ability to elevate ROS in senescent cell are potentially used as senolytic drugs.

Provided herein are compounds comprising Formula (I):

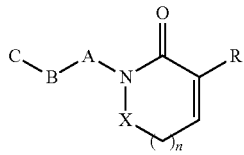

(I)

wherein:
R may be selected from the group consisting of hydrogen, deuterium, halogen, $CF_3$, $NO_2$, and CN;
X may be selected from the group consisting of $CH_2$, O, NH, S, C(O), and $S(O)_2$;
n may be an integer from 0-2;
A may be C(O) or $S(O)_2$;
B may be selected from the group consisting of:

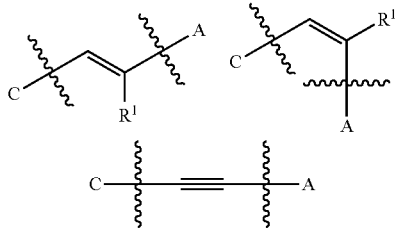

wherein:
R' may be selected from the group consisting of hydrogen, deuterium, halogen, $CF_3$, CN, OH, $OCH_3$, OR', SR', NR'R', NR'COR', NR'CONR'R', NR'$CO_2$R', COR', $CO_2$R', NOR', $NO_2$, CONR'R', OC(O)NR'R', $SO_2$NR'R', NR'$SO_2$R', NR'$SO_2$NR'R', C(O)C(O)R', C(O)$CH_2$C(O)R', a substituted or unsubstituted $C_1$-$C_6$ alkyl, a substituted or unsubstituted $C_1$-$C_6$ alkenyl, a substituted or unsubstituted $C_1$-$C_6$ alkynyl, a substituted or unsubstituted aryl, and a substituted or unsubstituted heteroaryl;
R' may be independently selected from the group consisting of hydrogen, substituted $C_1$-$C_4$ aliphatic moiety, aliphatic moiety containing nitrogen, oxygen, or sulfur, or alternately, two R' moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur;
C may be hydrogen or

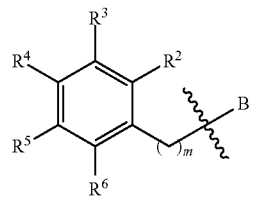

wherein:
$R^2$, $R^3$, $R^4$, $R^5$, and $R^6$ are each independently selected from the group consisting of hydrogen, deuterium, halogen, $CF_3$, CN, OH, $OCH_3$, OR", SR", NR"R", NR"COR", NR"CONR"R", NR"$CO_2$R", COR", $CO_2$R", NOR", $NO_2$, CONR"R", OC(O)NR"R", $SO_2$R", $SO_2$NR"R", NR"$SO_2$R", NR"$SO_2$NR"R", C(O)C(O)R", and C(O)$CH_2$C(O)R", a substituted or unsubstituted $C_1$ to $C_6$ alkyl, a substituted or unsubstituted $C_1$ to $C_6$ alkenyl, a substituted or unsubstituted $C_1$ to $C_6$ alkynyl, a substituted or unsubstituted aryl, and a substituted or unsubstituted heteroaryl;
R" may be independently selected from the group consisting of hydrogen, substituted $C_1$-$C_4$ aliphatic moiety, aliphatic moiety containing nitrogen, oxygen, or sulfur, or alternately, two R" moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur;
Optionally, $R^2$ and $R^3$, $R^3$ and $R^4$, $R^4$ and $R^5$, and $R^5$ and $R^6$ are taken together to form a 4-8 membered saturated or unsaturated ring having 0-3 heteroatoms independently selected from the group consisting of nitrogen, oxygen, or sulfur;
m may be an integer from 0-6; and
Optionally, the phenyl ring in C or R' and C taken together may be replaced by the following one or more monocyclic aryl, one or more heteroaryl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from the group consisting of nitrogen, oxygen or sulfur, or an 6-10 membered bicyclic heteroaryl ring having 1-5 heteroatoms independently selected from the group consisting of nitrogen, oxygen, or sulfur.

In an embodiment, a compound of Formula (I) comprises any of the preceding compounds of Formula (I), wherein R may be selected from the group hydrogen, halogen, and $CF_3$. In a preferred embodiment, a compound of Formula (I) comprises any of the preceding compounds of Formula (I), wherein R may be selected from the group consisting of H, F, Cl, Br, I, and $CF_3$.

In another embodiment, a compound of Formula (I) comprises any of the preceding compounds of Formula (I), wherein X may be selected from the group consisting of $CH_2$, NH, S, and O. In a preferred embodiment, a compound of Formula (I) comprises any of the preceding compounds of Formula (I), wherein X may be selected from the group consisting of $CH_2$ and O.

In still another embodiment, a compound of Formula (I) comprises any of the preceding compounds of Formula (I), wherein n may be an integer from 1-2. In other embodiments, a compound of Formula (I) comprises any of the preceding compounds of Formula (I), wherein n may be 1 or 2. In a preferred embodiment, a compound of Formula (I) comprises any of the preceding compounds of Formula (I), wherein n may be 1. In another preferred embodiment, a compound of Formula (I) comprises any of the preceding compounds of Formula (I), wherein n may be 2.

In yet still another embodiment, a compound of Formula (I) comprises any of the preceding compounds of Formula (I), wherein A may be C(O).

In a different embodiment, a compound of Formula (I) comprises any of the preceding compounds of Formula (I), wherein A may be $SO_2$.

In an embodiment, a compound of Formula (I) comprises any of the preceding compounds of Formula (I), wherein B may be

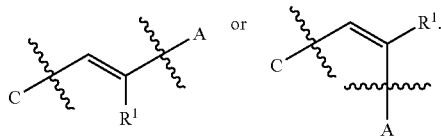

In a preferred embodiment, a compound of Formula (I) comprises any of the preceding compounds of Formula (I), wherein B may be

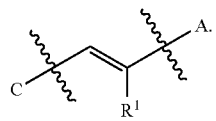

In an embodiment, a compound of Formula (I) comprises any of the preceding compounds of Formula (I), wherein $R^1$ may be selected from the group consisting of H, substituted $C_1$-$C_4$ aliphatic moiety and aliphatic moiety containing nitrogen. In a preferred embodiment, a compound of Formula (I) comprises any of the preceding compounds of Formula (I), wherein $R^1$ may be H.

In yet another embodiment, a compound of Formula (I) comprises any of the preceding compounds of Formula (I), wherein C may be

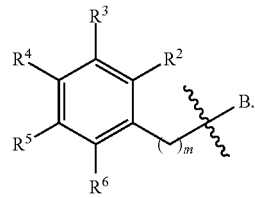

In a different embodiment, a compound of Formula (I) comprises any of the preceding compounds of Formula (I), wherein C may be H. In still a different embodiment, a compound of Formula (I) comprises any of the preceding compounds of Formula (I), wherein R' and C may be taken together and replaced by a 6-10 membered bicyclic heteroaryl ring having 1-5 heteroatoms independently selected from the group consisting of nitrogen, oxygen, or sulfur.

In an embodiment, a compound of Formula (I) comprises any of the preceding compounds of Formula (I), wherein $R^2$, $R^3$, $R^4$, $R^5$, and $R^6$ may each independently be selected from the group consisting of H, halogen, $OCH_3$, OR', a substituted or unsubstituted $C_1$ to $C_6$ alkyl, a substituted or unsubstituted $C_1$ to $C_6$ alkenyl, and a substituted or unsubstituted $C_1$ to $C_6$ alkynyl. In a preferred embodiment, a compound of Formula (I) comprises any of the preceding compounds of Formula (I), wherein $R^2$, $R^3$, $R^4$, $R^5$, and $R^6$ may each independently be selected from the group consisting of H, $OCH_3$, and $O(CH_2)N(CH_3)_2$.

In an embodiment, a compound of Formula (I) comprises any of the preceding compounds of Formula (I), wherein R' may be independently selected from the group consisting of hydrogen, substituted $C_1$-$C_4$ aliphatic moiety.

In an embodiment, a compound of Formula (I) comprises Formula (I), wherein R may be selected from the group consisting of H, F, Cl, Br, I, and $CF_3$; X may be selected from the group consisting of $CH_2$, NH, S, and O; n may be an integer from 1-2; A may be C(O) or $SO_2$; B may be

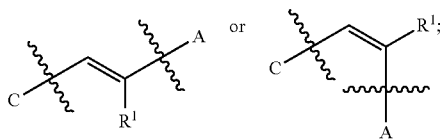

$R^1$ may be selected from the group consisting of H, substituted $C_1$-$C_4$ aliphatic moiety and aliphatic moiety containing nitrogen; C may be

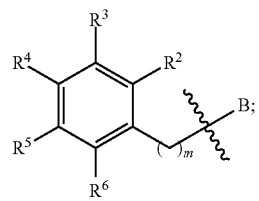

$R^2$, $R^3$, $R^4$, $R^5$, and $R^6$ may each independently be selected from the group consisting of H, halogen, $OCH_3$, OR', a substituted or unsubstituted $C_1$ to $C_6$ alkyl, a substituted or unsubstituted $C_1$ to $C_6$ alkenyl, and a substituted or unsubstituted $C_1$ to $C_6$ alkynyl; and R' may be independently selected from the group consisting of hydrogen, substituted $C_1$-$C_4$ aliphatic moiety.

In an embodiment, a compound of Formula (I) comprises Formula (I), wherein R may be selected from the group hydrogen, halogen, and $CF_3$; X may be selected from the group consisting of $CH_2$ and O; n may be an integer from 1-2; A may be C(O) or $SO_2$; B may be

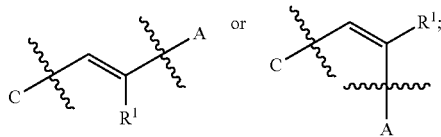

$R^1$ may be selected from the group consisting of H, substituted $C_1$-$C_4$ aliphatic moiety and aliphatic moiety containing nitrogen; C may be

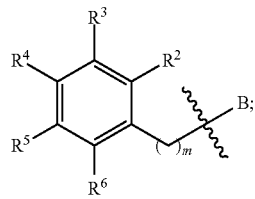

$R^2$, $R^3$, $R^4$, $R^5$, and $R^6$ may each independently be selected from the group consisting of H, halogen, $OCH_3$, OR', a substituted or unsubstituted $C_1$ to $C_6$ alkyl, a substituted or unsubstituted $C_1$ to $C_6$ alkenyl, and a substituted or unsubstituted $C_1$ to $C_6$ alkynyl; and R' may be independently selected from the group consisting of hydrogen, substituted $C_1$-$C_4$ aliphatic moiety.

In an embodiment, a compound of Formula (I) comprises Formula (I), wherein R may be selected from the group hydrogen, halogen, and $CF_3$; X may be selected from the group consisting of $CH_2$, NH, S, and O. n may be 1 or 2; A may be C(O) or $SO_2$; B may be

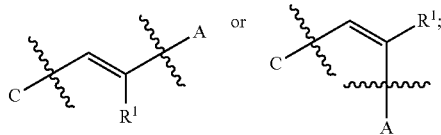

$R^1$ may be selected from the group consisting of H, substituted $C_1$-$C_4$ aliphatic moiety and aliphatic moiety containing nitrogen; C may be

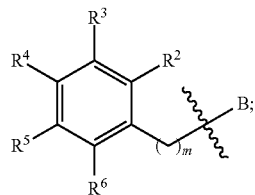

$R^2$, $R^3$, $R^4$, $R^5$, and $R^6$ may each independently be selected from the group consisting of H, halogen, $OCH_3$, OR', a substituted or unsubstituted $C_1$ to $C_6$ alkyl, a substituted or unsubstituted $C_1$ to $C_6$ alkenyl, and a substituted or unsubstituted $C_1$ to $C_6$ alkynyl; and R' may be independently selected from the group consisting of hydrogen, substituted $C_1$-$C_4$ aliphatic moiety.

In an embodiment, a compound of Formula (I) comprises Formula (I), wherein R may be selected from the group hydrogen, halogen, and $CF_3$; X may be selected from the group consisting of $CH_2$, NH S, and O; n may be 1; A may be C(O) or $SO_2$; B may be

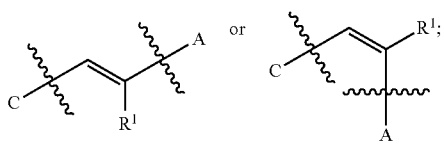

$R^1$ may be selected from the group consisting of H, substituted $C_1$-$C_4$ aliphatic moiety and aliphatic moiety containing nitrogen; C may be

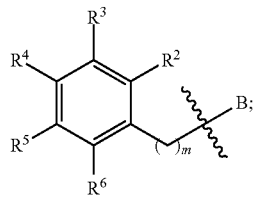

$R^2$, $R^3$, $R^4$, $R^5$, and $R^6$ may each independently be selected from the group consisting of H, halogen, $OCH_3$, OR', a substituted or unsubstituted $C_1$ to $C_6$ alkyl, a substituted or unsubstituted $C_1$ to $C_6$ alkenyl, and a substituted or unsubstituted $C_1$ to $C_6$ alkynyl; and R' may be independently selected from the group consisting of hydrogen, substituted $C_1$-$C_4$ aliphatic moiety.

In an embodiment, a compound of Formula (I) comprises Formula (I), wherein R may be selected from the group hydrogen, halogen, and $CF_3$; X may be selected from the group consisting of $CH_2$, NH, S, and O; n may be an integer from 1-2; A may be C(O); B may be

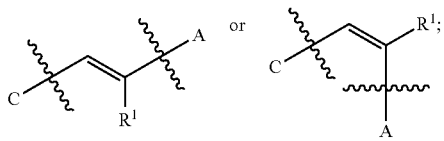

$R^1$ may be selected from the group consisting of H, substituted $C_1$-$C_4$ aliphatic moiety and aliphatic moiety containing nitrogen; C may be

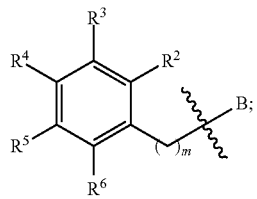

$R^2$, $R^3$, $R^4$, $R^5$, and $R^6$ may each independently be selected from the group consisting of H, halogen, $OCH_3$, OR', a substituted or unsubstituted $C_1$ to $C_6$ alkyl, a substituted or unsubstituted $C_1$ to $C_6$ alkenyl, and a substituted or unsubstituted $C_1$ to $C_6$ alkynyl; and R' may be independently selected from the group consisting of hydrogen, substituted $C_1$-$C_4$ aliphatic moiety.

In an embodiment, a compound of Formula (I) comprises Formula (I), wherein R may be selected from the group hydrogen, halogen, and $CF_3$; X may be selected from the group consisting of $CH_2$, NH, S, and O; n may be an integer from 1-2; A may be C(O) or $SO_2$; B may be

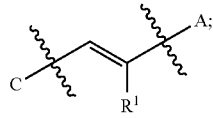

$R^1$ may be selected from the group consisting of H, substituted $C_1$-$C_4$ aliphatic moiety and aliphatic moiety containing nitrogen; C may be

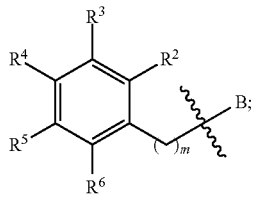

$R^2$, $R^3$, $R^4$, $R^5$, and $R^6$ may each independently be selected from the group consisting of H, halogen, $OCH_3$, OR', a substituted or unsubstituted $C_1$ to $C_6$ alkyl, a substituted or unsubstituted $C_1$ to $C_6$ alkenyl, and a substituted or unsubstituted $C_1$ to $C_6$ alkynyl; and R' may be independently selected from the group consisting of hydrogen, substituted $C_1$-$C_4$ aliphatic moiety.

In an embodiment, a compound of Formula (I) comprises Formula (I), wherein R may be selected from the group hydrogen, halogen, and $CF_3$; X may be selected from the group consisting of $CH_2$, NH, S, and O; n may be an integer from 1-2; A may be C(O) or $SO_2$; B may be

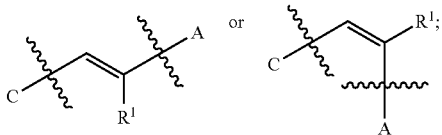

$R^1$ may be H; C may be

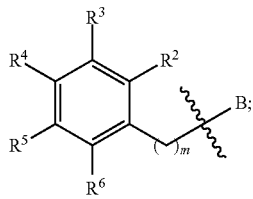

$R^2$, $R^3$, $R^4$, $R^5$, and $R^6$ may each independently be selected from the group consisting of H, halogen, $OCH_3$, OR', a substituted or unsubstituted $C_1$ to $C_6$ alkyl, a substituted or unsubstituted $C_1$ to $C_6$ alkenyl, and a substituted or unsubstituted $C_1$ to $C_6$ alkynyl; and R' may be independently selected from the group consisting of hydrogen, substituted $C_1$-$C_4$ aliphatic moiety.

In an embodiment, a compound of Formula (I) comprises Formula (I), wherein R may be selected from the group hydrogen, halogen, and $CF_3$; X may be selected from the group consisting of $CH_2$, NH, S, and O; n may be an integer from 1-2; A may be C(O) or $SO_2$; B may be

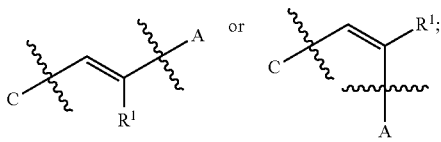

$R^1$ may be selected from the group consisting of H, substituted $C_1$-$C_4$ aliphatic moiety and aliphatic moiety containing nitrogen; C may be

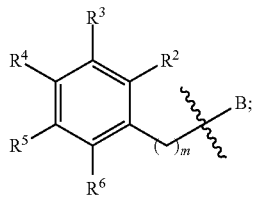

$R^2$, $R^3$, $R^4$, $R^5$, and $R^6$ may each independently be selected from the group consisting of H, $OCH_3$, and $O(CH_2)N(CH_3)_2$; and R' may be independently selected from the group consisting of hydrogen, substituted $C_1$-$C_4$ aliphatic moiety.

In an exemplary embodiment, R may be F, X may be $CH_2$, n may be 1, A may be C(O), B may be

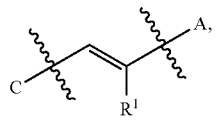

$R^1$ may be H, C may be

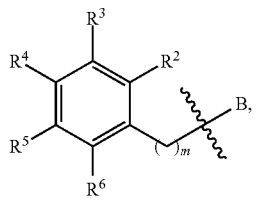

m may be 0, $R^2$ and $R^6$ may be H, and $R^3$, $R^4$, and $R^5$ may be $OCH_3$.

In an exemplary embodiment, R may be Cl, X may be CH$_2$, n may be 1, A may be C(O), B may be

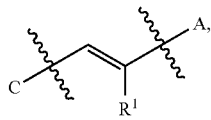

R$^1$ may be H, C may be

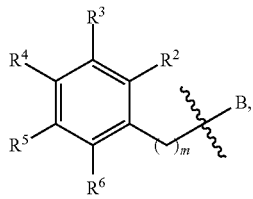

m may be 0, R$^2$ and R$^6$ may be H, and R$^3$, R$^4$, and R$^5$ may be OCH$_3$.

In an exemplary embodiment, R may be br, X may be CH$_2$, n may be 1, A may be C(O), B may be

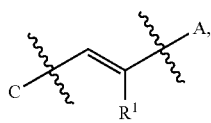

R$^1$ may be H, C may be

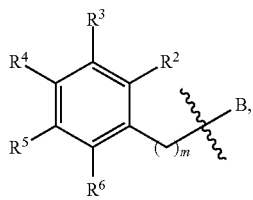

m may be 0, R$^2$ and R$^6$ may be H, and R$^3$, R$^4$, and R$^5$ may be OCH$_3$.

In an exemplary embodiment, R may be I, X may be CH$_2$, n may be 1, A may be C(O), B may be

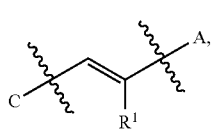

R$^1$ may be H, C may be

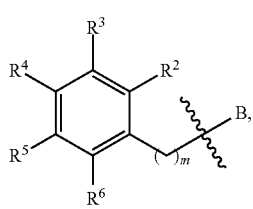

m may be 0, R$^2$ and R$^6$ may be H, and R$^3$, R$^4$, and R$^5$ may be OCH$_3$.

In an exemplary embodiment, R may be CF$_3$, X may be CH$_2$, n may be 1, A may be C(O), B may be

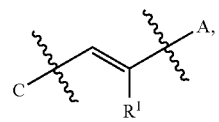

R$^1$ may be H, C may be

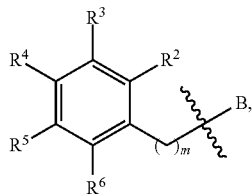

m may be 0, R$^2$ and R$^6$ may be H, and R$^3$, R$^4$, and R$^5$ may be OCH$_3$.

In an exemplary embodiment, R may be Cl, X may be CH$_2$, n may be 2, A may be C(O), B may be

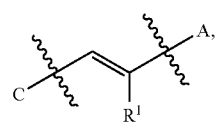

R$^1$ may be H, C may be

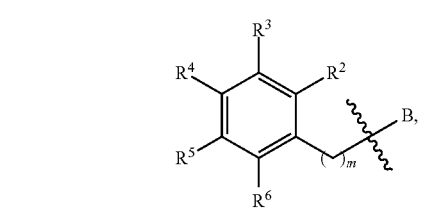

m may be 0, R$^2$ and R$^6$ may be H, and R$^3$, R$^4$, and R$^5$ may be OCH$_3$.

In an exemplary embodiment, R may be Br, X may be CH$_2$, n may be 2, A may be C(O), B may be

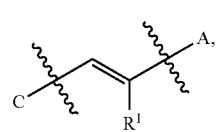

$R^1$ may be H, C may be

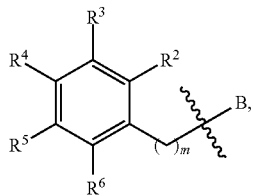

m may be 0, $R^2$ and $R^6$ may be H, and $R^3$, $R^4$, and $R^5$ may be $OCH_3$.

In an exemplary embodiment, R may be F, X may be O, n may be 1, A may be C(O), B may be

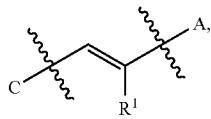

$R^1$ may be H, C may be

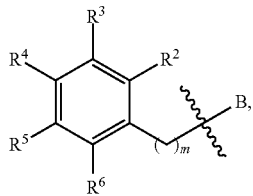

m may be 0, $R^2$ and $R^6$ may be H, and $R^3$, $R^4$, and $R^5$ may be $OCH_3$.

In an exemplary embodiment, R may be Cl, X may be O, n may be 1, A may be C(O), B may be

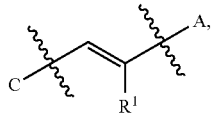

$R^1$ may be H, C may be

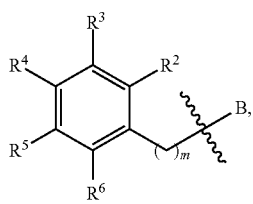

m may be 0, $R^2$ and $R^6$ may be H, and $R^3$, $R^4$, and $R^5$ may be $OCH_3$.

In an exemplary embodiment, R may be Br, X may be O, n may be 1, A may be C(O), B may be

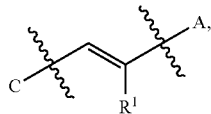

$R^1$ may be H, C may be

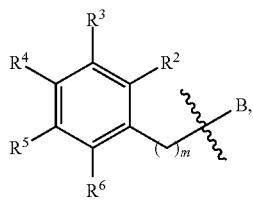

m may be 0, $R^2$ and $R^6$ may be H, and $R^3$, $R^4$, and $R^5$ may be $OCH_3$.

In an exemplary embodiment, R may be I, X may be O, n may be 1, A may be C(O), B may be

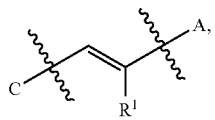

$R^1$ may be H, C may be

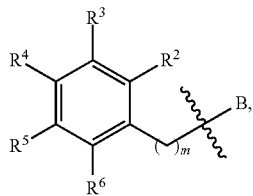

m may be 0, $R^2$ and $R^6$ may be H, and $R^3$, $R^4$, and $R^5$ may be $OCH_3$.

In an exemplary embodiment, R may be Cl, X may be $CH_2$, n may be 1, A may be C(O), B may be

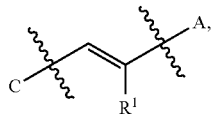

$R^1$ may be H, C may be

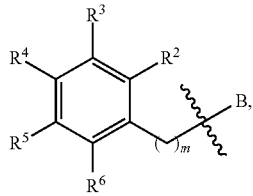

m may be 0, $R^2$, $R^3$, $R^5$, and $R^6$ may be H, and, $R^4$ may be $OCH_3$.

In an exemplary embodiment, R may be Br, X may be CH$_2$, n may be 1, A may be C(O), B may be

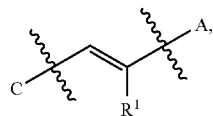

R$^1$ may be H, C may be

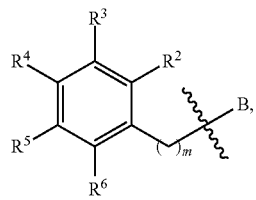

m may be 0, R$^2$, R$^3$, R$^5$, and R$^6$ may be H, and, R$^4$ may be OCH$_3$.

In an exemplary embodiment, R may be Cl, X may be CH$_2$, n may be 2, A may be C(O), B may be

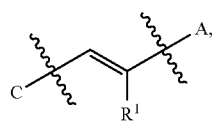

R$^1$ may be H, C may be

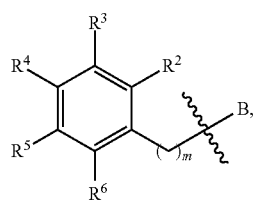

m may be 0, R$^2$, R$^3$, R$^5$, and R$^6$ may be H, and, R$^4$ may be OCH$_3$.

In an exemplary embodiment, R may be Br, X may be CH$_2$, n may be 2, A may be C(O), B may be

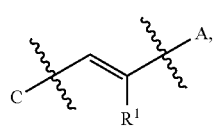

R$^1$ may be H, C may be

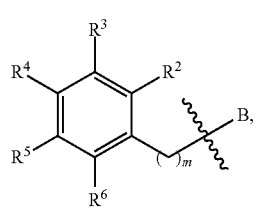

m may be 0, R$^2$, R$^3$, R$^5$, and R$^6$ may be H, and, R$^4$ may be OCH$_3$.

In an exemplary embodiment, R may be H, X may be O, n may be 1, A may be C(O), B may be

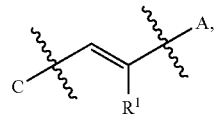

R$^1$ may be H, C may be

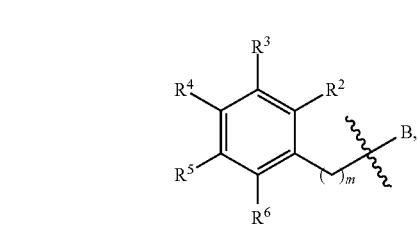

m may be 0, R$^2$, R$^3$, R$^5$, and R$^6$ may be H, and, R$^4$ may be OCH$_3$.

In an exemplary embodiment, R may be H, X may be O, n may be 1, A may be C(O), B may be

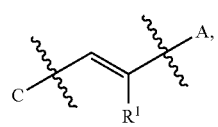

R$^1$ may be H, C may be H.

In an exemplary embodiment, R may be Br, X may be CH$_2$, n may be 1, A may be C(O), B may be

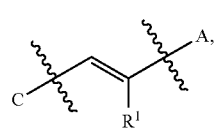

R$^1$ and C may be

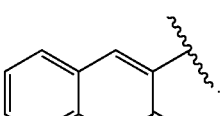

.

In an exemplary embodiment, R may be Br, X may be CH$_2$, n may be 2, A may be C(O), B may be

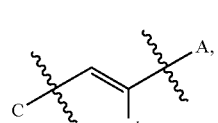

$R^1$ and C may be

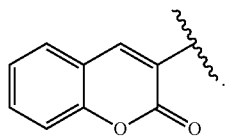 [SMILES: *c1cc2ccccc2oc1=O]

In an exemplary embodiment, R may be Cl, X may be $CH_2$, n may be 1, A may be C(O), B may be

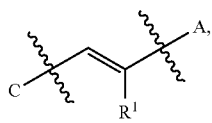

$R^1$ may be H, C may be

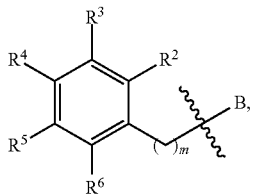

m may be 0, $R^2$, $R^3$, $R^5$, and $R^6$ may be H, and, $R^4$ may be $O(CH_2)_2N(CH_3)_2$.

In an exemplary embodiment, R may be Br, X may be $CH_2$, n may be 1, A may be C(O), B may be

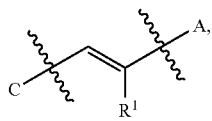

$R^1$ may be H, C may be

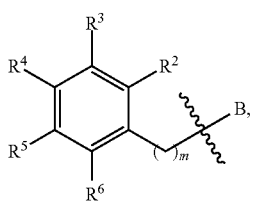

m may be 0, $R^2$, $R^3$, $R^5$, and $R^6$ may be H, and, $R^4$ may be $O(CH_2)_2N(CH_3)_2$.

In an exemplary embodiment, R may be Cl, X may be $CH_2$, n may be 1, A may be $S(O)_2$, B may be

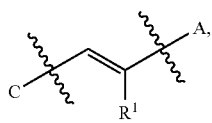

$R^1$ may be H, C may be

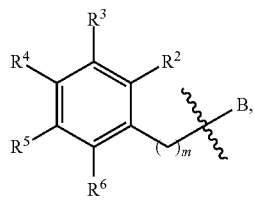

m may be 0, $R^2$, $R^3$, $R^4$, $R^5$, and $R^6$ may be H.

In an exemplary embodiment, R may be Br, X may be $CH_2$, n may be 1, A may be $S(O)_2$, B may be

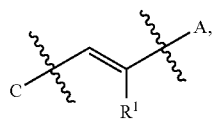

$R^1$ may be H, C may be

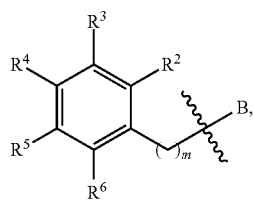

m may be 0, $R^2$, $R^3$, $R^4$, $R^5$, and $R^6$ may be H.

In an exemplary embodiment, R may be Cl, X may be $CH_2$, n may be 2, A may be C(O), B may be

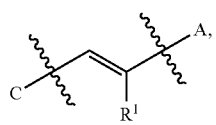

$R^1$ may be H, C may be

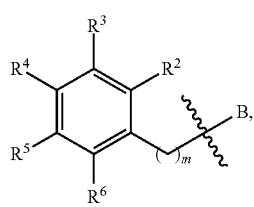

m may be 0, $R^2$, $R^3$, $R^5$, and $R^6$ may be H, and, $R^4$ may be $O(CH_2)_2N(CH_3)_2$.

In an exemplary embodiment, R may be Br, X may be $CH_2$, n may be 2, A may be C(O), B may be

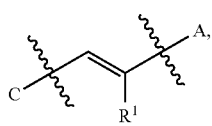
R¹ may be H, C may be
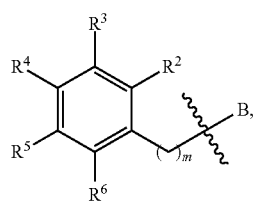
m may be 0, R², R³, R⁵, and R⁶ may be H, and, R⁴ may be O(CH₂)₂N(CH₃)₂.
In exemplary embodiments, a compound of the disclosure comprises Formula (I) as shown below:
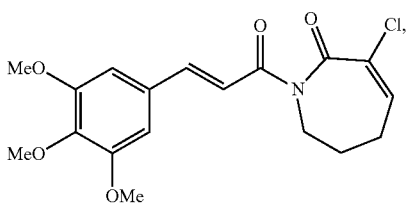
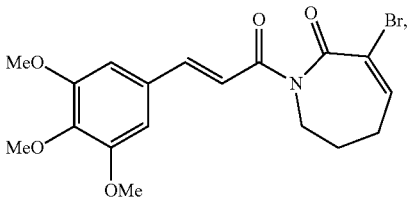
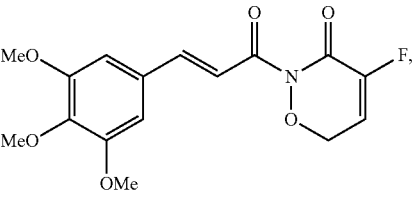 [SMILES: COc1cc(/C=C/C(=O)N2CCC=C(Cl)C2=O)cc(OC)c1OC]
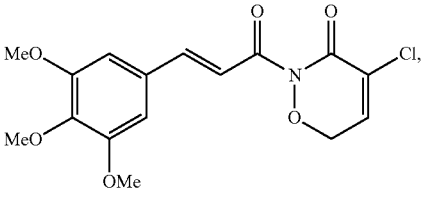
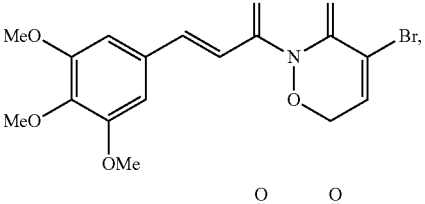
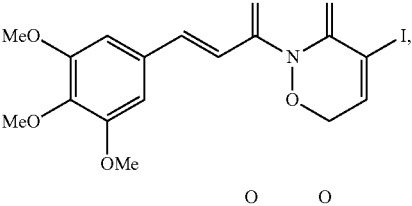
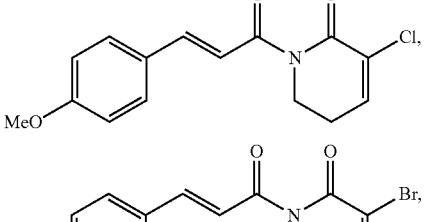
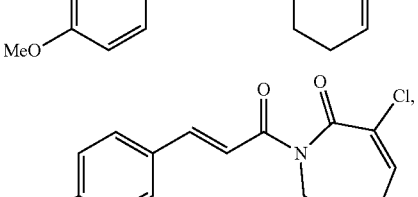

-continued

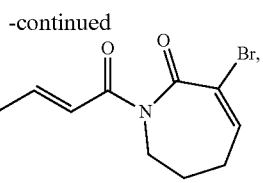
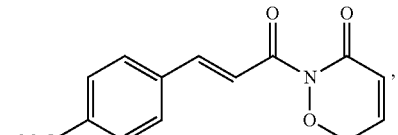
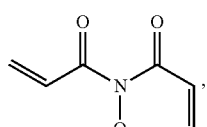
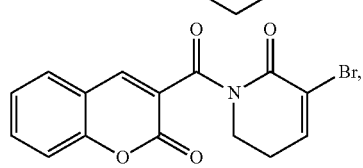
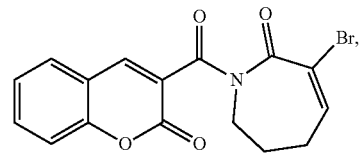
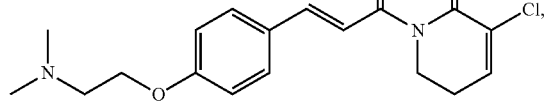
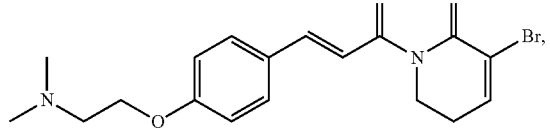
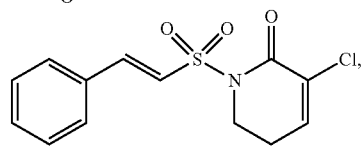
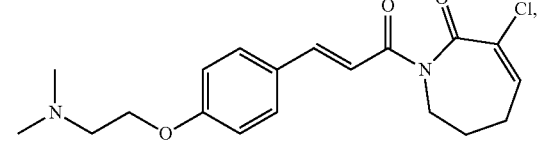
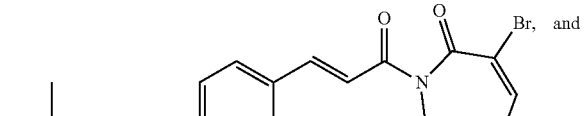
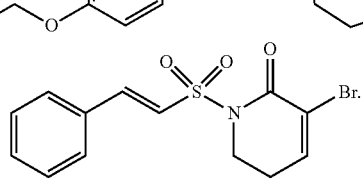

Dosages of a compound of Formula (I) can vary between wide limits, depending upon the disease or disorder to be treated, the age and condition of the subject to be treated. In an embodiment where a composition comprising a compound of Formula (I) is contacted with a sample, the concentration of a compound of Formula (I) may be from about 1 µM to about 40 µM. Alternatively, the concentration of a compound of Formula (I) may be from about 5 µM to about 25 µM. For example, the concentration of a compound of Formula (I) may be about 1, about 2.5 about 5, about 6, about 7, about 8, about 9, about 10, about 11, about 12, about 13, about 14, about 15, about 16, about 17, about 18, about 19, about 20, about 21, about 22, about 23, about 24, about 25, about 30, about 35, or about 40 µM. Additionally, the concentration of a compound of Formula (I) may be greater than 40 µM. For example, the concentration of a compound of Formula (I) may be about 40, about 45, about 50, about 55, about 60, about 65, about 70, about 75, about 80, about 85, about 90, about 95, or about 100 µM.

In an embodiment where the composition comprising a compound of Formula (I) is administered to a subject, the dose of a compound of Formula (I) may be from about 0.1 mg/kg to about 500 mg/kg. For example, the dose of a compound of Formula (I) may be about 0.1 mg/kg, about 0.5 mg/kg, about 1 mg/kg, about 5 mg/kg, about 10 mg/kg, about 15 mg/kg, about 20 mg/kg, or about 25 mg/kg. Alternatively, the dose of a compound of Formula (I) may be about 25 mg/kg, about 50 mg/kg, about 75 mg/kg, about 100 mg/kg, about 125 mg/kg, about 150 mg/kg, about 175 mg/kg, about 200 mg/kg, about 225 mg/kg, or about 250 mg/kg. Additionally, the dose of a compound of Formula (I) may be about 300 mg/kg, about 325 mg/kg, about 350 mg/kg, about 375 mg/kg, about 400 mg/kg, about 425 mg/kg, about 450 mg/kg, about 475 mg/kg or about 500 mg/kg.

(b) Additional Senolytic Agents

A composition of the invention may optionally comprise one or more additional drug or therapeutically active agent in addition to the PL or PL derivative. In some embodiments, the additional drug or therapeutically active agent is a senolytic agent. A senolytic agent as used herein is an agent that "selectively" (preferentially or to a greater degree) destroys, kills, removes, or facilitates selective destruction of senescent cells. In other words, the senolytic agent destroys or kills a senescent cell in a biologically, clinically, and/or statistically significant manner compared with its capability to destroy or kill a non-senescent cell. A senolytic agent is used in an amount and for a time sufficient that selectively kills established senescent cells but is insufficient to kill (destroy, cause the death of) a non-senescent cell in a clinically significant or biologically significant manner. In certain embodiments, where a composition of the invention comprises one or more additional senolytic agents, the additional senolytic agents as described herein alter at least one signaling pathway in a manner that induces (initiates, stimulates, triggers, activates, promotes) and results in (i.e., causes, leads to) death of the senescent cell. The additional senolytic agent may alter, for example, either or both of a cell survival signaling pathway (e.g., Akt pathway) or an inflammatory pathway, for example, by antagonizing a protein within the cell survival and/or inflammatory pathway in a senescent cell. Methods to determine if a compound selectively kills senescent cells are known in the art. For example, see Section II(b) and Section II(c).

In an embodiment, the composition further comprises at least one senolytic agent in addition to the PL or PL derivative. For example, the composition may further comprise 1, 2, 3, 4, 5, or more senolytic agents. Each senolytic agent of the composition may target the same or different signaling pathway. Senolytic agents described herein that may alter at least one signaling pathway include an agent that inhibits an activity of at least one of the target proteins within the pathway. Additional senolytic agents can be administered concurrently or sequentially.

(i) Bcl-2 Inhibitor

In an aspect, the composition further comprises at least one inhibitor of one or more anti-apoptotic proteins in the Bcl-2 family. As used herein, a "Bcl-2 inhibitor" includes at least one inhibitor of one or more anti-apoptotic proteins in the Bcl-2 family. Specifically, a Bcl-2 inhibitor of the invention selectively kills senescent cells. Methods to determine if a compound inhibits one or more anti-apoptotic proteins in the Bcl-2 family are known in the art. For example, nucleic acid expression, protein expression, or activity of Bcl-2 family proteins may be measured as described in detail below. Non-limiting examples of anti-apoptotic Bcl-2 family proteins may include Bcl-2, Bcl-xl, Bcl-w, Mcl-1, Bfl1/A-1, and Bcl-B.

Inhibitors of one or more anti-apoptotic proteins in the Bcl-2 family may promote cell death by antagonizing the pro-survival function of the Bcl-2 protein family thereby inducing apoptosis. A composition of the invention may inhibit one or more anti-apoptotic proteins in the Bcl-2 family. An inhibitor of one or more anti-apoptotic proteins in the Bcl-2 family may be an inhibitor that inhibits nucleic acid expression, protein expression, or protein function of a Bcl-2 family protein. In an embodiment, an inhibitor may affect nucleic acid or protein expression of a Bcl-2 family protein. Non-limiting examples of inhibitors that decrease nucleic acid and protein expression may include histone deacetylase inhibitors such as sodium butyrate and depsipeptide, synthetic cytotoxic retinoid such as fenretinide, and cyclin-dependent kinase inhibitors such as flavopiridol. Alternatively, an inhibitor may be an antisense molecule. For example, oblimersen sodium (G3139) is a Bcl-2 antisense that targets BCL-2 mRNA. In another embodiment, an inhibitor may be a natural inhibitor of Bcl-2 family interactions. For example, progidiosin molecules (bypyrrole-containing natural products), such as GX15-070 (obatoclax) may inhibit Bcl-2 family proteins such as Bcl-2, Bcl-xl, Bcl-w and Mcl-1. Additionally, the natural inhibitor gossypol (AT-101) and its derivatives, apogossypolone, TW37 and TM-1206, may inhibit Bcl-2 family proteins such as Bcl-2, Bcl-xl, and Mcl-1. In still another embodiment, an inhibitor may be designed to bind the hydrophobic grove of anti-apoptotic Bcl-2 family proteins in place of BH3-only proteins (i.e., BH3-mimetics). As such, an inhibitor may be a small molecule inhibitor of one or more anti-apoptotic proteins in the Bcl-2 family. For example, isoxazolidine-based small molecules that interact with Bcl-2 and Bcl-xl, ABT-737 and ABT-263 (navitoclax) that bind Bcl-2, Bcl-xl, and Bcl-w. Non-limiting examples of other Bcl-2 family inhibitors may include SAHB$_A$, terphenyl, benzoylureas, A-385358, A-874009, A-1155463, A-1331852, apogossypolone, BM-1074, BM-1197, BXI-72, HA-14, antimycin A, ABT199, WEH1539, MIM-1, and BH$_3$Is. In a specific embodiment, an inhibitor is a molecule similar to ABT-263. In an exemplary embodiment, an inhibitor of one or more anti-apoptotic proteins in the Bcl-2 family is ABT-263 (navitoclax).

In an aspect, a composition of the invention further comprises ABT-263 or an ABT-263 derivative. ABT-263 or ABT-263 derivatives may be modified to improve bioavailability, solubility, stability, handling properties, or a combination thereof, as compared to an unmodified version. Thus, in another aspect, a composition of the invention may further comprise modified ABT-263 or ABT-263 derivative. In still another aspect, a composition of the invention further comprises a prodrug of ABT-263 or an ABT-263 derivative.

(ii) Small Molecules

Additional senolytic agents that may be used in a composition of the invention include small organic molecules. Small organic molecules (also called small molecules or small molecule compounds herein) typically have molecular weights less than $10^5$ daltons, less than $10^4$ daltons, or less than $10^3$ daltons. In certain embodiments, a small molecule senolytic agent does not violate the following criteria more than once: (1) no more than 5 hydrogen bond donors (the total number of nitrogen-hydrogen and oxygen-hydrogen bonds); (2) not more than 10 hydrogen bond acceptors (all nitrogen or oxygen atoms); (3) a molecular mass less than 500 daltons; (4) an octanol-water partition coefficient[5] log P not greater than 5.

(iii) MDM2 Inhibitors

In certain embodiments, the additional senolytic agent may be an MDM2 inhibitor. An MDM2 (murine double minute 2) inhibitor that may be used in a composition of the invention may be a small molecule compound that belongs to any one of the following classes of compounds, for example, a cis-imidazoline compound, a spiro-oxindole compound, a benzodiazepine compound, a piperidinone compound, a tryptamine compound, and CGM097, and related analogs. In certain embodiments, the MDM2 inhibitor is also capable of binding to and inhibiting an activity of MDMX (murine double minute X, which is also known as HDMX in humans). The human homolog of MDM2 is called HDM2 (human double minute 2) in the art. Therefore, when a subject treated by the methods described herein is a human subject, the compounds described herein as MDM2 inhibitors also inhibit binding of HDM2 to one or more of its ligands.

(vi) Akt Kinase Inhibitors

In certain embodiments the additional senolytic agent is an Akt Kinase inhibitor. For example, an additional senolytic agent can be a small molecule compound and analogs thereof that inhibits Akt. In some embodiments, the additional senolytic agent is a compound that selectively inhibits Akt1, Akt2, and Akt3, relative to other protein kinases.

Akt inhibitors (which may also be called Akt kinase inhibitors or AKT kinase inhibitors) can be divided into six major classes based on their mechanisms of action (see, e.g., Bhutani et al., Infectious Agents and Cancer 2013, 8:49 doi:10.1186/1750-9378-8-49). Akt is also called protein kinase B (PKB) in the art. The first class contains ATP competitive inhibitors of Akt and includes compounds such as CCT128930 and GDC-0068, which inhibit Akt2 and Akt1. This category also includes the pan-Akt kinase inhibitors such as GSK2110183 (afuresertib), GSK690693, and AT7867. The second class contains lipid-based Akt inhibitors that act by inhibiting the generation of PIP3 by PI3K. This mechanism is employed by phosphatidylinositol analogs such as Calbiochem Akt Inhibitors 1, 11 and III or other PI3K inhibitors such as PX-866. This category also includes compounds such as Perifosine (KRX-0401) (Aeterna Zentaris/Keryx). The third class contains a group of compounds called pseudosubstrate inhibitors. These include compounds such as AKTide-2 T and FOXO3 hybrid. The fourth class consists of allosteric inhibitors of AKT kinase domain, and include compounds such as MK-2206 (8-[4-(1-aminocyclobutyl)phenyl]-9-phenyl-2H-[1,2,4]triazolo[3,4-f][1,6]n-aphthyridin-3-one:dihydrochloride) (Merck & Co.) see, e.g., U.S. Pat. No. 7,576,209). The fifth class consists of antibodies and include molecules such as GST-anti-Akt1-MTS.

The last class comprises compounds that interact with the PH domain of Akt, and includes Triciribine and PX-316. Other compounds described in the art that act as AKT inhibitors include, for example, GSK-2141795 (GlaxoSmithKline), VQD-002, miltefosine, AZD5363, GDC-0068, and API-1. Techniques for determining the activity of AKT inhibitors are routinely practiced by persons skilled in the art.

(v) Polypeptides, Antibodies, and Nucleic Acids

In other certain embodiments, an additional senolytic agent may be a polypeptide, peptide, antibody, antigen-binding fragment (i.e., peptides and polypeptides comprising at least one complementary determining region (CDR)), peptibody, recombinant viral vector, or a nucleic acid. In certain embodiments, an additional senolytic agent is an antisense oligonucleotide, siRNA, shRNA, or a peptide. For example, additional senolytic agents such as polypeptides, antibodies, nucleic acids, and the like, include, for example, MDM2 inhibitors, BCL-2 family inhibitors, or Akt kinase inhibitors. In other embodiments, polypeptides, peptides, antibodies (including antigen-binding fragments thereof) that specifically bind to a ligand or target protein of a small molecule senolytic agent described herein, may be used.

(vi) Dosage

Dosages of an additional senolytic agent can vary between wide limits, depending upon the disease or disorder to be treated, the age and condition of the subject to be treated. In an embodiment where the composition further comprising at least one additional senolytic agent is contacted with a sample, the concentration of the at least one additional senolytic agent may be from about 0.01 µM to about 10 µM. Alternatively, the concentration of the at least one additional senolytic agent may be from about 0.01 µM to about 5 µM. For example, the concentration of the at least one additional senolytic agent may be about 0.01, about 0.05, about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, or about 10 µM. Additionally, the concentration of the at least one additional senolytic agent be greater than 10 µM. For example, the concentration of the at least one additional senolytic agent may be about 10, about 15, about 20, about 25, about 30, about 35, about 40, about 45, about 50, about 55, about 60, about 65, about 70, about 75, about 80, about 85, about 90, about 95, or about 100 µM.

In an embodiment where the composition further comprising at least additional senolytic agent is administered to a subject, the dose of inhibitor may be from about 0.1 mg/kg to about 500 mg/kg. For example, the dose of the least one additional senolytic agent may be about 0.1 mg/kg, about 0.5 mg/kg, about 1 mg/kg, about 5 mg/kg, about 10 mg/kg, about 15 mg/kg, about 20 mg/kg, or about 25 mg/kg. Alternatively, the dose of the least one i additional senolytic agent may be about 25 mg/kg, about 50 mg/kg, about 75 mg/kg, about 100 mg/kg, about 125 mg/kg, about 150 mg/kg, about 175 mg/kg, about 200 mg/kg, about 225 mg/kg, or about 250 mg/kg. Additionally, the dose of the least one additional senolytic agent may be about 300 mg/kg, about 325 mg/kg, about 350 mg/kg, about 375 mg/kg, about 400 mg/kg, about 425 mg/kg, about 450 mg/kg, about 475 mg/kg, or about 500 mg/kg.

(c) Components of the Composition

The present disclosure also provides pharmaceutical compositions. The pharmaceutical composition comprises a compound of Formula (I), as an active ingredient, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

(i) Diluent

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

(ii) Binder

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

(iii) Filler

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

(iv) Buffering Agent

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

(v) pH Modifier

In various embodiments, the excipient may be a pH modifier. By way of non-limiting example, the pH modifying agent may be sodium carbonate, sodium bicarbonate, sodium citrate, citric acid, or phosphoric acid.

(vi) Disintegrant

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

(vii) Dispersant

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

(viii) Excipient

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

(ix) Lubricant

In a further embodiment, the excipient may be a lubricant. Non-limiting examples of suitable lubricants include minerals such as talc or silica; and fats such as vegetable stearin, magnesium stearate, or stearic acid.

(x) Taste-Masking Agent

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

(xi) Flavoring Agent

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

(xii) Coloring Agent

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

(d) Administration (i) Dosage Forms

The composition can be formulated into various dosage forms and administered by a number of different means that will deliver a therapeutically effective amount of the active ingredient. Such compositions can be administered orally (e.g. inhalation), parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. (18$^{th}$ ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration (including subcutaneous, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules, and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols, or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising a compound of Formula (I) is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers, and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of a compound of Formula (I) in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the compound of Formula (I) may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetonitrile, alcohols, dimethylformamide, tetrahydrofuran, or combinations thereof.

Liposomes carrying a compound of Formula (I) may be prepared by any known method of preparing liposomes for drug delivery, such as, for example, detailed in U.S. Pat. Nos. 4,241,046; 4,394,448; 4,529,561; 4,755,388; 4,828, 837; 4,925,661; 4,954,345; 4,957,735; 5,043,164; 5,064, 655; 5,077,211; and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of the compound of Formula (I), concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The compound of Formula (I) may be encapsulated in a microemulsion by any method generally known in the art.

In yet another embodiment, a compound of Formula (I) may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

(II) Methods

The present disclosure encompasses a method of selectively killing one or more cancer cells or senescent cells in a sample, the method comprising contacting a composition comprising an effective amount a compound of Formula (I). In another aspect, the present disclosure encompasses a method of selectively killing one or more cancer cells or senescent cells in a subject in need thereof, the method comprising administering to the subject a composition comprising a therapeutically effective amount a compound of Formula (I).

By selectively killing one or more cancer cells or senescent cells is meant a composition of the invention does not appreciably kill normal or non-senescent cells at the same concentration. Accordingly, the median lethal dose or LD50 of the inhibitor in normal or non-senescent cells may be about 5 to about 50 times higher than the LD50 of the inhibitor in cancer or senescent cells. As used herein, the LD50 is the concentration of inhibitor required to kill half the cells in the cell sample. For example, the LD50 of the inhibitor in normal or non-senescent cells may be greater than about 5, about 6, about 7, about 8, about 9 or about 10 times higher than the LD50 of the inhibitor in cancer or senescent cells. Alternatively, the LD50 of the inhibitor in normal or non-senescent cells may be greater than about 10, about 15, about 20, about 25, about 30, about 35, about 40, about 45, or about 50 times higher than the LD50 of the inhibitor in cancer or senescent cells. Additionally, the LD50 of the inhibitor in non-senescent cells may be greater than 50 times higher than the LD50 of the inhibitor in cancer or senescent cells. In a specific embodiment, the LD50 of the inhibitor in normal or non-senescent cells is greater than 10 times higher than the LD50 of the inhibitor in cancer or senescent cells. In another specific embodiment, the LD50 of the inhibitor in normal or non-senescent cells is greater than 20 times higher than the LD50 of the inhibitor in cancer or senescent cells.

The progression from an actively dividing cell to a metabolically active, non-dividing cell is termed "senescence" or "cellular senescence." As used herein, the terms "senescence" and "cellular senescence" may be used interchangeably. The term "senescence" also refers to the state into which cells enter after multiple rounds of division and, as a result of cellular pathways, future cell division is prevented from occurring even though the cell remains metabolically active. Senescent cells may differ from their pre-senescent counterparts in one or more of the following ways: 1) they arrest growth and cannot be stimulated to reenter the cell cycle by physiological mitogens; 2) they become resistant to apoptotic cell death; and/or 3) they acquire altered differentiated functions.

In contrast to cancer cells which grow and divide uncontrollably, the ability of most differentiated eukaryotic cells to proliferate is finite. Stated another way, normal cells have an intrinsically determined limit to the number of cell divisions through which they can proceed. This phenomenon has been termed "replicative cellular senescence" and is an intrinsic anticancer mechanism that limits a cell's proliferative ability, thereby preventing neoplastic transformation. Another form of senescence is "premature cellular senescence." Premature cellular senescence, like replicative cellular senescence, is a terminal fate of mitotic cells, characterized by permanent cell cycle arrest. Unlike replicative cellular senescence, however, premature cellular senescence does not require telomere deterioration and can be induced by a variety of stressors including, but not limited to, ultraviolet light, reactive oxygen species, chemotherapeutics, environmental toxin, cigarette smoking, ionizing radiation, distortion of chromatin structure, excessive mitogenic signaling, and oncogenic mutations. Still another form of senescence is therapy-induced senescence (TIS) which refers to the phenomenon of a subset of tumor cells being forced into a senescent state by therapeutic agents. TIS is known to develop because of certain treatments, including radiotherapy and chemotherapy.

The number of senescent cells in various organs and tissues of a subject increases with age. The accumulation of senescent cells may drive the deterioration that underlies aging and age-related diseases. For example, the accumulation of senescent cells in aged tissue may contribute to age-associated tissue dysfunction, reduced regenerative capacity, and disease. In this context, senescence is considered deleterious because it contributes to decrements in tissue renewal and function. As a non-limiting example, an aged tissue may lack the ability to respond to stress when proliferation is required thereby resulting in the reduced fitness seen with aging. A key component of this model is that substantial numbers of senescent cells should be present in tissues with aging, without, or prior to, pathology.

(a) Senescent Cells

A senescent cell may be a cell that ceases to divide but remains metabolically active. The non-dividing cells may remain viable for many weeks, but fail to grow/replicate DNA despite the presence of ample space, nutrients, and growth factors in the medium. Thus, the senescence growth arrest is essentially permanent because senescent cells cannot be stimulated to proliferate by known physiological stimuli. Further, a senescent cell of the invention may be resistant to certain apoptotic signals and may acquire widespread changes in gene expression. The resistance to apoptosis may explain the increase in senescent cells with age. Manipulation of pro- and anti-apoptotic proteins may cause cells that are destined to die by apoptosis to senesce and, conversely, cause cells that are destined to senesce to undergo apoptosis.

A senescent cell of the invention may be senescent due to replicative cellular senescence, premature cellular senescence or therapy-induced senescence. Senescent cells that are senescent due to replication may have undergone greater than 60 population doublings. Alternatively, senescent cells that are senescent due to replication may have undergone greater than 40, greater than 50, greater than 60, greater than 70, or greater than 80 population doublings. A senescent cell that is prematurely cellular senescent may be induced by, but not limited to, ultraviolet light, reactive oxygen species, chemotherapeutics, environmental toxin, cigarette smoking, ionizing radiation, distortion of chromatin structure, excessive mitogenic signaling, and oncogenic mutations. In a specific embodiment, premature cellular senescence may be induced by ionizing radiation (IR). In another specific embodiment, premature cellular senescence may also be induced by ectopic transfection with Ras oncogene. A senescent cell that is therapy-induced senescent may have been exposed to DNA-damaging therapy.

A senescent cell of the invention may generally be a eurkaryotic cell. Non-limiting examples of senescent cells may include, but are not limited to, mammary epithelial cells, keratinocytes, cardiac myocytes, chondrocytes, endothelial cells (large vessels), endothelial cells (microvascular), epithelial cells, fibroblasts, follicle dermal papilla cells, hepatocytes, melanocytes, osteoblasts, preadipocytes, primary cells of the immune system, skeletal muscle cells, smooth muscle cells, adipocytes, neurons, glial cells, contractile cells, exocrine secretory epithelial cells, extracellular matrix cells, hormone secreting cells, keratinizing epithelial cells, islet cells, lens cells, mesenchymal stem cells, pancreatic acinar cells, paneth cells of the small intestine, primary cells of hemopoietic linage, primary cells of the nervous system, sense organ and peripheral neuron supporting cells, wet stratified barrier epithelial cells and stem cells. In a specific embodiment, the stem cells are adult stem cells. Adult stem cells are stem cells which maintain and repair the tissue in which they are found and are generally referred to by their tissue of origin. Non-limiting examples of adult stem cells include muscle stem cells, hematopoietic stem cells, heart stem cells, neural stem cells, mesenchymal stem cells, intestinal stem cells, skin stem cells, adipose-derived stem cells, endothelial stem cells, and dental pulp stem cells. In a specific embodiment, a senescent cell of the invention is a fibroblast. In another specific embodiment, a senescent cell may be a hematopoietic stem cell.

Further, a senescent cell of the invention may be found in renewable tissues, including the vasculature, hematopoietic system, epithelial organs, and the stroma. A senescent cell of the invention may also be found at sites of aging or chronic age-related pathology, such as osteoarthritis and atherosclerosis. Further, a senescent cell of the invention may be associated with benign dysplastic or preneoplastic lesions and benign prostatic hyperplasia. In an embodiment, a senescent cell of the invention may be found in normal and tumor tissues following DNA-damaging therapy. In a specific embodiment, a senescent cell may be found at a site of aging or age-related pathology.

An age-related pathology may include any disease or condition which is fully or partially mediated by the induction or maintenance of a non-proliferating or senescent state in a cell or a population of cells in a subject. Non-limiting examples include age-related tissue or organ decline which may lack visible indication of pathology, or overt pathology such as a degenerative disease or a function-decreasing disorder. For example, Alzheimer's disease, Parkinson's disease, cataracts, macular degeneration, glaucoma, atherosclerosis, acute coronary syndrome, myocardial infarction, stroke, hypertension, idiopathic pulmonary fibrosis (IPF), chronic obstructive pulmonary disease (COPD), osteoarthritis, type 2 diabetes, obesity, fat dysfunction, coronary artery disease, cerebrovascular disease, periodontal disease, and cancer treatment-related disability such as atrophy and fibrosis in various tissues, brain and heart injury, and therapy-related myelodysplastic syndromes. Additionally, an age-related pathology may include an accelerated aging disease such as progeroid syndromes (i.e. Hutchinson-Gilford progeria syndrome, Werner syndrome, Bloom syndrome, Rothmund-Thomson Syndrome, Cockayne syndrome, xeroderma pigmentosum, trichothiodystrophy, combined xeroderma pigmentosum-Cockayne syndrome, restrictive dermopathy), ataxia telangiectasia, Fanconi anemia, Friedreich's ataxia, dyskeratosis congenital, aplastic anemia, IPF, and others. A method of identifying an age-related disease or condition as described herein may include detecting the presence of senescent cells.

(b) Detecting Senescent Cells

In an aspect, a method of the invention may comprise detecting senescent cells. Senescent cells may be detected in vivo or in vitro. Suitable markers for detecting senescent cells in vitro and in vivo are known in the art. For example, methods to detect senescent cells may include, but are not limited to, detecting lack of DNA replication by incorporation of a DNA-staining reagent (e.g., 5-bromodeoxyuridine (BrdU), $^3$H-thymidine), immunostaining for proteins such as proliferating cell nuclear antigen (PCNA) and Ki-67, histochemical staining for senescence-associated β-galactosidase (SA-β-gal), detecting expression of p16, p19, Pail, Igfbp2, IL-6, Mmp13, Nrg1, differentiated embryo-chondrocyte expressed-1 (DEC1), p15 (a CDK1) and decoy death receptor-2 (DCR2), detecting cytological markers such as senescence-associated heterochromatin foci (SAHFs) and senescence-associated DNA-damage foci (SDFs). SAHFs may be detected by the preferential binding of DNA dyes, such as 4',6-diamidino-2-phenylindole (DAPI), and the presence of certain heterochromatin-associated histone modifications (for example, H3 Lys9 methylation) and proteins (for example, heterochromatin protein-1 (HP1)). Additionally, senescent cells may be detected as described in U.S. Pat. No. 5,491,069 and US Patent Application No. 2010/0086941. In certain embodiments, senescent cells are detected by histochemical staining for SA-β-gal.

In certain embodiments, one or more senescent cells are detected in a sample. A sample may be a cell sample, a tissue sample, or a biopsy from a subject. Generally speaking, a sample may be dependent on the age-related pathology. For instance, a sample may be tissue biopsy material. As such, a tissue sample may be from esophagus, stomach, liver, gallbladder, pancreas, adrenal glands, bladder, gallbladder, large intestine, small intestine, kidneys, liver, pancreas, colon, stomach, thymus, spleen, brain, spinal cord, nerves, adipose tissue, heart, lungs, eyes, corneal, skin or islet tissue or organs. In a specific embodiment, a tissue sample may be from lung, skeletal muscle, and brain. In another specific embodiment, a tissue sample may be from liver and heart. Alternatively, a sample may be a cell sample. As such, a cell sample may be oocytes and/or spermatozoa, mesenchymal stem cells, adipocytes, central nervous system neurons and glial cells, contractile cells, exocrine secretory epithelial cells, extracellular matrix cells, hormone secreting cells, keratinizing epithelial cells, islet cells, kidney cells, lens cells, pancreatic acinar cells, paneth cells of small intestine, primary cells of hemopoietic lineage, primary cells of the nervous system, sense organ and peripheral neuron supporting cells or wet stratified barrier epithelial cells. Detection of senescent cells may be used to assess the replicative history of tissues, thereby providing a method for evaluation of the physiological, in contrast to the chronological age of the tissue.

The number of senescent cells may increase with age. The number of senescent cells in a tissue or sample may be from less than 1% to greater than 15%. In an embodiment, the number of senescent cells in a tissue or sample may be less than 1%, less than 2%, less than 3%, less than 4%, or less than 5%. In another embodiment, the number of senescent cells in a tissue or sample may be about 5%, about 6%, about 7%, about 8%, about 9%, or about 10%. In still another embodiment, the number of senescent cells in a tissue or sample may be greater than 10%, greater than 11%, greater than 12%, greater than 13%, greater than 14%, or greater than 15%.

(c) Measuring Cell Death

In an aspect, a method of the invention may comprise measuring cell death of senescent cells. Methods of measuring cell death are known in the art. For example, cell death may be measured by Giemsa staining, trypan blue exclusion, acridine orange/ethidium bromide (AO/EB) double staining for fluorescence microscopy and flow cytometry, propidium iodide (PI) staining, annexin V assay, TUNEL assay, DNA ladder, LDH activity, and MTT assay. In a preferred embodiment, cell death is due to induction of apoptosis. Cell death due to induction of apoptosis may be measured by observation of morphological characteristics including cell shrinkage, cytoplasmic condensation, chromatin segregation and condensation, membrane blebbing, and the formation of membrane-bound apoptotic bodies. Cell death due to induction of apoptosis may be measured by observation of biochemical hallmarks including internucleosomal DNA cleavage into oligonucleosome-length fragments. Traditional cell-based methods of measuring cell death due to induction of apoptosis include light and electron microscopy, vital dyes, and nuclear stains. Biochemical methods include DNA laddering, lactate dehydrogenase enzyme release, and MTT/XTT enzyme activity. Additionally, terminal deoxynucleotidyl transferase-mediated dUTP-biotin nick end labeling of DNA fragments (TUNEL) and in situ end labeling (ISEL) techniques are used, which when used in conjunction with standard flow cytometric staining methods yield informative data relating cell death to various cellular parameters, including cell cycle and cell phenotype. See Loo and Rillema, Methods Cell Biol. 1998,57:251-64, which is incorporated herein by reference, for a review of these methods. In an exemplary embodiment, cell death due to apoptosis may be measured by the reduction of pro-caspase-3. Caspase-3 has been implicated as an "effector" caspase associated with the initiation of the "death cascade" and is therefore an important marker of the cell's entry point into the apoptotic signaling pathway. Caspase-3 is activated by the upstream caspase-8 and caspase-9, and since it serves as a convergence point for different signaling pathways, it is well suited as a read-out in an apoptosis assay.

The results of these methods may be used to determine the percentage of viable cells. In a preferred embodiment, cell death may be measured as a reduction in viable cells. Since a composition of the invention selectively kills senescent cells, a reduction in viable cells is indicative of a reduction in senescent cells. As described in Section II(b), the number of senescent cells in a sample may be from less than 1% to greater than 15%. As such, a reduction in viable cells following administration of an inhibitor of the invention may be greater than 15% to less than 1%. For example, the reduction in viable cells may be less than 1%, less than 2%, less than 3%, less than 4%, or less than 5%. Alternatively, the reduction in viable cells may be about 5%, about 6%, about 7%, about 8%, about 9%, or about 10%. Additionally, the reduction in viable cells may be greater than 10%, greater than 11%, greater than 12%, greater than 13%, greater than 14%, or greater than 15%.

(d) Administration

In certain aspects, a therapeutically effective amount of a composition of the invention may be administered to a subject. Administration is performed using standard effective techniques, including peripherally (i.e. not by administration into the central nervous system) or locally to the central nervous system. Peripheral administration includes but is not limited to oral, inhalation, intravenous, intraperitoneal, intra-articular, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation. The route of administration may be dictated by the disease or condition to be treated. For example, if the disease or condition is COPD or IPF, the composition may be administered via inhalation. Alternatively, is the disease or condition is osteoarthritis, the composition may be administered via intra-articular invention. It is within the skill of one in the art, to determine the route of administration based on the disease or condition to be treated. In a specific embodiment, a composition of the invention is administered orally.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents, and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

For therapeutic applications, a therapeutically effective amount of a composition of the invention is administered to a subject. A "therapeutically effective amount" is an amount of the therapeutic composition sufficient to produce a measurable response (e.g., cell death of senescent cells, an anti-aging response, an improvement in symptoms associated with a degenerative disease, or an improvement in symptoms associated with a function-decreasing disorder). Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, age, the age-related disease or condition, the degenerative disease, the function-decreasing disorder, the symptoms, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

The frequency of dosing may be daily or once, twice, three times, or more per week or per month, as needed as to effectively treat the symptoms. The timing of administration of the treatment relative to the disease itself and duration of treatment will be determined by the circumstances surrounding the case. Treatment could begin immediately, such as at the site of the injury as administered by emergency medical personnel. Treatment could begin in a hospital or clinic itself, or at a later time after discharge from the hospital or after being seen in an outpatient clinic. Duration of treatment could range from a single dose administered on a one-time basis to a life-long course of therapeutic treatments.

Typical dosage levels can be determined and optimized using standard clinical techniques and will be dependent on the mode of administration.

(e) Subject

A subject may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the subject is a human.

The human subject may be of any age. However, since senescent cells are normally associated with aging, a human subject may be an older human subject. In some embodiments, the human subject may be about 30, 35, 40, 45, 50, 55, 60, 65, 70, 75, 80, 85, 90, 95 years of age or older. In some preferred embodiments, the human subject is 30 years of age or older. In other preferred embodiments, the human subject is 40 years of age or older. In other preferred embodiments, the human subject is 45 years of age or older. In yet other preferred embodiments, the human subject is 50 years of age or older. In still other preferred embodiments, the human subject is 55 years of age or older. In other preferred embodiments, the human subject is 60 years of age or older. In yet other preferred embodiments, the human subject is 65 years of age or older. In still other preferred embodiments, the human subject is 70 years of age or older. In other preferred embodiments, the human subject is 75 years of age or older. In still other preferred embodiments, the human subject is 80 years of age or older. In yet other preferred embodiments, the human subject is 85 years of age or older. In still other preferred embodiments, the human subject is 90 years of age or older.

Additionally, a subject in need thereof may be a subject suffering from an age-related disease or condition as described below.

(f) Aging and Age-Related Diseases

It has been demonstrated that senescent cells drive age-related pathologies and that selective elimination of these cells can prevent or delay age-related deterioration. Thus, senescent cells may be therapeutic targets in the treatment of aging and age-related disease. As such, removal of senescent cells may delay tissue dysfunction and extend health span. Clearance of senescent cells is expected to improve tissue milieu, thereby improving the function of the remaining non-senescent cells.

The present disclosure provides a method for delaying at least one feature of aging in a subject, the method comprising administering a a composition comprising a therapeutically effective amount of a compound of Formula (I) to a subject. As used herein, "a feature of aging" may include, but is not limited to, systemic decline of the immune system, muscle atrophy and decreased muscle strength, decreased skin elasticity, delayed wound healing, retinal atrophy, reduced lens transparency, reduced hearing, osteoporosis, sarcopenia, hair graying, skin wrinkling, poor vision, frailty, and cognitive impairment.

In an aspect, a composition of in the invention selectively kills senescent cells. In this way, targeting senescent cells during the course of aging may be a preventative strategy. Accordingly, administration of a composition comprising a therapeutically effective amount of a compound of Formula (I) to a subject may prevent comorbidity and delay mortality in an older subject. Further, selective killing of senescent cells may boost the immune system, extend the health span, and improve the quality of life in a subject. Additionally, selective killing of senescent cells may delay sarcopenia. Sarcopenia is the degenerative loss of skeletal muscle mass, quality, and strength associated with aging. As such, a delay in sarcopenia may reduce frailty, reduce risk of falling, reduce fractures, and reduce functional disability in a subject. Furthermore, selective killing of senescent cells may delay aging of the skin. Aged skin has increased wrinkles, decreased immune barrier function and increased susceptibility to skin cancer and trauma. As such, selective killing of senescent cells may delay skin wrinkling, delay the onset of decreased immune barrier function and decrease susceptibility to skin cancer and trauma in a subject. Selective killing of senescent cells may also delay the onset of retinal atrophy and reduced lens transparency as measured by vision tests.

Methods of measuring aging are known in the art. For example, aging may be measured in the bone by incident non-vertebral fractures, incident hip fractures, incident total fractures, incident vertebral fractures, incident repeat fractures, functional recovery after fracture, bone mineral density decrease at the lumbar spine and hip, rate of knee buckling, NSAID use, number of joints with pain, and osteoarthritis. Aging may also be measured in the muscle by functional decline, rate of falls, reaction time and grip strength, muscle mass decrease at upper and lower extremities, and dual tasking 10-meter gait speed. Further, aging may be measured in the cardiovascular system by systolic and diastolic blood pressure change, incident hypertension, and major cardiovascular events such as myocardial infarction, stroke, congestive heart disease, and cardiovascular mortality. Additionally, aging may be measured in the brain by cognitive decline, incident depression, and incident dementia. Also, aging may be measured in the immune system by rate of infection, rate of upper respiratory infections, rate of flu-like illness, incident severe infections that lead to hospital admission, incident cancer, rate of implant infections, and rate of gastrointestinal infections. Other indications of aging may include, but not limited to, decline in oral health, tooth loss, rate of GI symptoms, change in fasting glucose and/or insulin levels, body composition, decline in kidney function, quality of life, incident disability regarding activities of daily living, and incident nursing home admission. Methods of measuring skin aging are known in the art and may include trans-epidermal water loss (TEWL), skin hydration, skin elasticity, area ratio analysis of crow's feet, sensitivity, radiance, roughness, spots, laxity, skin tone homogeneity, softness, and relief (variations in depth).

The present disclosure also provides a method of treating an age-related disease or condition, the method comprising administering a composition comprising a therapeutically effective amount of a compound of Formula (I) to a subject in need thereof, provided the age-related disease or condition is not cancer. As used herein, "age-related disease or condition" may include, but is not limited to, a degenerative disease or a function-decreasing disorder such as Alzheimer's disease, Parkinson's disease, cataracts, macular degeneration, glaucoma, atherosclerosis, acute coronary syndrome, myocardial infarction, stroke, hypertension, idiopathic pulmonary fibrosis (IPF), chronic obstructive pulmonary disease (COPD), osteoarthritis, type 2 diabetes, obesity, fat dysfunction, coronary artery disease, cerebrovascular disease, periodontal disease, cancer treatment-related disability such as atrophy and fibrosis in various tissues, brain and heart injury, and therapy-related myelodysplastic syndromes, and diseases associated with accelerated aging and/or defects in DNA damage repair and telomere maintenance such as progeroid syndromes (i.e. Hutchinson-Gilford progeria syndrome, Werner syndrome, Bloom syndrome, Rothmund-Thomson Syndrome, Cockayne syndrome, xeroderma pigmentosum, trichothiodystrophy, combined xeroderma pigmentosum-Cockayne syndrome, restrictive dermopathy), ataxia telangiectasia, Fanconi anemia, Friedreich's ataxia, dyskeratosis congenital, aplastic anemia, IPF, and others. Methods of diagnosing and identifying an age-related disease or condition are known in the art.

The present disclosure also provides a method of killing therapy-induced senescent cells. The method comprises administering a composition comprising a therapeutically effective amount of a compound comprising Formula (I) to a subject that has received DNA-damaging therapy and killing therapy induced-senescent cells in normal and tumor tissues following DNA-damaging therapy.

Non-limiting examples of DNA-damaging therapy may include γ-irradiation, alkylating agents such as nitrogen mustards (chlorambucil, cyclophosphamide, ifosfamide, melphalan), nitrosoureas (streptozocin, carmustine, lomustine), alkyl sulfonates (busulfan), triazines (dacarbazine, temozolomide) and ethylenimines (thiotepa, altretamine), platinum drugs such as cisplatin, carboplatin, oxalaplatin, antimetabolites such as 5-fluorouracil, 6-mercaptopurine, capecitabine, cladribine. clofarabine, cytarabine, floxuridine, fludarabine, gemcitabine, hydroxyurea, methotrexate, pemetrexed, pentostatin, thioguanine, anthracyclines such as daunorubicin, doxorubicin, epirubicin, idarubicin, anti-tumor antibiotics such as actinomycin-D, bleomycin, mitomycin-C, mitoxantrone, topoisomerase inhibitors such as topoisomerase I inhibitors (topotecan, irinotecan) and topoisomerase II inhibitors (etoposide, teniposide, mitoxantrone), mitotic inhibitors such as taxanes (paclitaxel, docetaxel), epothilones (ixabepilone), *vinca* alkaloids (vinblastine, vincristine, vinorelbine), and estramustine.

Based on the observation that ionizing radiation and various chemotherapeutic agents elicit a marked senescence response in vivo, therapy-induced senescent cells may be a cause of long-term ramifications after DNA-damaging therapy, such as cancer therapy. As such, the systemic accumulation of therapy-induced senescent cells may drive accelerated physical decline in cancer survivors. Accelerated physical decline may also be referred to as accelerated aging. Accordingly, once a tumor is removed by systemic radiation or chemotherapy, senescence may be triggered in a variety of other organs, leading to long-term ramifications for the patient. Long-term ramifications may include reduced quality of life predisposing the subject to disabilities and comorbidities. For example, a subject that has received DNA-damaging therapy may experience a disproportionate decline in physical function, such as inability to walk up stairs or to reach up to put things onto shelves and/or increased functional disabilities such as difficulty, eating, dressing, and maintaining adequate hygiene. Additionally, late effects of ionizing radiation may include long-term bone marrow injury and/or lung fibrosis. Long-term bone marrow injury can promote hypoplastic anemia and/or myelodysplastic syndrome or leukemia. Further, the inventors demonstrated that following ionizing radiation, senescent cells in lung, muscle and brain are greatly increased. These long-term ramifications provide a link between accelerated aging and cancer treatment. A method to measure accelerated aging may be as described in methods of measuring aging as above. Accordingly, administration of a composition comprising an inhibitor of the invention to a subject may prevent accelerated aging in a subject who has received DNA damaging therapy.

Definitions

When introducing elements of the present disclosure or the preferred aspects(s) thereof, the articles "a," "an," "the," and "said" are intended to mean that there are one or more of the elements. The terms "comprising," "including," and "having" are intended to be inclusive and mean that there may be additional elements other than the listed elements.

As used herein, the following definitions shall apply unless otherwise indicated. For purposes of this invention, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry," Thomas Sorrell, University Science Books, Sausalito: 1999, and "March's Advanced Organic Chemistry," 5$^{th}$ Ed., Smith, M. B. and March, J., eds. John Wiley & Sons, New York: 2001, the entire contents of which are hereby incorporated by reference.

The term "alkyl" as used herein alone or as part of a group refers to saturated monovalent hydrocarbon radicals having straight or branched hydrocarbon chains or, in the event that at least 3 carbon atoms are present, cyclic hydrocarbons or combinations thereof and contains 1 to 20 carbon atoms (C$_{1-20}$alkyl), suitably 1 to 10 carbon atoms (C$_{1-10}$alkyl), preferably 1 to 8 carbon atoms (C$_{1-8}$alkyl), more preferably 1 to 6 carbon atoms (C$_{1-4}$alkyl), and even more preferably 1 to 4 carbon atoms (C$_{1-4}$alkyl). Examples of alkyl radicals include methyl, ethyl, propyl, isopropyl, n-butyl, isobutyl, sec-butyl, tert-butyl, pentyl, isoamyl, hexyl, cyclopropyl, cyclobutyl, cyclopentyl, cyclohexyl, and the like.

The term "alkenyl" as used herein alone or as part of a group refers to monovalent hydrocarbon radicals having a straight or branched hydrocarbon chains having one or more double bonds and containing from 2 to about 18 carbon atoms, preferably from 2 to about 8 carbon atoms, more preferably from 2 to about 5 carbon atoms. Examples of suitable alkenyl radicals include ethenyl, propenyl, alkyl, 1,4-butadienyl, and the like.

The term "alkynyl" as used herein alone or as part of a group refers to monovalent hydrocarbon radicals having a straight or branched hydrocarbon chains having one or more triple bonds and containing from 2 to about 10 carbon atoms, more preferably from 2 to about 5 carbon atoms. Examples of alkynyl radicals include ethynyl, propynyl, (propargyl), butyny,l and the like.

The term "aryl" as used herein, alone or as part of a group, includes an organic radical derived from an aromatic hydrocarbon by removal of one hydrogen, and includes monocyclic and polycyclic radicals, such as phenyl, biphenyl, naphthyl.

The term "alkoxy" as used herein, alone or as part of a group, refers to an alkyl ether radical wherein the term alkyl is as defined above. Examples of alkyl ether radical include methoxy, ethoxy, n-propoxy, isopropoxy, n-butoxy, isobutoxy, sec-butoxy, tert-butoxy, and the like.

The term "cycloalkyl" as used herein, alone or in combination, means a saturated or partially saturated monocyclic, bicyclic or tricyclic alkyl radical wherein each cyclic moiety contains from about 3 to about 8 carbon atoms, more preferably from about 3 to about 6 carbon atoms. Examples of such cycloalkyl radicals include cyclopropyl, cyclobutyl, cyclopentyl, cyclohexyl, and the like.

The term "cycloalkylalkyl" as used herein, alone or in combination, means an alkyl radical as defined above which is substituted by a cycloalkyl radical as defined above. Examples of such cycloalkylalkyl radicals include cyclopropylmethyl, cyclobutyl-methyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl, and the like.

The term "substituted" as used herein means that one or more of the hydrogen atoms bonded to carbon atoms in the chain or ring have been replaced with other substituents. Suitable substituents include monovalent hydrocarbon groups including alkyl groups such as methyl groups and monovalent heterogeneous groups including alkoxy groups such as methoxy groups.

The term "unsubstituted" as used herein means that the carbon chain or ring contains no other substituents other than carbon and hydrogen.

The term "branched" as used herein means that the carbon chain is not simply a linear chain. "Unbranched" means that the carbon chain is a linear carbon chain.

The term "saturated" as used herein means that the carbon chain or ring does not contain any double or triple bonds. "Unsaturated" means that the carbon chain or ring contains at least one double bond. An unsaturated carbon chain or ring may include more than one double bond.

The term "hydrocarbon group" means a chain of 1 to 25 carbon atoms, suitably 1 to 12 carbon atoms, more suitably 1 to 10 carbon atoms, and most suitably 1 to 8 carbon atoms. Hydrocarbon groups may have a linear or branched chain structure. Suitably the hydrocarbon groups have one branch.

The term "carbocyclic group" means a saturated or unsaturated hydrocarbon ring. Carbocyclic groups are not aromatic. Carbocyclic groups are monocyclic or polycyclic. Polycyclic carbocyclic groups can be fused, spiro, or bridged ring systems. Monocyclic carbocyclic groups contain 4 to 10 carbon atoms, suitably 4 to 7 carbon atoms, and more suitably 5 to 6 carbon atoms in the ring. Bicyclic carbocyclic groups contain 8 to 12 carbon atoms, preferably 9 to 10 carbon atoms in the rings.

The term "heteroatom" means an atom other than carbon e.g., in the ring of a heterocyclic group or the chain of a heterogeneous group. Preferably, heteroatoms are selected from the group consisting of sulfur, phosphorous, nitrogen and oxygen atoms. Groups containing more than one heteroatom may contain different heteroatoms.

The term "heterocyclic group" means a saturated or unsaturated ring structure containing carbon atoms and 1 or more heteroatoms in the ring. Heterocyclic groups are not aromatic. Heterocyclic groups are monocyclic or polycyclic. Polycyclic heteroaromatic groups can be fused, spiro, or bridged ring systems. Monocyclic heterocyclic groups contain 4 to 10 member atoms (i.e., including both carbon atoms and at least 1 heteroatom), suitably 4 to 7, and more suitably 5 to 6 in the ring. Bicyclic heterocyclic groups contain 8 to 18 member atoms, suitably 9 or 10 in the rings.

The terms "Isomer," "isomeric form," "stereochemically isomeric forms," or "stereoIsomeric forms," as used herein, defines all possible isomeric as well as conformational forms, made up of the same atoms bonded by the same sequence of bonds but having different three-dimensional structures which are not interchangeable, which compounds or intermediates obtained during said process may possess. Unless otherwise mentioned or indicated, the chemical designation of a compound encompasses the mixture of all possible stereochemically isomeric forms which said compound may possess. Said mixture may contain all diastereoisomers, epimers, enantiomers, and/or conformers of the basic molecular structure of said compound. More in particular, stereogenic centers may have the R- or S-configuration, diastereoisomers may have a syn- or anti-configuration, substituents on bivalent cyclic saturated radicals may have either the cis- or trans-configuration and alkenyl radicals may have the E or Z-configuration. All stereochemically isomeric forms of said compound both in pure form or in admixture with each other are intended to be embraced within the scope of the present invention.

As various changes could be made in the above-described materials and methods without departing from the scope of the invention, it is intended that all matter contained in the above description and in the examples given below, shall be interpreted as illustrative and not in a limiting sense.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The compounds of the present invention may be prepared in a number of ways well known to one skilled in the art of organic synthesis. More specifically, the novel compounds of this invention may be prepared using the reactions and techniques described herein. In the description of the synthetic methods described below, it is to be understood that all proposed reaction conditions, including choice of solvent, reaction atmosphere, reaction temperature, duration of the experiment, and workup procedures, are chosen to be the conditions standard for that reaction. It is understood by one skilled in the art of organic synthesis that the functionality present on various portions of the molecule must be compatible with the reagents and reactions proposed. Such restrictions to the substituents, which are not compatible with the reaction conditions, will be apparent to one skilled in the art and alternate methods must then be used. Unless otherwise stated, the starting materials for the examples contained herein are either commercially available or are readily prepared by standard methods from known materials. The compounds of Formula (I) may be synthesized through standard organic chemistry methodology and purification known to those trained in the art of organic synthesis by using commercially available starting materials and reagents.

Data are reported as follows: chemical shift, multiplicity (s=singlet, d=doublet, t=triplet, q=quartet, quint=quintet, etc.; m=multiplet, complex multiplets used where overlapping multiplets are not resolved, b=broadened, obs=obscured, ABq=AB quartet, "apparent" used (e.g. apparent t) when spin systems are distorted due to non-first order effects), coupling constants (Hz), and assignments or relative integration where appropriate. $^{13}$C NMR spectra were reported in ppm from the central deuterated solvent peak (multiplicities indicated when determined).

Example 1. Preparation of (E)-β-chloro-1-(β-(3,4,5-trimethoxyphenyl)acryloyl)-1,5,6,7-tetrahydro-2H-azepin-2-one (XZ-12089)

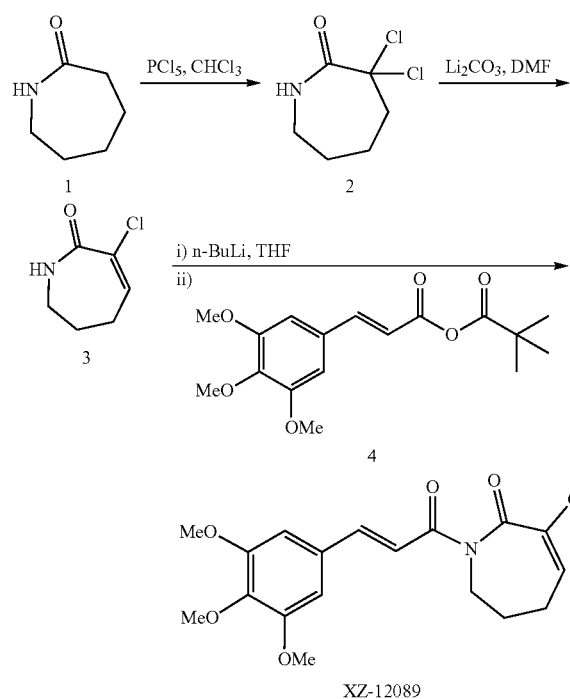

β-Chloro-6,7-dihydro-1H-azepin-2(5H)-one (3): PCl$_5$ (15.6 g) was added to a solution of azepan-2-one (2.83 g) in 50 mL CHCl$_3$ at 0° C. After 10 minutes, the mixture was refluxed for 3 hours and cooled to room temperature. The reaction mixture was poured into ice and extracted with DCM. The organic layer was washed with brine, dried over Na$_2$SO$_4$, and concentrated. The residue was dissolved in 12 mL DMF and Li$_2$CO$_3$ (3.7 g) was added. The resulting mixture was then heated at 120° C. for 16 hours and DMF was removed under vacuum. The product was purified by silica gel column chromatography (1.76 g, 48%). $^1$H NMR (400 MHz, CDCl$_3$) δ 6.63 (t, J=6.7 Hz, 1H), 3.28 (q, J=6.1 Hz, 2H), 2.39 (q, J=7.0 Hz, 2H), 2.03-1.85 (m, 2H) ppm.

XZ-12089: A solution of 3 (1.0 equiv.) in THF was cooled to −78° C., n-BuLi (2.5 M in hexane) (1.0 equiv.) was added dropwise. The resulting mixture was allowed to stir at −78° C. for 1 hour. A solution of (E)-β-(3,4,5-trimethoxyphenyl) acryloyl chloride (4) (1.0 equiv.) in THF was then added dropwise. After addition, the mixture was stirred at −78° C. for 2 hours. The reaction was then quenched with aqueous ammonium chloride solution and was extracted with ethylacetate. The combined organic phases were washed with water, brine, dried over Na$_2$SO$_4$, filtered, and evaporated to dryness. The product was purified by silica gel column chromatography (73% yield). $^1$H NMR (400 MHz, CDCl$_3$) δ 7.74 (d, J=15.5 Hz, 1H), 7.40 (d, J=15.5 Hz, 1H), 6.85-6.75 (m, 3H), 4.01 (t, J=6.3 Hz, 2H), 3.90 (s, 6H), 3.88 (s, 3H), 2.46-2.31 (m, 2H), 2.08-1.93 (m, 2H) ppm; $^{13}$C NMR (100 MHz, CDCl$_3$) δ 167.28, 167.00, 153.35, 145.58, 140.24, 137.09, 130.23, 129.33, 118.89, 109.99, 60.94, 56.18, 41.31, 25.83, 23.60 ppm.

Example 2. Preparation of (E)-β-fluoro-1-(β-(3,4,5-trimethoxyphenyl)acryloyl)-5,6-dihydropyridin-2 (1H)-one (XZ-12316)

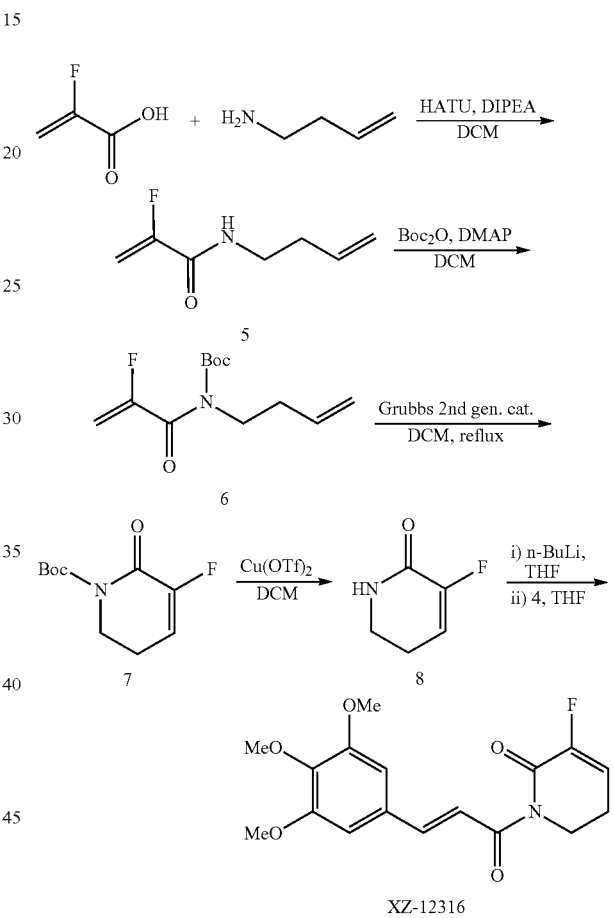

N-(But-β-en-1-yl)-2-fluoroacrylamide (5): A mixture of 2-fluoroacrylic acid (300 mg), but-β-en-1-amine (300 μL), HATU (1.27 g), and DIPEA (550 μL) in 15 mL DCM was stirred at 0° C. for 1 hour then room temperature for 5 hours. The mixture was concentrated and the product was purified by silica gel column chromatography (340 mg, 71%). $^1$H NMR (400 MHz, CDCl$_3$) δ 6.45 (s, 1H), 5.88-5.42 (m, 2H), 5.11-4.99 (m, 3H), 3.36 (q, J=6.5 Hz, 2H), 2.41-2.13 (m, 2H) ppm; [1]C NMR (100 MHz, CDCl$_3$) δ 159.63, 159.33, 157.72, 155.03, 134.68, 117.46, 98.65, 98.50, 38.27, 33.38 ppm.

tert-Butyl but-β-en-1-yl(2-fluoroacryloyl)carbamate (6): A mixture of compound 5 (143 mg), Boc$_2$O (660 mg), and DMAP (12 mg) in 10 mL DCM was stirred at 0° C. for 30 minutes then room temperature overnight. The mixture was concentrated and the product was purified by silica gel column chromatography (130 mg, 54%). $^1$H NMR (400 MHz, CDCl$_3$) δ 5.88-5.65 (m, 1H), 5.50-5.23 (m, 1H), 5.17-4.98 (m, 3H), 3.79-3.67 (m, 2H), 2.43-2.22 (m, 2H), 1.50 (s, 9H) ppm; $^{13}$C NMR (100 MHz, CDCl$_3$) δ 164.57, 164.24, 159.17, 156.48, 152.21, 146.71, 134.54, 117.35, 99.31, 99.16, 84.18, 44.76, 33.09, 27.53, 27.38 ppm.

tert-Butyl β-fluoro-2-oxo-5,6-dihydropyridine-1(2H)-carboxylate (7): A mixture of compound 6 (105 mg) and Grubbs 2nd generation catalyst (18 mg) in 43 mL DCM was refluxed for 4 hours under N$_2$. The mixture was concentrated and the product was purified by silica gel column chromatography (30 mg, 32%). $^1$H NMR (400 MHz, CDCl$_3$) δ 6.37-6.10 (m, 1H), 3.86 (t, J=6.5 Hz, 2H), 2.53-2.35 (m, 2H), 1.52 (s, 9H) ppm; $^{13}$C NMR (100 MHz, CDCl$_3$) δ 158.39 (d, J=31 Hz), 151.98, 149.66 (d, J=253 Hz), 117.03 (d, J=14 Hz), 83.76, 43.49, 27.98, 21.63 (d, J=6 Hz) ppm.

β-Fluoro-5,6-dihydropyridin-2(1H)-one (8): A mixture of compound 7 (30 mg) and Cu(OTf)$_2$ (8 mg) in 10 mL DCM was refluxed for 1 hour. The mixture was concentrated and the product was purified by silica gel column chromatography (11 mg, 68%). $^1$H NMR (400 MHz, CDCl$_3$) δ 6.35 (s, 1H), 6.22-5.87 (m, 1H), 3.61-3.34 (m, 2H), 2.62-2.28 (m, 2H) ppm. $^{13}$C NMR (100 MHz, CDCl$_3$) δ 161.47 (d, J=31 Hz), 149.67 (d, J=254 Hz), 114.79 (d, J=13 Hz), 39.68, 22.16 (d, J=6 Hz) ppm.

XZ-12316: A solution of 8 (1.0 equiv.) in THF was cooled to −78° C., n-BuLi (2.5 M in hexane) (1.0 equiv.) was added dropwise. The resulting mixture was allowed to stir at −78° C. for 1 hour. A solution of 4 (1.0 equiv.) in THF was then added dropwise. After addition, the mixture was stirred at −78° C. for 2 hours. The reaction was then quenched with aqueous ammonium chloride solution and was extracted with ethylacetate. The combined organic phases were washed with water, brine, dried over Na$_2$SO$_4$, filtered, and evaporated to dryness. The product was purified by silica gel column chromatography (yield 65%). $^1$H NMR (400 MHz, CDCl$_3$) δ 7.72 (d, J=15.5 Hz, 1H), 7.45 (d, J=15.5 Hz, 1H), 6.81 (s, 2H), 6.63-6.27 (m, 1H), 4.08 (t, J=6.4 Hz, 2H), 3.90 (s, 6H), 3.89 (s, 3H), 2.69-2.41 (m, 2H) ppm. $^{13}$C NMR (100 MHz, CDCl$_3$) δ 168.00 (d, J=2 Hz), 160.55 (d, J=31 Hz), 153.34, 149.60 (d, J=253 Hz), 145.07, 140.19, 130.26, 120.04, 118.84 (d, J=14 Hz), 105.52, 60.94, 56.14, 41.65, 21.77 (d, J=5 Hz) ppm.

Example 3. Preparation of (E)-β-(trifluoromethyl)-1-(β-(3,4,5-trimethoxyphenyl)acryloyl)-5,6-dihydropyridin-2(1H)-one (XZ-13095)

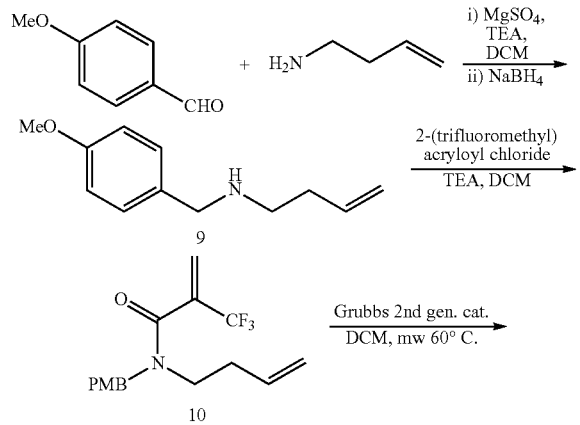

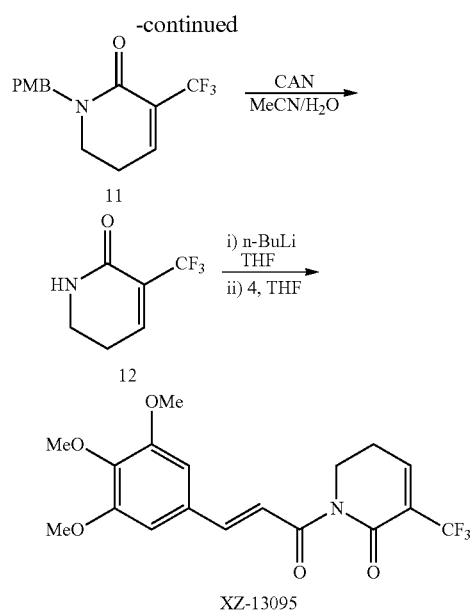

N-(4-Methoxybenzyl)but-β-en-1-amine (9): A mixture of 4-methoxybenzaldehyde (300 μL), but-β-en-1-amine (225 μL), TEA (685 μL), and MgSO$_4$ (600 mg) in 15 mL DCM was stirred at room temperature overnight. The mixture was cooled to 0° C., NaBH$_4$ (105 mg) and 5 mL MeOH were added. The resulting mixture was stirred at this temperature for 2 hours and pH of the mixture was adjusted to 2.0 by adding 1N HCl (aq). The mixture was extracted with DCM and the water phase was collected. The pH of the water phase was adjusted to 8.0 by adding aq. NaHCO$_3$ solution and extracted with DCM. The combined organic layers were washed with brine, dried over Na$_2$SO$_4$, and concentrated to afford the desired product (470 mg, 99%). $^1$H NMR (400 MHz, CDCl$_3$) δ 7.21 (d, J=8.5 Hz, 2H), 6.84 (d, J=8.6 Hz, 2H), 5.91-5.59 (m, 1H), 5.17-4.91 (m, 2H), 3.77 (s, 3H), 3.71 (s, 2H), 2.67 (t, J=6.9 Hz, 2H), 2.33-2.14 (m, 2H) ppm.

N-(But-β-en-1-yl)-N-(4-methoxybenzyl)-2-(trifluoromethyl)acrylamide (10): Compound 9 (320 mg), 2-(trifluoromethyl)acryloyl chloride (400 mg), and TEA (1.74 mL) in 5 mL DCM were stirred at room temperature overnight. The reaction was quenched with water and extracted with DCM. The combined organic layers were washed with brine, dried over Na$_2$SO$_4$, and concentrated. The product was purified by silica gel column chromatography (235 mg, 45%). $^1$H NMR (400 MHz, CDCl$_3$) δ 7.24-6.99 (m, 2H), 6.99-6.76 (m, 2H), 6.20-5.88 (m, 1H), 5.86-5.50 (m, 2H), 5.16-4.98 (m, 2H), 4.78-4.40 (m, 2H), 3.80 (s, 3H), 3.54-3.14 (m, 2H), 2.52-2.12 (m, 2H) ppm.

1-(4-Methoxybenzyl)-β-(trifluoromethyl)-5,6-dihydropyridin-2(1H)-one (11): A mixture of compound 10 (235 mg) and Grubbs 2nd generation catalyst (38 mg) in 40 mL DCM was heated using microwave at 60° C. for 2 hours. The mixture was concentrated and the product was purified by silica gel column chromatography (170 mg, 67%). $^1$H NMR (400 MHz, CDCl$_3$) δ 7.23 (d, J=8.3 Hz, 2H), 7.14 (br s, 1H), 6.86 (d, J=8.3 Hz, 2H), 4.57 (s, 2H), 3.80 (s, 3H), 3.35 (t, J=7.1 Hz, 2H) ppm; $^{13}$C NMR (100 MHz, CDCl$_3$) δ 159.55, 159.17, 141.92 (q, J=5.3 Hz), 129.59, 128.76, 126.46 (q, J=30 Hz), 121.58 (q, J=271 Hz), 114.07, 55.25, 48.99, 43.47, 23.48 ppm.

3-(Trifluoromethyl)-5,6-dihydropyridin-2(1H)-one (12): A mixture of compound 11 (114 mg), anisole (38 mg) in 1 mL TFA was heated at 65° C. overnight. The mixture was concentrated and the product was purified by silica gel column chromatography (60 mg, 91%). $^1$H NMR (400 MHz, CDCl$_3$) δ 7.26-7.22 (m, 1H), 6.38 (br s, 1H), 3.57-3.40 (m, 2H), 2.62-2.47 (m, 2H) ppm; $^{13}$C NMR (100 MHz, CDCl$_3$) δ 161.41, 143.75 (q, J=5.3. Hz), 126.36 (q, J=31 Hz), 121.37 (q, J=271 Hz), 38.93, 23.71 ppm.

XZ-13095: A solution of 12 (1.0 equiv.) in THF was cooled to −78° C. n-BuLi (2.5 M in hexane) (1.0 equiv.) was added dropwise. The resulting mixture was allowed to stir at −78° C. for 1 hour. A solution of 4 (1.0 equiv.) in THF was then added dropwise. After addition, the mixture was stirred at −78° C. for 2 hours. The reaction was then quenched with aqueous ammonium chloride solution and was extracted with ethylacetate. The combined organic phases were washed with water, brine, dried over Na$_2$SO$_4$, filtered, and evaporated to dryness. The product was purified by silica gel column chromatography (Yield 14%). $^1$H NMR (400 MHz, CDCl$_3$) δ 7.70 (d, J=15.5 Hz, 1H), 7.59-7.50 (m, 1H), 7.41 (d, J=15.5 Hz, 1H), 6.79 (s, 2H), 4.07 (t, J=6.5 Hz, 2H), 3.88 (s, 6H), 3.87 (s, 3H), 2.74-2.55 (m, 2H) ppm.

Example 4. Preparation of (E)-2-(β-(3,4,5-trimethoxyphenyl)acryloyl)-2H-1,2-oxazin-3(6H)-one (XZ-12037)

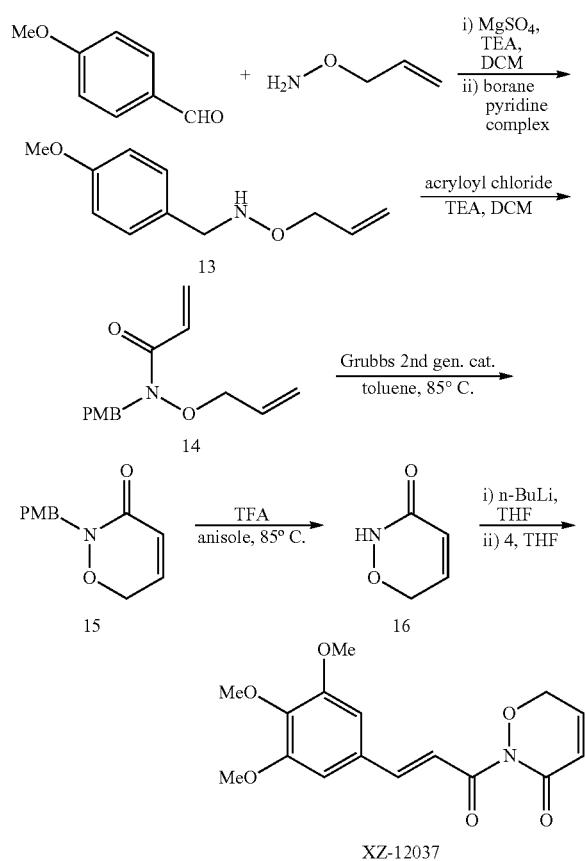

O-Allyl-N-(4-methoxybenzyl)hydroxylamine (13): A mixture of 4-methoxybenzaldehyde (3.65 mL), 0-allylhydroxylamine hydrochloride (3.3 g), TEA (8.35 mL), and MgSO$_4$ (7.2 g) in 100 mL DCM was stirred at room temperature for 3 days. The mixture was filtered and the filtrate was concentrated under reduced pressure. The residue was dissolved in 100 mL EtOH and mixed with borane pyridine complex (11.2 g) and 60 mL 6 N HCl (aq) at 0° C. After 2 hours, the pH of the reaction mixture was adjusted to 8.0 by adding aq. NaHCO$_3$ and extracted with ethyl acetate. The combined organic layers were washed with brine, dried over Na$_2$SO$_4$, and concentrated. The product was purified by silica gel column chromatography (3.32 g, 57%). $^1$H NMR (400 MHz, CDCl$_3$) δ 7.25 (d, J=8.4 Hz, 2H), 6.85 (d, J=8.5 Hz, 2H), 6.01-5.76 (m, 1H), 5.36-5.00 (m, 2H), 4.14 (d, J=6.0 Hz, 2H), 3.98 (s, 2H), 3.78 (s, 3H) ppm; $^{13}$C NMR (100 MHz, CDCl$_3$) δ 159.00, 134.49, 130.21, 129.46, 117.60, 113.79, 75.04, 55.92, 55.23 ppm.

N-(Allyloxy)-N-(4-methoxybenzyl)acrylamide (14): A mixture of 13 (300 mg), acryloyl chloride (163 μL), and TEA (300 μL) in 10 mL DCM was stirred at 0° C. for 1 hour then room temperature for 1 hour. The mixture was poured into water and extracted with DCM. The combined organic layers were washed with brine, dried over Na$_2$SO$_4$, and concentrated. The product was purified by silica gel column chromatography (358 mg, 94%). $^1$H NMR (400 MHz, CDCl$_3$) δ 7.27 (d, J=8.4 Hz, 2H), 6.85 (d, J=8.8 Hz, 2H), 6.80-6.67 (m, 1H), 6.55-6.36 (m, 1H), 5.96-5.82 (m, 1H), 5.81-5.69 (m, 1H), 5.41-5.15 (m, 2H), 4.80 (s, 2H), 4.25 (d, J=6.3 Hz, 2H), 3.78 (s, 3H) ppm; $^{13}$C NMR (100 MHz, CDCl$_3$) δ 166.71, 159.16, 131.10, 129.94, 129.42, 128.42, 126.34, 120.65, 113.90, 76.44, 55.21, 49.63 ppm.

2-(4-Methoxybenzyl)-2H-1,2-oxazin-3(6H)-one (15): A mixture of compound 14 (300 mg) and Grubbs 2nd generation catalyst (30 mg) in 30 mL toluene was heated at 85° C. for 1 hour under N$_2$. The mixture was then concentrated and the product was purified by silica gel column chromatography (250 mg, 95%). $^1$H NMR (400 MHz, CDCl$_3$) δ 7.30 (d, J=8.6 Hz, 2H), 6.87 (d, J=8.6 Hz, 2H), 6.72-6.61 (m, 1H), 6.12-5.96 (m, 1H), 4.72 (s, 2H), 4.50-4.40 (m, 2H), 3.80 (s, 3H) ppm; $^{13}$C NMR (100 MHz, CDCl$_3$) δ 164.60, 159.13, 138.93, 129.72, 128.48, 122.57, 113.86, 67.41, 55.23, 49.69 ppm.

2H-1,2-Oxazin-3(6H)-one (16): A mixture of compound 15 (14 mg) and anisole (20 mg) in 1 mL TFA was heated at 85° C. overnight. The mixture was then concentrated and the product was purified by silica gel column chromatography (5 mg, 68%).

XZ-12037: A solution of 16 (1.0 equiv.) in THF was cooled to −78° C. n-BuLi (2.5 M in hexane) (1.0 equiv.) was added dropwise. The resulting mixture was allowed to stir at −78° C. for 1 hour. A solution of 4 (1.0 equiv.) in THF was then added dropwise. After addition, the mixture was stirred at −78° C. for 2 hours. The reaction was then quenched with aqueous ammonium chloride solution and was extracted with ethyl acetate. The combined organic phases were washed with water, brine, dried over Na$_2$SO$_4$, filtered, and evaporated to dryness. The product was purified by silica gel column chromatography. $^1$H NMR (400 MHz, CDCl$_3$) δ 7.79 (d, J=15.6 Hz, 1H), 7.30 (d, J=15.6 Hz, 1H), 7.11-7.01 (m, 1H), 6.79 (s, 2H), 6.20-6.04 (m, 1H), 4.91-4.63 (m, 2H), 3.88 (s, 6H), 3.87 (s, 3H) ppm; $^{13}$C NMR (100 MHz, CDC$_3$) δ 162.86, 162.18, 153.37, 146.20, 143.18, 140.43, 130.05, 123.05, 117.71, 105.66, 68.80, 60.96, 56.16 ppm.

Example 5. Preparation of (E)-4-fluoro-2-(β-(3,4,5-trimethoxyphenyl)acryloyl)-2H-1,2-oxazin-3(6H)-one (XZ-13100)

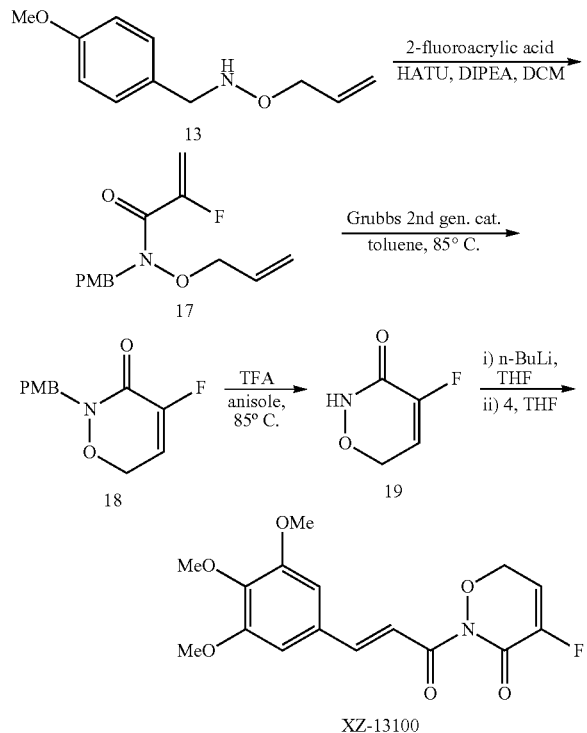

N-(Allyloxy)-2-fluoro-N-(4-methoxybenzyl)acrylamide (17): A mixture of 13 (390 mg), 2-fluoroacrylic acid (180 mg), HATU (760 mg), and DIPEA (330 µL) in 20 mL DCM was stirred at −78° C. for 30 minutes then room temperature overnight. The reaction mixture was poured into water and extracted with DCM. The combined organic layers were washed with brine, dried over $Na_2SO_4$, and concentrated. The product was purified by silica gel column chromatography (494 mg, 93%). $^1$H NMR (400 MHz, CDCl$_3$) δ 7.26 (d, J=8.5 Hz, 2H), 6.84 (d, J=8.6 Hz, 2H), 5.89-5.77 (m, 1H), 5.43 (dd, J=46.7, 3.3 Hz, 1H), 5.31-5.21 (m, 2H), 5.17 (dd, J=16.4, 3.3 Hz, 1H), 4.74 (s, 2H), 4.28 (d, J=6.3 Hz, 2H), 3.76 (s, 3H) ppm; $^{13}$C NMR (100 MHz, CDCl$_3$) δ 161.82 (d, J=30 Hz), 159.34, 156.34 (d, J=268 Hz), 131.15, 130.01, 127.58, 120.71, 113.95, 101.98 (d, J=6 Hz), 76.54 (d, J=2.3 Hz), 55.21, 51.15 ppm.

4-Fluoro-2-(4-methoxybenzyl)-2H-1,2-oxazin-3(6H)-one (18): A mixture of compound 17 (260 mg) and Grubbs 2nd generation catalyst (40 mg) in 50 mL toluene was refluxed for 2 hours under $N_2$. The reaction mixture was then concentrated and the product was purified by silica gel column chromatography (68 mg, 29%). $^1$H NMR (400 MHz, CDCl$_3$) δ 7.29 (d, J=8.6 Hz, 2H), 6.87 (d, J=8.6 Hz, 2H), 6.16-6.03 (m, 1H), 4.71 (s, 2H), 4.57 (dd, J=5.7, 3.7 Hz, 2H), 3.80 (s, 3H) ppm; $^{13}$C NMR (100 MHz, CDCl$_3$) δ 160.64 (d, J=21 Hz), 159.34, 148.10 (d, J=260 Hz), 129.93, 127.61, 113.94, 113.04 (d, J=12 Hz), 66.41 (d, J=7 Hz), 55.24, 50.09 (d, J=1.5 Hz) ppm.

4-Fluoro-2H-1,2-oxazin-3(6H)-one (19): A mixture of compound 18 (15 mg) and anisole (20 mg) in 1 mL TFA was heated at 85° C. overnight. The reaction mixture was then concentrated and the product was purified by silica gel column chromatography (5 mg, 68%). $^1$H NMR (400 MHz, CDCl$_3$) δ 7.89 (s, 1H), 6.41-6.03 (m, 1H), 4.81-4.53 (m, 2H) ppm.

XZ-13100: A solution of 19 (1.0 equiv.) in THF was cooled to −78° C., n-BuLi (2.5 M in hexane) (1.0 equiv.) was added dropwise. The resulting mixture was allowed to stir at −78° C. for 1 hour. A solution of 4 (1.0 equiv.) in THF was then added dropwise. After addition, the mixture was stirred at −78° C. for 2 hours. The reaction was then quenched with aqueous ammonium chloride solution and was extracted with ethyl acetate. The combined organic phases were washed with water, brine, dried over $Na_2SO_4$, filtered, and evaporated to dryness. The product was purified by silica gel column chromatography (Yield 18%). $^1$H NMR (400 MHz, CDCl$_3$) δ 7.84 (d, J=15.6 Hz, 1H), 7.31 (d, J=15.6 Hz, 1H), 6.82 (s, 2H), 6.59-6.46 (m, 1H), 4.90-4.81 (m, 2H), 3.90 (s, 6H), 3.90 (s, 3H) ppm; $^{13}$C NMR (100 MHz, CDCl$_3$) δ 162.26, 157.90 (d, J=32 Hz), 153.41, 147.68 (d, J=263 Hz), 147.34, 140.73, 129.73, 117.21 (d, J=13 Hz), 116.74, 105.77, 67.88 (d, J=6 Hz), 60.98, 56.17 ppm.

Example 6. Preparation of (E)-4-bromo-2-(β-(3,4,5-trimethoxyphenyl)acryloyl)-2H-1,2-oxazin-3(6H)-one (XZ-13907)

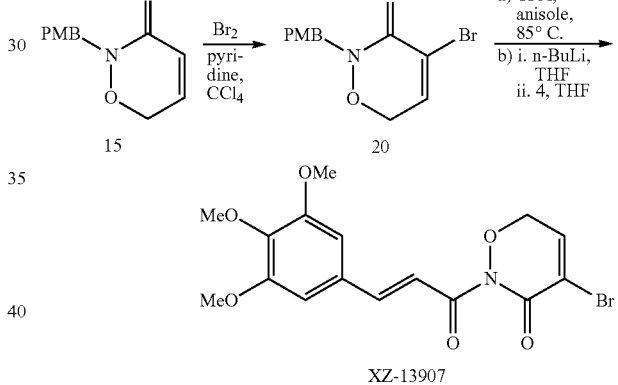

4-Bromo-2-(4-methoxybenzyl)-2H-pyran-3(6H)-one (20): A mixture of 15 (190 mg), Br$_2$ (152 mg), pyridine (2.0 mL), and CCl$_4$ (2.0 mL) was stirred at room temperature overnight. The reaction mixture was then poured into water and extracted with ethyl acetate. The combined organic layers were washed with brine, dried over $Na_2SO_4$, and concentrated. The product was purified by silica gel column chromatography (120 mg, 46%). $^1$H NMR (400 MHz, CDCl$_3$) δ 7.28 (d, J=8.6 Hz, 2H), 7.00 (t, J=3.7 Hz, 1H), 6.85 (d, J=8.6 Hz, 2H), 4.74 (s, 2H), 4.43 (d, J=3.7 Hz, 2H), 3.78 (s, 3H) ppm; $^{13}$C NMR (100 MHz, CDCl$_3$) δ 160.59, 159.33, 139.11, 129.96, 127.89, 116.26, 113.93, 68.93, 55.24, 51.08 ppm.

XZ-13907: A solution of 20 (1.0 equiv.) in THF was cooled to −78° C., n-BuLi (2.5 M in hexane) (1.0 equiv.) was added dropwise. The resulting mixture was allowed to stir at −78° C. for 1 hour. A solution of 4 (1.0 equiv.) in THF was then added dropwise. After addition, the mixture was stirred at −78° C. for 2 hours. The reaction was then quenched with aqueous ammonium chloride solution and was extracted with ethyl acetate. The combined organic phases were washed with water, brine, dried over $Na_2SO_4$, filtered, and evaporated to dryness. The product was purified by silica gel column chromatography. $^1$H NMR (400 MHz, CDCl$_3$) δ 7.84 (d, J=15.7 Hz, 1H), 7.43-7.36 (m, 1H), 7.31 (d, J=15.6 Hz, 1H), 6.82 (s, 2H), 4.83-4.68 (m, 2H), 3.93-3.87 (m, 9H) ppm; $^{13}$C NMR (100 MHz, CDCl$_3$) δ 162.57, 158.34, 153.40, 147.25, 143.22, 129.82, 122.31, 117.00, 107.56, 105.79, 70.40, 60.98, 56.21 ppm.

Example 7. Preparation of (E)-4-iodo-2-(β-(3,4,5-trimethoxyphenyl)acryloyl)-2H-1,2-oxazin-3(6H)-one (XZ-13126)

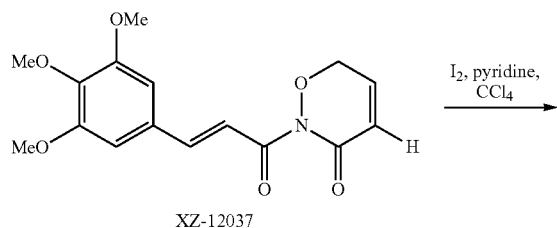

XZ-12037

→ I$_2$, pyridine, CCl$_4$

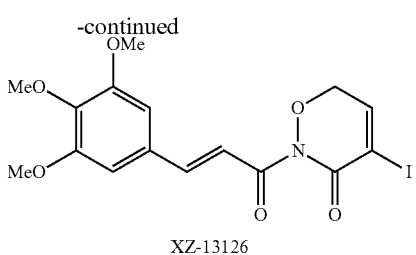

XZ-13126

A mixture of XZ-12037 (16 mg), I$_2$ (6.5 mg), pyridine (0.5 mL), and CCl$_4$ (0.5 mL) was stirred at room temperature for 3 days. The reaction mixture was then poured into water and extracted with ethyl acetate. The combined organic layers were washed with brine, dried over Na$_2$SO$_4$, and concentrated. The product was purified by silica gel column chromatography (4.0 mg, 18%). $^1$H NMR (400 MHz, CDCl$_3$) δ 7.83 (d, J=15.6 Hz, 1H), 7.77-7.60 (m, 1H), 7.31 (d, J=15.6 Hz, 1H), 6.82 (s, 2H), 4.70 (d, J=3.5 Hz, 2H), 3.91 (s, 6H), 3.90 (s, 3H) ppm; $^{13}$C NMR (100 MHz, CDCl$_3$) δ 162.63, 158.33, 153.39, 151.65, 147.18, 140.66, 129.84, 117.07, 105.82, 92.24, 71.44, 60.98, 56.23 ppm.

Example 8. Evaluation of Compounds of Formula I for their Ability to Selectively Kill Senescent Cells Normal WI-38 cells and IR-induced senescent cells were incubated with increasing concentrations of compounds of Formula (I). At 72 hours post-treatment cell viability was measured and ED$_{50}$ was calculated. Table 1 depicts the ED50 values of the compounds of Formula (I) against normal and IR-induced senescent cells.

TABLE 1

ED50 of compounds of Formula I against normal and senescent cells.

| No | Structure | EC$_{50}$ (μM) normal WI-38 | EC$_{50}$ (μM) IR-SC WI-38 | SI |
|---|---|---|---|---|
| 1 | (MeO, MeO, OMe phenyl)-CH=CH-C(O)-N-ring with F | 12.1 | 15.3 | 0.8 |
| 2 | (MeO, MeO, OMe phenyl)-CH=CH-C(O)-N-ring with Cl | 5.3 | 0.65 | 8.2 |
| 3 | (MeO, MeO, OMe phenyl)-CH=CH-C(O)-N-ring with Br | 5.4 | 0.52 | 10.4 |

TABLE 1-continued

ED50 of compounds of Formula I against normal and senescent cells.

| No | Structure | EC$_{50}$ (μM) normal WI-38 | EC$_{50}$ (μM) IR-SC WI-38 | SI |
|----|-----------|------------------------------|----------------------------|-----|
| 4 | 3,4,5-trimethoxycinnamoyl-3-iodo-5,6-dihydropyridin-2(1H)-one | 18.3 | 2.3 | 8.0 |
| 5 | 3,4,5-trimethoxycinnamoyl-3-chloro-azepin-2-one | 1.7 | 0.45 | 3.8 |
| 6 | 3,4,5-trimethoxycinnamoyl-3-bromo-azepin-2-one | 3.6 | 0.56 | 6.4 |
| 7 | 3,4,5-trimethoxycinnamoyl-oxazinone | 47.7 | 8.0 | 6.0 |
| 8 | 4-methoxycinnamoyl-3-chloro-5,6-dihydropyridin-2(1H)-one | 0.35 | 0.51 | 0.7 |
| 9 | 4-methoxycinnamoyl-3-bromo-5,6-dihydropyridin-2(1H)-one | 1.1 | 0.63 | 1.7 |
| 10 | 4-methoxycinnamoyl-3-chloro-azepin-2-one | 1.5 | 0.16 | 9.4 |
| 11 | 4-methoxycinnamoyl-3-bromo-azepin-2-one | 5.8 | 1.3 | 4.5 |

TABLE 1-continued

ED50 of compounds of Formula I against normal and senescent cells.

| No | Structure | EC$_{50}$ (μM) normal WI-38 | EC$_{50}$ (μM) IR-SC WI-38 | SI |
|---|---|---|---|---|
| 12 | 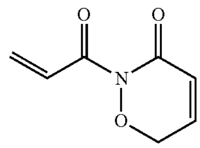 | 16.3 | 5.7 | 2.9 |
| 13 | 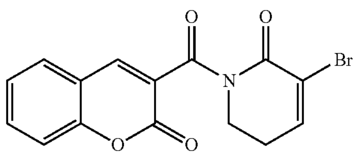 [SMILES: O=C1C(Br)=CCCN1C(=O)c1cc2ccccc2oc1=O] | 6.2 | 1.7 | 3.6 |
| 14 | 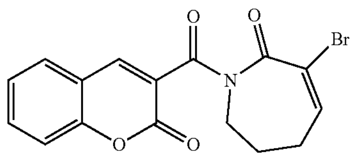 [SMILES: O=C1C(Br)=CCCCN1C(=O)c1cc2ccccc2oc1=O] | 5.0 | 4.0 | 1.3 |
| 15 | 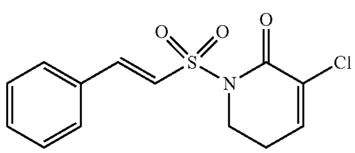 [SMILES: O=C1C(Cl)=CCCN1S(=O)(=O)/C=C/c1ccccc1] | 8.8 | 0.94 | 9.4 |
| 16 | 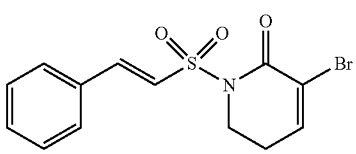 [SMILES: O=C1C(Br)=CCCN1S(=O)(=O)/C=C/c1ccccc1] | 28.1 | 2.8 | 10 |

All cited references are herein expressly incorporated by reference in their entirety.

Whereas particular embodiments have been described above for purposes of illustration, it will be appreciated by those skilled in the art that numerous variations of the details may be made without departing from the disclosure as described in the appended claims.

What is claimed is:

1. A compound, the compound of Formula (I):

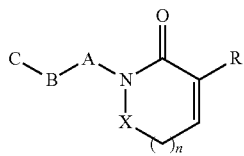

(I)

wherein:
R is selected from the group consisting of hydrogen, deuterium, halogen, CF$_3$, NO$_2$, and CN;
X is selected from the group consisting of CH$_2$, O, NH, S, C(O), and S(O)$_2$;
n is an integer from 0-2;
A is S(O)$_2$;
B is selected from the group consisting of

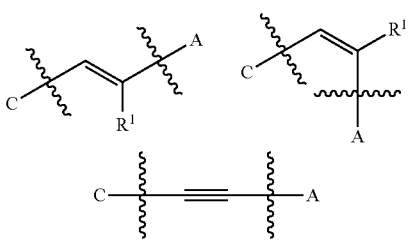

wherein:
R$^1$ is selected from the group consisting of hydrogen, deuterium, halogen, CF$_3$, CN, OH, OCH$_3$, OR', SR', NR'R', NR'COR', NR'CONR'R', NR'CO$_2$R', COR', CO$_2$R', NOR', NO$_2$, CONR'R', OC(O)NR'R', SO$_2$R', SO$_2$NR'R', NR'SO$_2$R', NR'SO$_2$NR'R', C(O)C(O)R', C(O)CH$_2$C(O)R', a substituted or unsubstituted C$_1$-C$_6$ alkyl, a substituted or unsubstituted C$_1$-C$_6$ alkenyl, a substituted or unsubstituted C$_1$-C$_6$ alkynyl, a substituted or unsubstituted aryl, and a substituted or unsubstituted heteroaryl;
R' is independently selected from the group consisting of hydrogen, substituted C$_1$-C$_4$ aliphatic moiety, aliphatic moiety containing nitrogen, oxygen, or sulfur, or alternately, two R' moieties bound to the same nitrogen atom are optionally taken together with the nitrogen atom to form a β-7 membered saturated or unsaturated ring having 1-2 additional heteroatoms independently selected from the group consisting of nitrogen, oxygen, or sulfur;

C is hydrogen or

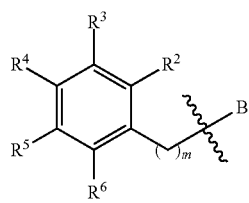

wherein:
- $R^2$, $R^3$, $R^4$, $R^5$, and $R^6$ are each independently selected from the group consisting of hydrogen, deuterium, halogen, $CF_3$, CN, OH, $OCH_3$, OR", SR", NR"R", NR"COR", NR"CONR"R", NR"$CO_2$R", COR", $CO_2$R", NOR", $NO_2$, CONR"R", OC(O)NR"R", $SO_2$R", $SO_2$NR"R", NR"$SO_2$R", NR"$SO_2$NR"R", C(O)C(O)R", and C(O)$CH_2$C(O)R", a substituted or unsubstituted $C_1$ to $C_6$ alkyl, a substituted or unsubstituted $C_1$ to $C_6$ alkenyl, a substituted or unsubstituted $C_1$ to $C_6$ alkynyl, a substituted or unsubstituted aryl, and a substituted or unsubstituted heteroaryl;
- R" is independently selected from the group consisting of hydrogen, substituted $C_1$-$C_4$ aliphatic moiety, aliphatic moiety containing nitrogen, oxygen, or sulfur, or alternately, two R" moieties bound to the same nitrogen atom are optionally taken together with the nitrogen atom to form a β-7 membered saturated or unsaturated ring having 1-2 additional heteroatoms independently selected from the group consisting of nitrogen, oxygen, or sulfur;
- Optionally, $R^2$ and $R^3$, $R^3$ and $R^4$, $R^4$ and $R^5$, and $R^5$ and $R^6$ are taken together to form a 4-8 membered saturated or unsaturated ring having 0-3 heteroatoms independently selected from the group consisting of nitrogen, oxygen, or sulfur;
- m is an integer from 0-6; and
- Optionally, the phenyl ring in C or R' and C taken together may be replaced by the following one or more monocyclic aryl, one or more heteroaryl, a β-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from the group consisting of nitrogen, oxygen or sulfur, or an 6-10 membered bicyclic heteroaryl ring having 1-5 heteroatoms independently selected from the group consisting of nitrogen, oxygen, or sulfur.

2. The compound of claim 1, wherein R is selected from the group consisting of hydrogen, F, Cl, Br, I, and $CF_3$.

3. The compound of claim 1, wherein X is selected from the group consisting of $CH_2$ and O.

4. The compound of claim 1, wherein n is an integer from 1-2.

5. The compound of claim 1, wherein B is

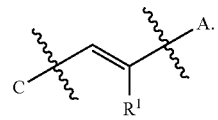

6. The compound of claim 1, wherein C is

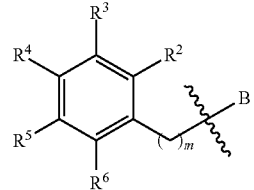

7. The compound of claim 6, wherein $R^2$, $R^3$, $R^4$, $R^5$, and $R^6$ are each independently selected from the group consisting of hydrogen, $OCH_3$, and $O(CH_2)N(CH_3)_2$.

8. The compound of claim 7, wherein $R^2$ and $R^6$ are hydrogen and $R^3$, $R^4$, and $R^5$ are $OCH_3$.

9. A method of selectively killing one or more senescent cells in a subject in need thereof, the method comprising administering to the subject a composition comprising a therapeutically effective amount of a compound of Formula (I):

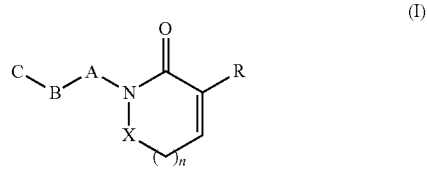

wherein:
- R is selected from the group consisting of hydrogen, deuterium, halogen, $CF_3$, $NO_2$, and CN;
- X is selected from the group consisting of $CH_2$, O, NH, S, C(O), and $S(O)_2$;
- n is an integer from 0-2;
- A is $S(O)_2$;
- B is selected from the group consisting of

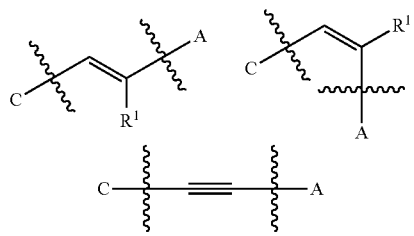

wherein:
- $R^1$ is selected from the group consisting of hydrogen, deuterium, halogen, $CF_3$, CN, OH, $OCH_3$, OR', SR', NR'R', NR'COR', NR'CONR'R', NR'$CO_2$R', COR', $CO_2$R', NOR', $NO_2$, CONR'R', OC(O)NR'R', $SO_2$R', $SO_2$NR'R', NR'$SO_2$R', NR'$SO_2$NR'R', C(O)C(O)R', C(O)CH$_2$C(O)R', a substituted or unsubstituted C$_1$-C$_6$ alkyl, a substituted or unsubstituted C$_1$-C$_6$ alkenyl, a substituted or unsubstituted C$_1$-C$_6$ alkynyl, a substituted or unsubstituted aryl, and a substituted or unsubstituted heteroaryl;

R' is independently selected from the group consisting of hydrogen, substituted C$_1$-C$_4$ aliphatic moiety, aliphatic moiety containing nitrogen, oxygen, or sulfur, or alternately, two R' moieties bound to the same nitrogen atom are optionally taken together with the nitrogen atom to form a β-7 membered saturated or unsaturated ring having 1-2 additional heteroatoms independently selected from the group consisting of nitrogen, oxygen, or sulfur;

C is hydrogen or

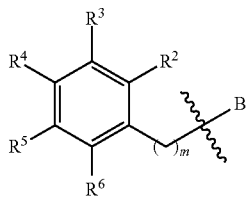

wherein:
R$^2$, R$^3$, R$^4$, R$^5$, and R$^6$ are each independently selected from the group consisting of hydrogen, deuterium, halogen, CF$_3$, CN, OH, OCH$_3$, OR", SR", NR"R", NR"COR", NR"CONR"R", NR"CO$_2$R", COR", CO$_2$R", NOR", NO$_2$, CONR"R", OC(O)NR"R", SO$_2$R", SO$_2$NR"R", NR"SO$_2$R", NR"SO$_2$NR"R", C(O)C(O)R", and C(O)CH$_2$C(O)R", a substituted or unsubstituted C$_1$ to C$_6$ alkyl, a substituted or unsubstituted C$_1$ to C$_6$ alkenyl, a substituted or unsubstituted C$_1$ to C$_6$ alkynyl, a substituted or unsubstituted aryl, and a substituted or unsubstituted heteroaryl;

R" is independently selected from the group consisting of hydrogen, substituted C$_1$-C$_4$ aliphatic moiety, aliphatic moiety containing nitrogen, oxygen, or sulfur, or alternately, two R" moieties bound to the same nitrogen atom are optionally taken together with the nitrogen atom to form a β-7 membered saturated or unsaturated ring having 1-2 additional heteroatoms independently selected from the group consisting of nitrogen, oxygen, or sulfur;

Optionally, R$^2$ and R$^3$, R$^3$ and R$^4$, R$^4$ and R$^5$, and R$^5$ and R$^6$ are taken together to form a 4-8 membered saturated or unsaturated ring having 0-3 heteroatoms independently selected from the group consisting of nitrogen, oxygen, or sulfur;

m is an integer from 0-6; and

Optionally, the phenyl ring in C or R' and C taken together may be replaced by the following one or more monocyclic aryl, one or more heteroaryl, a β-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from the group consisting of nitrogen, oxygen or sulfur, or an 6-10 membered bicyclic heteroaryl ring having 1-5 heteroatoms independently selected from the group consisting of nitrogen, oxygen, or sulfur.

10. The method of claim 9, wherein the senescent cells are senescent due to replicative cellular senescence, premature cellular senescence, or therapy-induced senescence.

11. The method of claim 9, wherein the senescent cells are from an age-related disease or condition.

12. The method of any of claim 9, wherein the subject has a received DNA-damaging therapy.

13. The method of claim 11, wherein the age-related disease or condition is a degenerative disease or a function-decreasing disorder.

14. The method of claim 9, wherein the composition further comprises at least one additional senolytic agent.

15. The method of claim 14, wherein the additional senolytic agent is selected from the group consisting of MDM2 inhibitors, BCL-2 family inhibitors, Akt kinase inhibitors and combinations thereof.

16. The method of claim 9, wherein R is selected from the group consisting of hydrogen, F, Cl, Br, I, and CF$_3$.

17. The method of claim 9, wherein X is selected from the group consisting of CH$_2$ and O.

* * * * *